US011623945B2

(12) United States Patent
Tabor et al.

(10) Patent No.: US 11,623,945 B2
(45) Date of Patent: Apr. 11, 2023

(54) IMMUNOSTIMULATING COMPOSITIONS AND USES THEREFORE

(71) Applicants: MEAT & LIVESTOCK AUSTRALIA LIMITED, North Sydney (AU); THE STATE OF QUEENSLAND, Brisbane (AU); UNITED STATES OF AMERICA, AS REPRESENTED BY THE SECRETARY OF AGRICULTURE, Washington, DC (US)

(72) Inventors: Alicja Tabor, Brisbane (AU); Matthew Bellgard, Brisbane (AU); Manuel Rodriguez Valle, Brisbane (AU); Felicito Guerrero, Brisbane (AU)

(73) Assignee: THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 122 days.

(21) Appl. No.: 16/483,806

(22) PCT Filed: Feb. 6, 2018

(86) PCT No.: PCT/AU2018/050080
§ 371 (c)(1),
(2) Date: Aug. 6, 2019

(87) PCT Pub. No.: WO2018/141029
PCT Pub. Date: Aug. 9, 2018

(65) Prior Publication Data
US 2020/0062810 A1 Feb. 27, 2020

(30) Foreign Application Priority Data
Feb. 6, 2017 (AU) .................................. 2017900358

(51) Int. Cl.
*C07K 14/435* (2006.01)
*A61K 39/00* (2006.01)
*A61P 33/00* (2006.01)

(52) U.S. Cl.
CPC .... *C07K 14/43527* (2013.01); *A61K 39/0003* (2013.01); *A61P 33/00* (2018.01); *A61K 2039/53* (2013.01); *A61K 2039/552* (2013.01)

(58) Field of Classification Search
None
See application file for complete search history.

(56) References Cited

U.S. PATENT DOCUMENTS

| 4,946,778 | A | 8/1990 | Ladner et al. |
|---|---|---|---|
| 5,223,409 | A | 6/1993 | Ladner et al. |
| 5,646,017 | A | 7/1997 | Bachmair et al. |
| 5,759,552 | A | 6/1998 | Paoletti et al. |
| 5,837,821 | A | 11/1998 | Wu |
| 5,892,020 | A | 4/1999 | Mezes et al. |
| 6,207,646 | B1 | 3/2001 | Krieg et al. |
| 6,300,064 | B1 | 10/2001 | Knappik et al. |
| 6,406,705 | B1 | 6/2002 | Davis et al. |
| 6,783,761 | B2 | 8/2004 | Grimes et al. |
| 6,875,748 | B2 | 4/2005 | Manthorpe et al. |
| 8,722,063 | B2 | 5/2014 | Guerrero, Jr. et al. |
| 2011/0245096 | A1 | 10/2011 | Aggarwal et al. |
| 2013/0064843 | A1 | 3/2013 | Brusic et al. |
| 2013/0273095 | A1 | 10/2013 | Rodriguez Mallon et al. |
| 2016/0051649 | A1 | 2/2016 | Schetters et al. |

FOREIGN PATENT DOCUMENTS

| WO | WO 88/003929 | 6/1988 |
|---|---|---|
| WO | WO 90/002809 | 3/1990 |
| WO | WO 92/001047 | 1/1992 |
| WO | WO 92/009690 | 6/1992 |
| WO | WO 92/015679 | 9/1992 |
| WO | WO 92/018619 | 10/1992 |
| WO | WO 92/020791 | 11/1992 |
| WO | WO 93/001288 | 1/1993 |
| WO | WO 95/004827 | 2/1995 |
| WO | WO 2014/018724 | 1/2014 |
| WO | WO 2014/159052 | 10/2014 |
| WO | WO 2019/0153029 | 8/2019 |

OTHER PUBLICATIONS

Greenspan et al. (Nature Biotechnology 7: 936-937, 1999).*
Ellis (Vaccines, W.B. Saunders Company, Chapter 29, 1988, pp. 568-574).*
Boslego et al (Vaccines and Immunotherapy, 1991, Chapter 17).*
GenBank Accession No. ACI22374.1, Oct. 2008.
PCT International Search Report and Written Opinion issued in International Application No. PCT/AU2018/050080, dated May 1, 2018.
Sorgine et al., "A Heme-binding aspartic proteinase from the eggs of the hard tick *Boophilus microplus*," *The Journal of Biological Chemistry*, 275(37):28659-28665, 2000.
UniProtKB Accession No. A0A034WWI5, Jul. 2014.
UniProtKB Accession No. A0AI21ZAL2, May 2016.
UniProtKB Accession No. Q9GYX7, Mar. 2001.
Adams et al., "Highly Specific in Vivo Tumor Targeting by Monovalent and Divalent Forms of 741F8 Anti-c-erbB-2 Single-Chain Fvl," *Cancer Res.*, 53: 4026-4034, 1993.
Allen et al., "Induction of AIDS Virus-Specific CTL Activity in Fresh, Unstimulated Peripheral Blood Lymphocytes from Rhesus Macaques Vaccinated with a DNA Prime/Modified Vaccinia Virus Ankara Boost Regimen," *J. Immunol.*, 164(9): 4968-4978, 2000.

(Continued)

*Primary Examiner* — Robert A Zeman
(74) *Attorney, Agent, or Firm* — ParkerHighlander PLLC

(57) ABSTRACT

The present invention relates to immunogenic polypeptides, immunogenic fragments thereof and compositions comprising same, for use in eliciting an immune response in a subject to a tick. The invention also provides for methods of using said compositions and polypeptides.

13 Claims, 3 Drawing Sheets
Specification includes a Sequence Listing.

(56) References Cited

OTHER PUBLICATIONS

Altschul et al., "Gapped BLAST and PSI-BLAST: a new generation of protein database search programs," Nucl. Acids Res., 25(17): 3389-3402, 1997.
Arkin and Yourvan "An algorithm for protein engineering: Simulations of recursive ensemble mutagenesis," Proc. Natl. Acad. Sci. USA, 89: 7811-7815, 1992.
Barbas et al., "Assembly of combinatorial antibody libraries on phage surfaces: The gene III site," Proc.Natl. Acad. Sci USA, 88: 7978-7982, 1991.
Bateman et al., "The Pfam Protein Families Database," Nucleic Acids Res., 30: 276-280, 2002.
Bendtsen et al., "Improved Prediction of Signal Peptides: SignalP 3.0," J Mol Biol., 340: 783-95, 2004.
Burger et al., "Phylogenetic analysis of mitochondrial genome sequences indicates that the cattle tick, Rhipicephalus (Boophilus) microplus, contains a cryptic species," Mol Phylogenet Evol., 78: 241-253, 2014.
Chang et al., "Clinical Observations on Adoptive Immunotherapy with Vaccine-primed T-Lymphocytes Secondarily Sensitized to T\imor in Vitro 1," Cancer Res., 53: 1043-1050, 1993.
Clackson et al., "Making antibody fragments using phage display libraries," Nature, 352: 624-628, 1991.
Cumber et al., "Comparative stabilities in vitro and in vivo of a recombinant mouse antibody FvCys fragment and a bisFvCys conjugate," J. Immunol., 149: 120-126, 1992.
Cunha et al., "Calculation of the efficacy of vaccines against tick infestations on cattle†," Rev Bras Parasitol Vet. 2013;22(4):571-578, 2013.
Davies & Riechmann, "'Camelising' human antibody fragments: NMR studies on VH domains," (1994) FEBS Lett., 339: 285-290, 1994.
De la Fuente et al., "Vaccination against ticks (Boophilus spp.): the experience with the Bm86-based vaccine Gavac™," Gavac, Genet. Anal., 15: 143-148, 1999.
DeCastro, et al., "Sustainable tick and tickborne disease control in livestock improvement in developing countries," (1997) Vet. Parasitol., 71: 71-97, 1997.
Delgrave et al., "Recursive ensemble mutagenesis," Protein Engineering, 6: 327-331, 1993.
Ferber et al., "Role of arginine-tRNA in protein degradation by the ubiquitin pathway," Nature, 326: 808-811, 1987.
Fuchs et al., "Targeting Recombinant Antibodies to the Surface of Escherichia coli: Fusion to a Peptidoglycan Associated Lipoprotein," Bio/technology, 9: 1370-1372, 1991.
Garcia-Garcia et al., "Sequence variations in the Boophilus microplus Bm86 locus and implications for immunoprotection in cattle vaccinated with this antigen," Exp. App. Acar., 23: 883-895, 1999.
Garrad et al., "$F_{AB}$ Assembly and Enrichment in a Monovalent Phage Display System," Bio/Technology, 9: 1373-1377, 1991.
Ghoda et al., "Structural Elements of Ornithine Decarboxylase Required for Intracellular Degradation and Polyamine-Dependent Regulation," Mol. Cell Biol., 12: 2178-2185, 1992.
Giliman and Smith "Site-specific Mutagenesis Using Synthetic Oligodeoxyribonucleotide Primers: I. Optimum Conditions and Minimum Ologodeoxyribonucleotide Length," Gene, 8: 81-97, 1979.
Glockshuber et al., "A Comparison of Strategies To Stabilize Immunoglobulin Fv-Fragmentst," Biochem., 29(6): 1363-1367, 1990.
Glotzer et al., "Cyclin is degraded by the ubiquitin pathway," Nature, 349:132-138, 1991.
Gram et al., "In vitro selection and affinity maturation of antibodies from a naive combinatorial immunoglobulin library," Proc.Natl. Acad. Sci USA, 89: 3576-3580, 1992.
Griffths et al., "Human anti-self antibodies with high specificity from phage display libraries," EMBO J, 12: 725-734, 1993.
Guerrero et al., "BmiGI: A database of cDNAs expressed in Boophilus microplus, the tropical/southern cattle tick," Insect Biochem Mol Biol., 35: 585-95, 2005.

Hamers-Casterman et al., "Naturally occurring antibodies devoid of light chains," Nature, 363: 446-448, 1993.
Hawkins et al., "Selection of Phage Antibodies by Binding Affinity Mimicking Affinity Maturation," J Mol. Biol., 226:889-896, 1992.
Hoogenboom et al., "Multi-subunit proteins on the surface of filamentous phage: methodologies for displaying antibody (Fab) heavy and light chains," Nucleic Acid Res., 19: 4133-4137, 1991.
Huse et al., "Generation of a Large Combinatorial Library of Immunoglobulin Repertoire in Phage Lambda," Science, 246: 1275-1281, 1989.
Jung et al., "Distinct Response of Human B Cell Subpopulations in Recognition of an Innate Immune Signal, CpG DNA," J. Immunol., 169: 2368-73, 2002.
Kay et al., "Viral vectors for gene therapy: the art of turning infectious agents into vehicles of therapeutics," Nat. Med., 7(1): 33-40, 2001.
Keiler et al., "Role of a Peptide Tagging System in Degradation of Proteins Synthesized from Damaged Messenger RNA," Science, 271: 990-993, 1996.
King et al., "How Proteolysis Drives the Cell Cycle," Science 274: 1652-1659, 1996.
King et al., "Mutagenic Analysis of the Destruction Signal of Mitotic Cyclins and Structural Characterization of Ubiquitinated Intermediates," Mol. Biol. Cell, 7: 1343-1357, 1996.
Klinman et al., "CpG motifs present in bacterial DNA rapidly induce lymphocytes to secrete interleukin 6, interleukin 12, and interferon y," Proc. Natl Acad. Sci. U.S.A., 93: 2879-83, 1996.
Kostelny et al., "Formation of a bispecific antibody by the use of leucine zippers," J. Immunol. 148: 1547-1553, 1992.
Kreber et al., "Reliable cloning of functional antibody variable domains from hybridomas and spleen cell repertoires employing a reengineered phage display system," J. Immunol. Methods, 201(1): 35-55, 1997.
Ku & Schultz, "Alternate protein frameworks for molecular recognition," Proc. Natl. Acad. Sci. USA, 92: 652-6556, 1995.
Kunkel et al., "Rapid and efficient site-specific mutagenesis without phenotypic selection," Proc. Natl. Acad. Sci. USA, 82: 488-492, 1985.
Kunkel et al., "Rapid and Efficient Site-Specific Mutagenesis without Phenotypic Selection," Methods in Enzymol,, 154: 367-382, 1987.
Larsen et al., "Improved method for predicting linear B-cell epitopes," Immunome Res. 2:2, 2006.
Lew-Tabor et al., "Suppressive subtractive hybridization analysis of Rhipicephalus (Boophilus) microplus larval and adult transcript expression during attachment and feeding," Veterinary Parasitology, 167 (2-4): 304-320, 2010.
Lew-Tabor et al., "Rhipicephalus (Boophilus) microplus tick in vitro feeding methods for functional (dsRNA) and vaccine candidate (antibody) screening," Ticks and Tick Borne Diseases, 5: 500-510, 2014.
Lew-Tabor et al., "A review of reverse vaccinology approaches for the development of vaccines against ticks and tick borne diseases," Ticks and Tick Borne Diseases, 7: 573-585, 2016.
Li et al., "The N Terminus of Antizyme Promotes Degradation of Heterologous Proteins," Mol. Cell Biol., 14: 87-92, 1994.
Loeffler et al., "Analysis of Distribution of Tumor- and Preneoplasia-Infiltrating Lymphocytes Using Simultaneous Hoechst 33342 Labeling and Immunophenotypingl," Cytom., 13: 169-174, 1992.
Low et al., "Molecular characterisation of the tick Rhipicephalus microplus in Malaysia: new insights into the cryptic diversity and distinct genetic assemblages throughout the world," Parasites & Vectors, 8: 341, 2015.
Marchler-Bauer et al., "CDD: specific functional annotation with the Conserved Domain Database, " Nucleic Acids Res., 37: 205-10, 2009.
Meister et al., "Two novel 'T cell epitope prediction algorithms based on MHC-binding motifs; comparison of predicted and published epitopes from Mycobacterium tuberculosis and HIV protein sequences," Vaccine, 13: 581-591, 1995.
Okuda et al., "KEGG Atlas mapping for global analysis of metabolic pathways," Nucleic Acids Res., 36: W423-6, 2008.

(56) References Cited

OTHER PUBLICATIONS

Ordiz et al., "Glucose-induced inactivation of isocitrate lyase in *Saccharomyces cerevisiae* is mediated by the CAMP-dependent protein kinase catalytic subunits Tpk1 and Tpk2," *FEBS Lett.*, 385: 43-46, 1996.
Piper et al., "Peripheral cellular and humoral responses to infestation with the cattle tick *Rhipicephalus microplus* in Santa Gertrudis cattie," *Parasite Immunology*, 39: e12402, 2017.
Playford et al., "Review of research needs for cattle tick control—Phases I and II," Meat & Livestock Australia Ltd, 2005.
Provinciali et al., "Optimization of cytotoxic assay by target cell retention of the fluorescent dye carboxyfluorescein diacetate (CFDA) and comparison with conventional 51CR release assay," *J. Immunol. Meth.*, 155: 19-24, 1992.
Rand et al., "Cloning and expression of a protective antigen from the cattle tick *Boophilus microplus*," *Proc. Natl. Acad. Sci. USA*, 86: 9657-9661, 1989.
Reiter et al., "Stabilization of the Fv Fragments in Recombinant Immunotoxins by Disulfide Bonds Engineered into Conserved Framework Regions," *Cancer Res.*, 54: 2714-2718, 1994.
Reiter et al., "Antibody Engineering of Recombinant Fv Immuno toxins for Improved Targeting of Cancer: Disulfide-stabilized Fv Immunotoxins," *J. Biol. Chem.*, 269: 18327-18331, 1994.
Reiter et al., "Improved Binding and Antitumor Activity of a Recombinant Anti-erbB2 Immunotoxin by Disulfide Stabilization of the Fv Fragment," *Biochem.*, 33: 5451-5459, 1994.
Rice et al., "EMBOSS: The European Molecular Biology Open Software Suite," *Trends Genet*, 16: 267-277, 2000.
Rivoltini et al., "Phenotypic and functional analysis of lymphocytes infiltrating paediatric tumours, with a characterization of the tumour phenotype," *Cancer Immunol. Immunother.*, 34: 241-251, 1992.
Roberge et al., "A strategy for a convergent synthesis of N-linked glycopeptides on a solid support," (1995) *Science*, 269: 202, 1995.
Roberts et al., "Generation of an antibody with enhanced affinity and specificity for its antigen by protein engineering," *Nature*, 328: 731-734, 1987.
Rogers et al., "Amino Acid Sequences Common to Rapidly Degraded Proteins: The PEST Hypothesis," *Science*, 234(4774): 364-368, 1986.
Sadis et al., "Synthetic Signals for Ubiquitin-Dependent Proteolysis," *Mol. Cell Biol.*, 15(25): 4086-4094, 1995.
Stajich et al., "The Bioperl Toolkit: Perl Modules for the Life Sciences," *Genome Res*, 12: 1611-1618, 2002.
Sturniolo et al., "Generation of tissue-specific and promiscuous HLA ligand databases using DNA microarrays and virtual HLA class II matrices," *Nat. Biotechnol.*, 17: 555-61, 1999.
Tatusov et al., "The COG database: an updated version includes eukaryotes," *BMC Bioinformatics*, 4: 41, 2003.
Valle R et al., "Comparative microarray analysis of Rhipicephalus (Boophilus) microplus expression profiles of larvae pre-attachment and feeding adult female stages on *Bos indicus* and *Bos taurus* cattle," *BMC Genomics*, 11: 43, 2010.
Van Mering et al., "STRING: a database of predicted functional associations between proteins," *Nucleic Acids Res.*, 35: 0358-362, 2006.
Vigna and Naldini "Lentiviral vectors: excellent tools for experimental gene transfer and promising candidates for gene therapy," *J. Gene Med.*, 2(5): 308-316, 2000.
Vollenweider and Groseurth "Comparison of four DNA staining fluorescence dyes for measuring cell proliferation of lymphokine-activated killer (LAK) cells," *J. Immunol. Meth.*, 149: 133-135, 1992.
Wagner "Interactions between bacterial CpG-DNA and TLR9 bridge innate and adaptive immunity," *Curr. Opin. Microbial.*, 5: 62-69, 2002.
Walther and Stein "Viral Vectors for Gene Transfer: A Review of Their Use in the Treatment of Human Diseases," *Drugs*, 60(2): 249-271, 2000.
Wang et al., "Global comparative analysis of ESTs from the southern cattle tick, *Rhipicephalus (Boophilus) microplus*," *BMC Genomics*, 8: 368-382, 2007.
Ward et al., "Binding activities of a repertoire of single immunoglobulin variable domains secreted from *Escherichia coli*," *Nature*, 341: 544-546, 1989.
Webber et al., "Preparation and characterization of a disulfide-stabilized Fv fragment of the anti-Tac antibody: Comparison with its single-chain analog" (1995) *Mol. Immunol.*, 32: 249-258, 1995.
Winter and Milstein "Man-made antibodies," *Nature*, 349: 293, 1991.
Wu and Ataai "Production of viral vectors for gene therapy applications," *Curr. Opin. Biotechnol.*, 11(2): 205-208, 2000.
Yaglom et al., "p34Cdc28-Mediated Control of Cln3 Cyclin Degradation," *Mol. Cell Biol.*, 15: 731-741, 1995.
Yaglom et al., "The Molecular Chaperone Ydj1 Is Required for the p34CDC28-Dependent Phosphorylation of the Cyclin Cln3 That Signals Its Degradation," *Mol. Cell Biol.*, 16: 3679-3684, 1996.
Almazan et al., "Identification and characterization of Rhipicephalus (Boophilus) microplus andidate protective antigens for the control of cattle tick infestations," *Parasitology Research*, 106:471-479, 2010.
Barnard, Annette-Christi, "A reverse genetics approach to evaluate Metzincins as anti-*Rhipicephalus microplus* tick vaccine candidates," Ph.D. Thesis. University of Pretoria, Mar. 2013.
De Rose et al., "Bm86 antigen induces a protective immune response against Boophilus microplus following DNA and protein vaccination in sheep," *Veterinary Immunology and Immunopathology*, 71:151-160, 1999.
PCT International Preliminary Report on Patentability issued in International Application No. PCT/AU2018/050081, dated Apr. 23, 2018.
PCT International Preliminary Report on Patentability issued in International Application No. PCT/AU2018/050080, dated Aug. 6, 2019.

\* cited by examiner

SEQUENCE LISTING

```
<160> NUMBER OF SEQ ID NOS: 107

<210> SEQ ID NO 1
<211> LENGTH: 558
<212> TYPE: PRT
<213> ORGANISM: Rhipicephalus microplus

<400> SEQUENCE: 1

Met Lys Pro Val Ser Leu Phe Leu Leu Ala Val Tyr Leu Leu Val Val
1               5                   10                  15

Gln Ala Glu Asp Leu Ala Gly Arg Thr Phe Gly Phe Gly Gln Ser His
            20                  25                  30

Pro Ala Leu Gln His Ala His His Gly His Gly Met Ser Pro Gln Thr
        35                  40                  45

Gln Val His Phe Asn His Val Leu Pro Pro His His Gly Ser Asp Thr
    50                  55                  60

Gly His Ala His Gly His Ser His His Gly His Ala Ala Ser Gly Asn
65                  70                  75                  80

His His Gln Val Val His Gly His Gln His Asn His Gln Gln Ser Val
                85                  90                  95

Gln Pro Gly Ala Ala Thr Glu Pro Ala Ala Ser Asn Val His Thr Val
            100                 105                 110

Pro Val Leu Met Cys Arg Val Val Lys Val Pro Val Ser Thr Pro Ala
        115                 120                 125
```

```
Pro Thr Val Pro Pro Arg Ser Asp Ser Ser Ser Gly Thr His Gly
    130                 135                 140

Val Gly Ser His Ile Ala His Ser Ile Ser His Val Phe Gly Thr Val
145             150                 155                 160

Val Asn Pro Val Val Ala Leu Leu Lys Asn Ala Ser Val Trp Leu Asn
            165                 170                 175

Arg Thr Thr His Gly Asp Asn Gly Ala Ala Ala His His His Asn His
        180                 185                 190

His His Gln Ser Ala Val Pro His Ser Leu Val Leu Gln Lys Asn Ser
        195                 200                 205

Ile Arg Pro Ala Ser Val Thr Ser Ala Pro Thr Ala Pro Ser Pro Ala
210                 215                 220

Pro Thr Val Ala Ser Thr Val Pro Ser Ala Thr Thr Arg Ser Arg Leu
225                 230                 235                 240

Thr Met Val Pro Pro Phe Ala Pro Thr Val Leu Pro Thr Val Gly Ala
                245                 250                 255

Ala Ala Pro Thr Val Arg Gly Pro Val Pro Arg Val Gly Thr Phe Pro
            260                 265                 270

Val Pro Ala Thr Thr Val Ala Ser Ala Asp Phe Pro Thr Ser Ala Pro
            275                 280                 285

Ala Asn Val Ser Ser Thr Leu Pro Val Leu Ile Pro Val Thr Asp Ser
290                 295                 300

Ser Thr Ser Thr Leu Ser Thr Val Val Ser Ser Thr Leu Pro Ala Ala
305                 310                 315                 320

His Val Thr Thr Leu Ala Ala Ser Thr Thr Thr Ala Pro Asp Ser Leu
                325                 330                 335

Asn Phe Arg Ala Ile Pro Phe Thr Pro Thr Ala Thr Ser Ser Glu Leu
            340                 345                 350

Pro Ala Thr Thr Pro Val Asp Ala Thr Ser Thr Ala Ala Val Ser Val
            355                 360                 365

Glu Thr Thr Ala Glu Phe Leu Asp Pro Thr Val Val Thr Thr Gln Asn
370                 375                 380

Pro Gln Pro Ala Asp Val Ser Thr Thr His Phe Pro Ser Thr Ala Ser
385                 390                 395                 400

Ile Glu Thr Pro Arg Arg Gly Val Thr Leu Asp Pro Arg Ala Gly Pro
            405                 410                 415

Phe Thr Leu Leu Val Thr Ser Pro Lys Val Pro Ala Thr Gly Leu Pro
            420                 425                 430

Leu Gln Glu Gln Ser Asn Ala Ala Thr Ser Pro Pro Ser Thr Leu Pro
        435                 440                 445

Val Glu Pro Arg Ala Leu Thr Thr Ser Thr Pro Glu Ala Thr Thr Ser
450                 455                 460

Leu Pro Val Ser Thr Asp Ala Pro Ser Leu Pro Leu Ala Gly Thr Ile
465                 470                 475                 480

Leu Pro Pro Thr Val Gly Thr Thr Phe Val Arg Met Ser Thr Val Val
                485                 490                 495

Ser Ile Asp Pro Val Ala Asn Arg Val Pro Pro Val Thr Thr Thr Ala
            500                 505                 510

Ser Gly Thr Leu Thr Pro Val Pro Leu Ser Thr Ala Lys Leu Pro Val
            515                 520                 525

Pro Leu Leu Ser Thr Thr Leu Gly Ser Thr Thr Ser Pro Leu Ala Asn
530                 535                 540

Phe Thr Phe Phe Gly Val Arg Ser Val Arg Pro Lys Thr Arg
```

```
                     545                 550                 555

<210> SEQ ID NO 2
<211> LENGTH: 276
<212> TYPE: PRT
<213> ORGANISM: Rhipicephalus australis

<400> SEQUENCE: 2

Met Lys Pro Val Ser Leu Phe Leu Leu Ala Val Cys Leu Leu Val Val
1               5                   10                  15

Gln Ala Glu Tyr Phe Ala Gly Arg Thr Phe Gly Phe Gly His Ser His
            20                  25                  30

Pro Ala Leu Gln His Ala His His Gly His Gly Met Ser Ser Gln Ala
        35                  40                  45

Gln Gly His Ile Asn His Val Leu Pro Pro His Arg Gly Ser His Ala
    50                  55                  60

Gly His Ala His Gly His Ser His His Gly Gln Val Pro Asn Ala His
65                  70                  75                  80

Gln His Gln Leu Val His Val His Gln His Asn His Gln Gln Ser Ala
                85                  90                  95

Gln Pro Ser Ala Ala Thr Ala Pro Ala Ala Ser Asn Val Ser Thr Val
            100                 105                 110

Pro Val Leu Met Cys Arg Val Val Lys Val Pro Val Asn Thr Pro Ala
        115                 120                 125

Pro Thr Val Pro Pro Arg Ser Asp Ser Ser Ser Gly Thr His Val
    130                 135                 140

Gly Ser His Ile Ala His Ser Ile Ser His Val Phe Gly Thr Val Val
145                 150                 155                 160

Asn Pro Val Met Ala Leu Leu Lys Asn Ala Ser Val Trp Leu Asn Arg
                165                 170                 175

Thr Ala His Glu Asp Asn Gly Ala Ala Ala His His His Asn His His
            180                 185                 190

His Gln Ser Ala Val Pro His Ser Leu Val Leu Gln Lys Lys Val Gln
        195                 200                 205

Val Ile Gly Gln Arg Asp Asn Ile Pro Asn Gly Pro Ala Ser Ile Ser
    210                 215                 220

Thr Arg Pro Ala Ser Val Thr Ser Ala Pro Thr Thr Pro Ser Pro Ala
225                 230                 235                 240

Pro Thr Val Ala Ser Thr Val Pro Ser Ala Ala Thr Arg Ser Arg Leu
                245                 250                 255

Thr Met Val Pro Pro Phe Ala Pro Thr Val Leu Pro Thr Val Val Pro
            260                 265                 270

Arg His Leu Leu
        275

<210> SEQ ID NO 3
<211> LENGTH: 373
<212> TYPE: PRT
<213> ORGANISM: Rhipicephalus microplus

<400> SEQUENCE: 3

Met Glu Leu Gln Ala Thr Ile Leu Leu Val Phe Thr Leu Ile Val Gly
1               5                   10                  15

Ser Ser Ala Glu Phe Ala Leu Gln Leu Gly Trp His Asp Pro Asn Val
            20                  25                  30

Thr Glu Ile Arg Gly Arg Ala Leu Gly Asp Pro Ile Pro Ile Ile Leu
```

```
            35                  40                  45
Thr Asn Tyr Asn Asn Met Gln Phe Tyr Gly Ile Ile Thr Ile Gly Thr
        50                  55                  60

Pro Pro Gln Ser Phe Lys Leu Leu Met Asp Thr Gly Ser Ser Asn Phe
 65                  70                  75                  80

Trp Val Pro Ser Ile Asn Cys Asp Gln Ser Met Ala Cys Arg Asp His
                85                  90                  95

Ala Lys Tyr Asp Ser Ser Lys Ser Ser Thr Phe Thr Lys Ser Gly Arg
            100                 105                 110

Tyr Ile Arg Ile Arg Tyr Ser Gly Gly Val Val Arg Gly Ile Thr Ser
        115                 120                 125

Ile Asp Asn Val Gly Val Gly Pro Ala Thr Val Thr Gln Tyr Lys Phe
    130                 135                 140

Ala Glu Met Asp His Ser Asp Gly Lys Leu Phe Arg Asn Ala Lys Tyr
145                 150                 155                 160

Asp Gly Ile Phe Gly Leu Ala Phe Pro Ser Ile Ser Gln Asn Asn Gln
                165                 170                 175

Leu Pro Leu Phe Asp Ala Met Val Lys Gln Gly Val Val Arg Gln Ala
            180                 185                 190

Val Phe Ser Leu Tyr Leu Ser Lys Gln Pro Ser Glu Gln Asn Gly Gly
        195                 200                 205

Glu Ile Tyr Phe Gly Gly Ile Asn Ala Gln Arg Tyr Thr Gly Ala Ile
    210                 215                 220

His Tyr Val Pro Val Ser Gln Ala Ala His Trp Gln Val Val Met Asp
225                 230                 235                 240

Asn Ile Asn Val Gln Gly Thr Thr Leu Cys Val Gly Cys Pro Thr
                245                 250                 255

Val Val Asp Ser Gly Thr Ser Phe Leu Ser Gly Pro Ser Ala Asp Val
            260                 265                 270

Glu Thr Leu Asn Arg Val Ile Gly Ala Thr Lys Thr Pro Ala Gly Tyr
        275                 280                 285

Phe Glu Val Asn Cys Ala Thr Ile Ala Ser Leu Pro Pro Ile Thr Phe
    290                 295                 300

Asn Leu Asn Gly Lys Ser Phe Pro Leu Gln Gly Glu Ala Tyr Thr Ile
305                 310                 315                 320

Arg Ile Pro Leu Thr Thr Gly Gly Glu Gln Cys Phe Thr Arg Ile Ser
                325                 330                 335

Glu Ser Asp Ala Ser Gly Thr Asn Leu Trp Ile Leu Gly Ala Val Phe
            340                 345                 350

Thr Gln Thr Tyr Tyr Thr Val Phe Asp Lys Val Gln Asn Arg Val Gly
        355                 360                 365

Phe Ala Thr Ala Val
    370

<210> SEQ ID NO 4
<211> LENGTH: 320
<212> TYPE: PRT
<213> ORGANISM: Rhipicephalus australis

<400> SEQUENCE: 4

Met Glu Leu Gln Ala Thr Ile Leu Leu Val Phe Thr Leu Ile Val Gly
 1               5                  10                  15

Ser Ser Ala Glu Phe Ala Leu Gln Leu Gly Trp His Asp Pro Asn Val
                20                  25                  30
```

-continued

Thr Glu Ile Arg Gly Arg Ala Leu Gly Asp Pro Ile Pro Ile Ile Leu
         35                  40                  45

Thr Asn Tyr Asn Asn Met Gln Phe Tyr Gly Ile Thr Ile Gly Thr
 50                  55                  60

Pro Pro Gln Ser Phe Lys Leu Leu Met Asp Thr Gly Ser Ser Asn Phe
 65                  70                  75                  80

Trp Val Pro Ser Ile Asn Cys Asp Gln Ser Met Ala Cys Arg Asp His
                 85                  90                  95

Ala Lys Tyr Asp Ser Ser Lys Ser Ser Thr Phe Thr Lys Ser Gly Arg
                100                 105                 110

Tyr Ile Arg Ile Arg Tyr Ser Gly Gly Val Val Arg Gly Ile Thr Ser
                115                 120                 125

Ile Asp Asn Val Gly Val Gly Pro Ala Thr Val Thr Gln Tyr Lys Phe
130                 135                 140

Ala Glu Met Asp His Ser Asp Gly Lys Leu Phe Arg Asn Ala Lys Tyr
145                 150                 155                 160

Asp Gly Ile Phe Gly Leu Ala Phe Pro Ser Ile Ser Gln Asn Asn Gln
                165                 170                 175

Leu Pro Leu Phe Asp Ala Met Val Lys Gln Gly Val Val Arg Gln Ala
                180                 185                 190

Val Phe Ser Leu Tyr Leu Ser Lys Gln Pro Ser Glu Gln Asn Gly Gly
                195                 200                 205

Glu Ile Tyr Phe Gly Gly Ile Asn Ala Gln Arg Tyr Thr Gly Ala Ile
                210                 215                 220

His Tyr Val Pro Val Ser Gln Ala Ala His Trp Gln Val Val Met Asp
225                 230                 235                 240

Asn Ile Asn Val Gln Gly Thr Thr Leu Cys Val Gly Cys Pro Thr
                245                 250                 255

Val Val Asp Ser Gly Thr Ser Phe Leu Ser Gly Pro Ser Ala Asp Val
                260                 265                 270

Glu Thr Leu Asn Arg Val Ile Gly Ala Thr Lys Thr Ala Ala Gly Tyr
                275                 280                 285

Phe Glu Val Asn Cys Ala Thr Ile Ser Ser Leu Pro Pro Ile Thr Phe
                290                 295                 300

Asn Leu Asn Gly Lys Ser Phe Pro Leu Gln Gly Glu Pro Thr Arg Ser
305                 310                 315                 320

<210> SEQ ID NO 5
<211> LENGTH: 375
<212> TYPE: PRT
<213> ORGANISM: Rhipicephalus microplus

<400> SEQUENCE: 5

Met Ser Pro Leu Gly Ile Thr Leu Leu Leu Gly Leu Leu Gly Val Ser
 1               5                  10                  15

Thr Ala Gln Phe Ser Ile Ser Leu Trp Arg Asn Lys Thr Asp Phe Glu
                20                  25                  30

Pro Arg Arg Arg Thr Trp Leu Asp Ala Ala Val Ile Pro Glu Glu
                35                  40                  45

Leu Glu Asn Glu Lys Asn Leu His Tyr Tyr Gly Leu Ile Gly Leu Gly
                50                  55                  60

Thr Pro Pro Gln Arg Phe Lys Val Ile Phe Asp Thr Gly Ser Ala Asn
 65                  70                  75                  80

Leu Trp Val Pro Ser Val Lys Cys Pro Asp Thr Glu Asp Gly Cys Lys
                85                  90                  95

Asp Lys Lys Lys Tyr Asp Ser Ser Lys Ser Ser Thr Tyr Lys Ala Asp
            100                 105                 110

Gly Arg Lys Phe Arg Ile Glu Tyr Gly Ser Gly Ile Val Glu Gly Ile
        115                 120                 125

Tyr Ser Thr Asp Val Leu Thr Ile Gly Asn Gly Lys Val Asn Pro Gln
    130                 135                 140

Thr Phe Ala Glu Ala Thr Lys Ala Gln Gly Ser Ile Phe Lys Ala Ala
145                 150                 155                 160

Gln Phe Asp Gly Leu Leu Gly Leu Gly Tyr Pro Ala Leu Ala Glu Asp
                165                 170                 175

Asn Val Val Pro Val Phe Asp Asn Met Met Lys Gln Asn Leu Leu Pro
            180                 185                 190

Lys Pro Val Phe Ser Val Tyr Leu Asn Arg Asp Pro Lys Ala Thr Pro
        195                 200                 205

Gly Gly Glu Ile Tyr Phe Gly Gly Ile Asn Ser Asn Arg Tyr Thr Gly
    210                 215                 220

Ser Ile Thr Tyr Thr Ser Val Thr Lys Lys Ser Tyr Trp Gln Phe Lys
225                 230                 235                 240

Met Gln Gly Met Gln Val Lys Lys Asp Lys Thr Phe Cys Val Gly Gly
                245                 250                 255

Cys Asp Ala Val Met Asp Thr Gly Ser Ser Phe Ile Glu Gly Pro Arg
            260                 265                 270

Asp Glu Ile Glu Arg Leu Asn Lys Tyr Leu Arg Ala Thr Glu Glu Pro
        275                 280                 285

Ala Gly Asp Trp Arg Val Lys Cys Ala Asn Ile Pro Lys Met Pro Lys
    290                 295                 300

Ile Ser Phe Thr Ile Gly Gly Arg Glu Phe Thr Met Thr Ala Asp Gln
305                 310                 315                 320

Tyr Ile Ile Gln Val Gln Gly Ser Lys Lys Val Lys Cys Tyr Ser Gly
                325                 330                 335

Phe Ala Val Ser Asp Thr Pro Thr Lys Lys Phe Trp Val Ile Gly Gln
            340                 345                 350

Val Phe Ile Gly Ser Phe Tyr Thr Ile Phe Asp Arg Gly Ser Asp Arg
        355                 360                 365

Ile Gly Phe Ala Thr Val Ala
    370                 375

<210> SEQ ID NO 6
<211> LENGTH: 287
<212> TYPE: PRT
<213> ORGANISM: Rhipicephalus australis

<400> SEQUENCE: 6

Met Ser Pro Leu Gly Ile Thr Leu Leu Leu Gly Leu Leu Gly Val Ser
1               5                   10                  15

Thr Ala Gln Phe Ser Ile Ser Leu Trp Arg Asn Lys Thr Asp Phe Glu
            20                  25                  30

Pro Arg Arg Arg Thr Trp Leu Asp Ala Ala Val Ile Pro Glu Glu
        35                  40                  45

Leu Glu Asn Glu Lys Asn Leu His Tyr Tyr Gly Leu Ile Gly Leu Gly
    50                  55                  60

Thr Pro Pro Gln Ser Phe Lys Val Ile Phe Asp Thr Gly Ser Ala Asn
65                  70                  75                  80

Leu Trp Val Pro Ser Val Lys Cys Pro Asp Thr Glu Asp Gly Cys Lys

```
                    85                  90                  95
Asp Lys Lys Lys Tyr Asp Ser Ser Lys Ser Ser Thr Tyr Lys Ala Asp
            100                 105                 110

Gly Arg Lys Phe Arg Ile Glu Tyr Gly Ser Gly Ile Val Glu Gly Ile
            115                 120                 125

Tyr Ser Thr Asp Val Leu Thr Ile Gly Asn Gly Lys Val Asn Pro Gln
            130                 135                 140

Thr Phe Ala Glu Ala Thr Lys Ala Gln Gly Ser Ile Phe Lys Ala Ala
145                 150                 155                 160

Lys Phe Asp Gly Leu Leu Gly Leu Gly Tyr Pro Ala Leu Ala Glu Asp
            165                 170                 175

Asn Val Val Pro Val Phe Asp Asn Met Met Lys Gln Asn Leu Leu Pro
            180                 185                 190

Lys Pro Val Phe Ser Val Tyr Leu Asn Arg Asp Pro Lys Ala Thr Pro
            195                 200                 205

Gly Gly Glu Ile Tyr Phe Gly Gly Ile Asn Ser Asn Arg Tyr Thr Gly
            210                 215                 220

Ser Ile Thr Tyr Thr Ser Val Thr Lys Lys Ser Tyr Trp Gln Phe Lys
225                 230                 235                 240

Met Gln Gly Met Gln Val Lys Lys Asp Lys Thr Phe Cys Val Gly Gly
            245                 250                 255

Cys Asp Ala Val Met Asp Thr Gly Ser Ser Phe Ile Glu Gly Pro Arg
            260                 265                 270

Asp Glu Ile Glu Arg Leu Asn Lys Tyr Leu Arg Ala Thr Glu Glu
            275                 280                 285

<210> SEQ ID NO 7
<211> LENGTH: 221
<212> TYPE: PRT
<213> ORGANISM: Rhipicephalus microplus

<400> SEQUENCE: 7

Met Lys Phe Phe Ala Thr Val Thr Leu Leu Ala Leu Val Ala Ser Ala
1               5                   10                  15

Ala Phe Ala Glu Glu Asp Ala Lys Lys Val Lys Lys Glu Asp Lys
            20                  25                  30

Lys Asp Val Glu Gly Arg Gly Gly Phe Leu Gly Gly Pro Gly Phe
            35                  40                  45

Gly Val Gly Val Val Pro Gly Val Gly Ser Pro Gly Val Val Gly
        50                  55                  60

Pro Gly Val Val Ala Asn Pro Ala Leu Val Gly Ala Gly Val Gly His
65                  70                  75                  80

Gly Val Gly His Gly Val Gly His Gly Val Gly Leu Gly Ala Val Gly
            85                  90                  95

Val Gly His Gly Val Gly Pro Gly Val Gly Leu Gly Gly Val Gly Val
            100                 105                 110

Gly His Gly Gly Gly Phe Gln Thr Gly Phe Gly Thr Ser Thr Gly Ala
            115                 120                 125

Gln Gln Ala Gly Phe Gln Arg Gly Ala Ala Gly His Gln Gln Gly Ser
            130                 135                 140

Gly Ala Phe Thr Gly Gly Ser Ala His Arg Thr Val Asn Ala Phe Ser
145                 150                 155                 160

Asn Asn Lys Gly Tyr Asp His Lys Thr Gly Phe Ser Ala Ser Asp Ser
            165                 170                 175
```

-continued

Lys Thr Phe Gly Ala Gly Gln Gln Gln Gly Ser Ala Gly Phe Gln Gly
180 185 190

Gly Ala Ala Gly His Gln Ala Gly Phe Gly Gln Ser Ser His Gly His
195 200 205

Thr Thr Gly Val Gly His Ala Gly Val Gly Val Val Gly
210 215 220

<210> SEQ ID NO 8
<211> LENGTH: 216
<212> TYPE: PRT
<213> ORGANISM: Rhipicephalus australis

<400> SEQUENCE: 8

Met Lys Phe Phe Ala Thr Val Thr Leu Leu Ala Leu Val Ala Ser Ala
1 5 10 15

Thr Phe Ala Glu Glu Gly Pro Lys Lys Ala Glu Lys Lys Glu Asp Lys
20 25 30

Lys Asp Ile Glu Gly Arg Gly Gly Phe Leu Gly Gly Gly Pro Gly Tyr
35 40 45

Gly Val Gly Val Val Pro Gly Val Val Gly Ser Pro Gly Val Val Gly
50 55 60

Pro Gly Val Val Ala Asn Pro Ala Leu Val Gly Ala Gly Leu Gly His
65 70 75 80

Gly Val Gly Leu Gly Ala Val Gly Val Gly His Gly Val Gly His Gly
85 90 95

Val Ser Pro Gly Val Gly Leu Gly Gly Val Gly Val Gly Gln Gly Gly
100 105 110

Gly Phe Gln Thr Gly Phe Gly Thr Ser Thr Gly Ala Gln Gln Ala Gly
115 120 125

Phe Gln Arg Gly Ala Ala Gly His Gln Gln Gly Ser Gly Ala Phe Thr
130 135 140

Gly Gly Ser Ala His Arg Thr Val Asn Ala Phe Ser Asn Lys Gln Gly
145 150 155 160

Tyr Asp His Lys Thr Gly Phe Ser Ala Ser Asp Ser Lys Thr Phe Gly
165 170 175

Ala Gly Gln Gln Gln Gly Ser Ala Gly Phe Gln Gly Gly Ala Ala Gly
180 185 190

His Gln Ala Gly Phe Gly Gln Ser Ser His Gly Gln Thr Ser Gly Val
195 200 205

Gly His Ala Gly Val Gly Val Val
210 215

<210> SEQ ID NO 9
<211> LENGTH: 320
<212> TYPE: PRT
<213> ORGANISM: Rhipicephalus microplus

<400> SEQUENCE: 9

Met Leu Ser Gln Arg Thr Cys Val Leu Leu Thr Ala Leu Leu Val Val
1 5 10 15

Cys Arg Ile Asn Ser Ala Leu Gly Ser Gly Leu Asn Ser Thr Val Cys
20 25 30

Asn Gly Leu Cys Leu Tyr Ser Val Asp Ala Asn Leu Phe Cys Glu Val
35 40 45

Ala Phe Val Ala Pro Pro Cys Ser Thr Lys Arg Gln Leu Cys Cys Thr
50 55 60

Glu Ile Arg Ala Ile Glu Ser Leu Ala Arg Val Lys Glu Asp Thr Ala
65                  70                  75                  80

Val Met Asp Asn Val Trp Ser Ala Arg Ala Asn Asn Asn Gln Asp
            85                  90                  95

Ser Met Arg Gln Asp Arg Ser Met Tyr Thr Asp Leu Leu Arg Leu Ile
            100                 105                 110

Val Ile Gln Ala Leu Arg Thr Ala Ile Ser Ser Glu Tyr Lys Ala Ile
            115                 120                 125

Lys Glu Lys Ser Met Pro Ala Thr Ala Ile Ser Thr Thr Thr Thr Ala
    130                 135                 140

Gln Tyr Asp Pro Thr Trp Pro Glu Glu Asn Asp Arg Phe Lys Thr Phe
145                 150                 155                 160

Lys Pro Ala Tyr Ala Phe Lys Lys Thr Ser Ser Thr Pro Ser Ala Val
                165                 170                 175

Leu Glu Pro Pro Gln Ser Phe Thr Val Thr Ala Pro Ser Gln Asp Pro
            180                 185                 190

Pro Leu Leu Asp Ala Ser Ser Ser Gly Ser Ser Thr Leu Ala Pro Leu
    195                 200                 205

Ala Asp Ser Ala Pro Pro Thr Val Ser Thr Ser Val Ser Ser Asp Ala
210                 215                 220

Glu Thr Thr Met Glu Lys Leu Leu Tyr Pro Cys Pro Gly Asn Cys Val
225                 230                 235                 240

Pro Thr Phe Leu Thr Trp Phe Cys Asp Ala Thr Asn Ser Asp Tyr Glu
                245                 250                 255

Cys Ser Ser Gly Arg Val Cys Cys Met Pro Ile Thr Thr Thr Thr Pro
            260                 265                 270

Ala Glu Asp Val Val Pro Glu Cys Pro Gly Thr Cys Ile Pro Pro Ala
    275                 280                 285

Ile Phe Gly Leu Cys Lys Arg Pro Ala Arg Leu Ile Leu Lys Thr Thr
290                 295                 300

Thr Cys Gly Arg Asp Leu Ile Cys Cys Thr Glu Thr Pro Met Leu Leu
305                 310                 315                 320

<210> SEQ ID NO 10
<211> LENGTH: 230
<212> TYPE: PRT
<213> ORGANISM: Rhipicephalus microplus

<400> SEQUENCE: 10

Met His Cys Asp Tyr Val Leu Trp Asn Val Val Leu Phe Val Val Met
1               5                   10                  15

Val Ala Thr Ser Thr Ala Gln Lys Pro Cys Glu Gly Gly Gly Glu Lys
            20                  25                  30

Asn Cys Thr Gly Lys Glu Lys Trp Cys Leu Val Asp Glu Asn Gly Gly
        35                  40                  45

Val His Glu Lys Cys Arg Asp Leu Asp Cys Ser Phe Ser Arg Phe Ser
    50                  55                  60

Cys Trp Phe Gln Cys Gln Gly Asp Thr Thr Leu Ala Cys His Lys Ser
65                  70                  75                  80

Pro Thr Asp Asp Gln Cys Ile Cys Ser Cys Val Lys Asn Phe Cys Asp
                85                  90                  95

Arg Asn Glu Gly Gln Lys Cys Ser Gly Lys Thr Lys Trp Cys Phe Asn
            100                 105                 110

Glu Thr Ala Gly Phe Thr Glu Trp Cys Gly Glu Ser Gly Cys Asp Ala
        115                 120                 125

Ser Lys Ser His Trp Lys Val Cys Lys Thr Pro Gly Thr Glu Met Ser
130                 135                 140

Cys Glu Lys Ala Ser Asp Ser Asp Ala Cys His Cys Thr Cys Val Glu
145                 150                 155                 160

Arg Val Cys Ser Asn Gln Gln Gly Asn Arg Cys Thr Ser Asn Lys Met
                165                 170                 175

Lys Trp Cys Met Ile Ser Asp Lys Gly His Tyr Thr Asp Thr Cys Asn
            180                 185                 190

Asp Arg Asn Cys His Pro Ser Thr Leu Pro Trp Lys Ile Cys Tyr Arg
            195                 200                 205

Arg Asp Tyr Lys Pro Ser Cys Arg Lys Thr Thr Leu Gly Thr Cys Leu
210                 215                 220

Cys Thr Cys Val Lys Gly
225                 230

<210> SEQ ID NO 11
<211> LENGTH: 230
<212> TYPE: PRT
<213> ORGANISM: Rhipicephalus australis

<400> SEQUENCE: 11

Met His Ser Asp Tyr Val Leu Trp Asn Val Val Leu Phe Val Val Met
1               5                   10                  15

Val Ala Thr Ser Thr Ala Gln Lys Pro Cys Glu Gly Gly Gly Glu Lys
                20                  25                  30

Asn Cys Thr Gly Lys Glu Lys Trp Cys Leu Val Asp Glu Asn Gly Gly
            35                  40                  45

Val His Glu Lys Cys Arg Asp Leu Asp Cys Ser Ser Ser Arg Phe Ser
        50                  55                  60

Cys Trp Phe Gln Cys Glu Gly Asp Thr Thr Leu Ala Cys His Lys Ser
65                  70                  75                  80

Pro Thr Asp Asp Ile Cys Ile Cys Ser Cys Val Lys Asn Phe Cys Asp
                85                  90                  95

Arg Asn Glu Gly Gln Lys Cys Ser Gly Lys Thr Lys Trp Cys Phe Asn
            100                 105                 110

Glu Thr Ala Gly Phe Thr Glu Met Cys Gly Glu Ser Gly Cys Asp Ala
        115                 120                 125

Ser Lys Ser His Trp Lys Val Cys Lys Thr Pro Gly Thr Glu Met Ser
130                 135                 140

Cys Glu Lys Ala Ser Asp Ser Asp Ala Cys His Cys Thr Cys Val Glu
145                 150                 155                 160

Arg Val Cys Ser Asn Gln Gln Gly Asn Arg Cys Thr Ser Asn Lys Met
                165                 170                 175

Lys Trp Cys Ile Ile Ser Asp Lys Gly Arg Tyr Thr Asp Ser Cys Asn
            180                 185                 190

Asp Arg Asn Cys His Pro Ser Thr Leu Pro Trp Lys Ile Cys Tyr Arg
            195                 200                 205

Arg Asp Tyr Lys Pro Ser Cys Arg Lys Thr Thr Leu Gly Thr Cys Leu
210                 215                 220

Cys Thr Cys Val Lys Gly
225                 230

<210> SEQ ID NO 12
<211> LENGTH: 180
<212> TYPE: PRT

<213> ORGANISM: Rhipicephalus australis

<400> SEQUENCE: 12

Met Leu Arg Gly Ala Leu Ala Ala Ile Leu Leu Leu Ile Ser Ser Asp
1               5                   10                  15

Leu Met Ile His Thr Ala Gly Leu Asp Ile Lys Gln Phe Val Arg Arg
            20                  25                  30

Arg Glu Arg Ile Trp Thr Tyr Lys Thr Thr Arg Arg Asp Asn Val Gln
        35                  40                  45

Cys Glu Val Asp Lys Leu Leu Tyr Ser Thr Thr Leu Ser Ile Thr Phe
    50                  55                  60

Lys Lys Cys Val Phe Leu Arg Asn Arg Arg Cys Glu Leu Gln Thr Thr
65                  70                  75                  80

Gly Val Phe Asp Thr Asp His Thr Glu Arg Met Thr Thr Leu His Arg
                85                  90                  95

Gly Ile Phe Thr Arg Thr Glu Thr Leu Leu Phe Leu Ser Arg Asp Arg
            100                 105                 110

Ser Cys Ala Val Val Lys Val Tyr Ser Leu Thr Asn Trp Asn Gln Ser
        115                 120                 125

Tyr Tyr Asp Met Arg Val Thr Asn Thr Phe Val Arg Ser Ala Ser Leu
    130                 135                 140

Pro Ala Cys Arg Thr Phe Phe Asn Arg Ile Ile Arg Pro Gln Thr Ser
145                 150                 155                 160

His Leu Val Phe Phe Pro Arg Cys Leu Arg Leu Met Arg Gln Arg Asn
                165                 170                 175

Glu Asp Glu Glu
            180

<210> SEQ ID NO 13
<211> LENGTH: 178
<212> TYPE: PRT
<213> ORGANISM: Rhipicephalus microplus

<400> SEQUENCE: 13

Met Leu Arg Gly Ala Leu Ala Ala Ile Leu Leu Leu Ile Ser Ser Asp
1               5                   10                  15

Leu Met Ile His Thr Ala Gly Leu Asp Ile Lys Gln Phe Val Arg Arg
            20                  25                  30

Arg Glu Arg Ile Trp Thr Tyr Lys Thr Thr Arg Arg Asp Asn Val Gln
        35                  40                  45

Cys Glu Val Asp Lys Leu Leu Tyr Ser Thr Thr Leu Ser Ile Thr Phe
    50                  55                  60

Lys Lys Cys Val Phe Leu Arg Asn Arg Arg Cys Glu Leu Gln Ile Thr
65                  70                  75                  80

Gly Val Phe Asp Thr Asp Ile Met Glu Arg Met Thr Thr Ile Asp Arg
                85                  90                  95

Asp Ile Phe Thr Ala Thr Glu Thr Leu Leu Phe Leu Ser Arg Asp His
            100                 105                 110

Ser Cys Ala Val Met Lys Val Glu Ser Leu Thr Asn Trp Asp Gln Phe
        115                 120                 125

Tyr Tyr Asp Met Arg Val Pro Gly Ser Phe Glu Arg Phe Ala Pro Pro
    130                 135                 140

Pro Asp Cys Arg Val Phe Phe Asp Arg Ile Ile Gly Pro Gln Val Ala
145                 150                 155                 160

His Arg Val Phe Phe Pro Arg Cys Ile Arg Leu Met Ser Gln Arg Asn

Gln Glu

<210> SEQ ID NO 14
<211> LENGTH: 271
<212> TYPE: PRT
<213> ORGANISM: Rhipicephalus microplus

<400> SEQUENCE: 14

Met Ala Arg Glu Ile Val Leu Val Cys Met Ile Ala Ala Val Ala Arg
1               5                   10                  15

Thr Ala Leu Ser Ala Pro Lys Ala Arg Val Ser Arg Lys Asn Ile Gln
            20                  25                  30

Asp Arg Ile Gln Gln Leu Ala Lys Asp Phe Glu Ala His Leu Gln Asp
        35                  40                  45

Ala Ser Met Pro Arg His Cys Ala Glu Leu Leu Glu Asn Gly Gln His
    50                  55                  60

Ile Ser Gly Val Tyr Thr Ile Phe His Glu Ala Ala Gly Thr Ser Gly
65                  70                  75                  80

Gln Asp Val Tyr Cys Asp Met Asp Thr Asp Asp Gly Gly Trp Thr Val
                85                  90                  95

Ile Gln Arg Arg Gly Gln Tyr Gly His Asn Ala Tyr Tyr Phe Tyr Arg
            100                 105                 110

Asn Trp Thr Glu Tyr Ala Asn Gly Phe Gly Asn Pro Ala Asp Glu Tyr
        115                 120                 125

Trp Ile Gly Asn Lys Ala Leu His Ala Leu Thr Ser Gly Asp Glu Glu
    130                 135                 140

Met Val Leu Arg Ile Val Leu Ser Asn Ser Thr Glu Asp Ser Thr Tyr
145                 150                 155                 160

Phe Asp Tyr Lys Thr Phe Thr Val Ala Ser Glu Gln Leu Phe Gln
                165                 170                 175

Leu Arg Ile Gly Asn Phe Ser Glu Met Thr Gly Asp Pro Met Glu Arg
            180                 185                 190

Leu Ser Gly Gln Lys Phe Thr Thr Tyr Asp Arg Asp Asn Asp Ala Ser
        195                 200                 205

Ala Phe Asn Cys Ala Glu Arg Leu Arg Gly Ala Trp Trp Tyr Ile Leu
    210                 215                 220

Cys Asp Asp Ser Asn Leu Asn Gly Leu Asn Leu Asn Gly His His Asp
225                 230                 235                 240

Ser Ser Gly Asp Gly Ile Val Trp Glu Gly Thr Ser Ser Asp Ala Ala
                245                 250                 255

His Tyr Ser Tyr Pro Lys Val Glu Met Met Ile Arg Pro Ala Lys
            260                 265                 270

<210> SEQ ID NO 15
<211> LENGTH: 262
<212> TYPE: PRT
<213> ORGANISM: Rhipicephalus australis

<400> SEQUENCE: 15

Met Ile Ala Ala Val Ala Arg Thr Gly Leu Ser Ala Pro Lys Ala Arg
1               5                   10                  15

Val Ser Arg Lys Asn Ile Gln Asp Arg Ile Gln Gln Leu Ala Lys Asp
            20                  25                  30

Phe Glu Ala His Leu Gln Asp Ala Ser Met Pro Arg His Cys Ala Glu
        35                  40                  45

```
Leu Leu Asp Asn Gly Gln His Ile Ser Gly Val Tyr Thr Ile Phe His
 50                  55                  60

Glu Ala Ala Gly Thr Ser Gly Gln Asp Val Tyr Cys Asp Met Asp Thr
 65                  70                  75                  80

Asp Asp Gly Gly Trp Thr Val Ile Gln Arg Arg Gly Gln Tyr Gly His
                 85                  90                  95

Asn Ala Tyr Tyr Phe Tyr Arg Asn Trp Thr Glu Tyr Ala Asn Gly Phe
            100                 105                 110

Gly Asn Pro Ala Asp Glu Tyr Trp Ile Gly Asn Lys Ala Leu His Ala
        115                 120                 125

Leu Thr Ser Gly Asp Glu Glu Met Val Leu Arg Ile Val Leu Ser Asn
130                 135                 140

Ser Thr Glu Asp Ser Thr Tyr Phe Asp Tyr Lys Thr Phe Ile Val Ala
145                 150                 155                 160

Ser Glu Glu Glu Leu Phe Gln Leu Arg Ile Gly Asn Phe Thr Gly Met
                165                 170                 175

Ser Gly Asp Pro Met Glu Arg Leu Ser Gly Arg Gln Phe Ser Thr Tyr
            180                 185                 190

Asp Leu Asp Asn Asp Ala Ser Gly Tyr Asn Cys Ala Glu Arg Leu Arg
        195                 200                 205

Gly Ala Trp Trp Tyr Phe Leu Cys Glu Asp Ser Asn Leu Asn Gly Leu
210                 215                 220

Asn Leu Asn Gly His His Asp Ser Ser Gly Asp Gly Ile Val Trp Glu
225                 230                 235                 240

Gly Thr Ser Ser Asp Ala Ala His Tyr Ser Tyr Pro Lys Val Glu Met
                245                 250                 255

Met Ile Arg Pro Ala Asn
            260

<210> SEQ ID NO 16
<211> LENGTH: 160
<212> TYPE: PRT
<213> ORGANISM: Rhipicephalus microplus

<400> SEQUENCE: 16

Met Val Asn Ser Arg Val Val Asn Gly Val Ala Val Val Ala Val
 1               5                  10                  15

Val Val Met Val Val Val Ser Val Val Val Pro Val Val Gln Gly Lys
                 20                  25                  30

Pro Lys Ala Gly Ser Gly Gly Pro Ala Ala Gly Ala Pro Asp Phe Ser
             35                  40                  45

Lys Phe Leu Gly Pro Pro Leu Pro Ser Glu Asp Cys Val Gly Val Val
 50                  55                  60

Ala Ala Pro Gly Ala Ala Ala Leu Val Ala Asp Pro Asn Asp Cys Thr
 65                  70                  75                  80

Lys Tyr Ser Val Cys Ser Glu Thr Phe Ser Ser Lys Phe Asp Cys Pro
                 85                  90                  95

Pro Gly Gln His Phe Ser Pro Ala Asp Asn Arg Cys Ala Thr Pro Glu
            100                 105                 110

Glu Ala Lys Cys Asp Pro Ala Phe Ala Asp Asn Asp Thr Asp Asp
        115                 120                 125

Glu Ala Ile Asn Val Asp Val Lys Ser Val Ala Val Asp Val Val Asp
130                 135                 140

Ala Ala Asp Val Glu Val Asp Ala Ala Asn Ile Val Ala Thr Asp Val
```

```
            145                 150                 155                 160

<210> SEQ ID NO 17
<211> LENGTH: 160
<212> TYPE: PRT
<213> ORGANISM: Rhipicephalus australis

<400> SEQUENCE: 17

Met Val Asn Ser Lys Val Val Asn Gly Val Ala Val Ala Val
1               5                   10                  15

Val Val Met Val Val Val Ser Val Val Val Pro Val Val Gln Gly Lys
            20                  25                  30

Pro Lys Ala Ser Ser Gly Gly Pro Ala Ala Gly Ala Pro Asp Phe Ser
        35                  40                  45

Lys Phe Leu Gly Pro Pro Leu Pro Ser Glu Asp Cys Val Gly Val Val
    50                  55                  60

Ala Ala Pro Gly Ala Ala Ala Leu Val Ala Asp Pro Asn Asp Cys Thr
65                  70                  75                  80

Lys Tyr Ser Val Cys Ser Glu Thr Phe Ser Ser Lys Phe Asp Cys Pro
                85                  90                  95

Pro Gly Gln His Phe Ser Pro Ala Asp Asn Arg Cys Ala Thr Pro Glu
            100                 105                 110

Glu Ala Lys Cys Asp Pro Ala Phe Ala Asp Asn Asp Ala Thr Asp Asp
        115                 120                 125

Glu Ala Ile Asn Val Asp Val Lys Ser Val Ala Val Asp Val Val Asp
    130                 135                 140

Ala Ala Asp Val Glu Gly Asp Ala Ala Asn Ile Ile Ala Thr Asp Val
145                 150                 155                 160

<210> SEQ ID NO 18
<211> LENGTH: 3408
<212> TYPE: PRT
<213> ORGANISM: Megathura crenulata

<400> SEQUENCE: 18

Met Leu Ser Val Arg Leu Leu Ile Val Val Leu Ala Leu Ala Asn Ala
1               5                   10                  15

Glu Asn Leu Val Arg Lys Ser Val Glu His Leu Thr Gln Glu Glu Thr
            20                  25                  30

Leu Asp Leu Gln Ala Ala Leu Arg Glu Leu Gln Met Asp Ser Ser Ser
        35                  40                  45

Ile Gly Phe Gln Lys Ile Ala Ala His Gly Ala Pro Ala Ser Cys
    50                  55                  60

Val His Lys Asp Thr Ser Ile Ala Cys Cys Ile His Gly Met Pro Thr
65                  70                  75                  80

Phe Pro His Trp His Arg Ala Tyr Val Val His Met Glu Arg Ala Leu
                85                  90                  95

Gln Thr Lys Arg Arg Thr Ser Gly Leu Pro Tyr Trp Asp Trp Thr Glu
            100                 105                 110

Pro Ile Thr Gln Leu Pro Ser Leu Ala Ala Asp Pro Val Tyr Ile Asp
        115                 120                 125

Ser Gln Gly Gly Lys Ala His Thr Asn Tyr Trp Tyr Arg Gly Asn Ile
    130                 135                 140

Asp Phe Leu Asp Lys Lys Thr Asn Arg Ala Val Asp Asp Arg Leu Phe
145                 150                 155                 160

Glu Lys Val Lys Pro Gly Gln His Thr His Leu Met Glu Ser Val Leu
```

```
                165                 170                 175
Asp Ala Leu Glu Gln Asp Glu Phe Cys Lys Phe Glu Ile Gln Phe Glu
            180                 185                 190

Leu Ala His Asn Ala Ile His Tyr Leu Val Gly Gly Lys His Asp Tyr
        195                 200                 205

Ser Met Ala Asn Leu Glu Tyr Thr Ala Tyr Asp Pro Ile Phe Phe Leu
        210                 215                 220

His His Ser Asn Val Asp Arg Ile Phe Ala Ile Trp Gln Arg Leu Gln
225                 230                 235                 240

Glu Leu Arg Asn Lys Asp Pro Lys Ala Met Asp Cys Ala Gln Glu Leu
            245                 250                 255

Leu His Gln Lys Met Glu Pro Phe Ser Trp Glu Asp Asn Asp Ile Pro
        260                 265                 270

Leu Thr Asn Asp Tyr Asp Thr Leu Asn Leu Asn Gly Met Thr Pro Glu
        275                 280                 285

Glu Leu Lys Thr Tyr Leu Asp Glu Arg Ser Ser Arg Ala Arg Ala Phe
        290                 295                 300

Ala Ser Phe Arg Leu Lys Gly Phe Gly Gly Ser Ala Asn Val Phe Val
305                 310                 315                 320

Tyr Val Cys Ile Pro Asp Asn Asp Arg Asn Asp His Cys Glu
                325                 330                 335

Lys Ala Gly Asp Phe Phe Val Leu Gly Gly Pro Ser Glu Met Lys Trp
            340                 345                 350

Gln Phe Tyr Arg Pro Tyr Leu Phe Asp Leu Ser Asp Thr Val His Lys
        355                 360                 365

Met Gly Met Lys Leu Asp Gly His Tyr Thr Val Lys Ala Glu Leu Phe
        370                 375                 380

Ser Val Asn Gly Thr Ala Leu Pro Asp Asp Leu Leu Pro His Pro Val
385                 390                 395                 400

Val Val His His Pro Glu Lys Gly Phe Thr Asp Pro Pro Val Lys His
            405                 410                 415

His Gln Ser Ala Asn Leu Leu Val Arg Lys Asn Ile Asn Asp Leu Thr
        420                 425                 430

Arg Glu Glu Val Leu Asn Leu Arg Glu Ala Phe His Lys Phe Gln Glu
        435                 440                 445

Asp Arg Ser Val Asp Gly Tyr Gln Ala Thr Ala Glu Tyr His Gly Leu
        450                 455                 460

Pro Ala Arg Cys Pro Arg Pro Asp Ala Lys Asp Arg Tyr Ala Cys Cys
465                 470                 475                 480

Val His Gly Met Pro Ile Phe Pro His Trp His Arg Leu Phe Val Thr
            485                 490                 495

Gln Val Glu Asp Ala Leu Val Gly Arg Gly Ala Thr Ile Gly Ile Pro
        500                 505                 510

Tyr Trp Gly Leu Pro Tyr Trp Asp Trp Thr Glu Pro Met Thr His Ile
        515                 520                 525

Pro Gly Leu Ala Gly Asn Lys Thr Tyr Val Asp Ser His Gly Ala Ser
        530                 535                 540

His Thr Asn Pro Phe His Ser Ser Val Ile Ala Phe Glu Glu Asn Ala
545                 550                 555                 560

Pro His Thr Lys Arg Gln Ile Asp Gln Arg Leu Phe Lys Pro Ala Thr
            565                 570                 575

Phe Gly His His Thr Asp Leu Phe Asn Gln Ile Leu Tyr Ala Phe Glu
        580                 585                 590
```

-continued

```
Gln Glu Asp Tyr Cys Asp Phe Glu Val Gln Phe Glu Ile Thr His Asn
        595                 600                 605
Thr Ile His Ala Trp Thr Gly Gly Ser Glu His Phe Ser Met Ser Ser
610                 615                 620
Leu His Tyr Thr Ala Phe Asp Pro Leu Phe Tyr Phe His His Ser Asn
625                 630                 635                 640
Val Asp Arg Leu Trp Ala Val Trp Gln Ala Leu Gln Met Arg His
                645                 650                 655
Lys Pro Tyr Arg Ala His Cys Ala Ile Ser Leu Glu His Met His Leu
                660                 665                 670
Lys Pro Phe Ala Phe Ser Ser Pro Leu Asn Asn Asn Glu Lys Thr His
                675                 680                 685
Ala Asn Ala Met Pro Asn Lys Ile Tyr Asp Tyr Glu Asn Val Leu His
                690                 695                 700
Tyr Thr Tyr Glu Asp Leu Thr Phe Gly Gly Ile Ser Leu Glu Asn Ile
705                 710                 715                 720
Glu Lys Met Ile His Glu Asn Gln Gln Glu Asp Arg Ile Tyr Ala Gly
                    725                 730                 735
Phe Leu Leu Ala Gly Ile Arg Thr Ser Ala Asn Val Asp Ile Phe Ile
                740                 745                 750
Lys Thr Thr Asp Ser Val Gln His Lys Ala Gly Thr Phe Ala Val Leu
                755                 760                 765
Gly Gly Ser Lys Glu Met Lys Trp Gly Phe Asp Arg Val Phe Lys Phe
                770                 775                 780
Asp Ile Thr His Val Leu Lys Asp Leu Asp Leu Thr Ala Asp Gly Asp
785                 790                 795                 800
Phe Glu Val Thr Val Asp Ile Thr Glu Val Asp Gly Thr Lys Leu Ala
                    805                 810                 815
Ser Ser Leu Ile Pro His Ala Ser Val Ile Arg Glu His Ala Arg Gly
                820                 825                 830
Lys Leu Asn Arg Val Lys Phe Asp Lys Val Pro Arg Ser Arg Leu Ile
                835                 840                 845
Arg Lys Asn Val Asp Arg Leu Ser Pro Glu Glu Met Asn Glu Leu Arg
                850                 855                 860
Lys Ala Leu Ala Leu Leu Lys Glu Asp Lys Ser Ala Gly Gly Phe Gln
865                 870                 875                 880
Gln Leu Gly Ala Phe His Gly Glu Pro Lys Trp Cys Pro Ser Pro Glu
                    885                 890                 895
Ala Ser Lys Lys Phe Ala Cys Cys Val His Gly Met Ser Val Phe Pro
                900                 905                 910
His Trp His Arg Leu Leu Thr Val Gln Ser Glu Asn Ala Leu Arg Arg
                915                 920                 925
His Gly Tyr Asp Gly Ala Leu Pro Tyr Trp Asp Trp Thr Ser Pro Leu
                930                 935                 940
Asn His Leu Pro Glu Leu Ala Asp His Glu Lys Tyr Val Asp Pro Glu
945                 950                 955                 960
Asp Gly Val Glu Lys His Asn Pro Trp Phe Asp Gly His Ile Asp Thr
                    965                 970                 975
Val Asp Lys Thr Thr Thr Arg Ser Val Gln Asn Lys Leu Phe Glu Gln
                980                 985                 990
Pro Glu Phe Gly His Tyr Thr Ser Ile Ala Lys Gln Val Leu Leu Ala
                995                 1000                1005
```

```
Leu Glu Gln Asp Asn Phe Cys Asp Phe Glu Ile Gln Tyr Glu Ile
1010                1015                1020

Ala His Asn Tyr Ile His Ala Leu Val Gly Gly Ala Gln Pro Tyr
1025                1030                1035

Gly Met Ala Ser Leu Arg Tyr Thr Ala Phe Asp Pro Leu Phe Tyr
1040                1045                1050

Leu His His Ser Asn Thr Asp Arg Ile Trp Ala Ile Trp Gln Ala
1055                1060                1065

Leu Gln Lys Tyr Arg Gly Lys Pro Tyr Asn Val Ala Asn Cys Ala
1070                1075                1080

Val Thr Ser Met Arg Glu Pro Leu Gln Pro Phe Gly Leu Ser Ala
1085                1090                1095

Asn Ile Asn Thr Asp His Val Thr Lys Glu His Ser Val Pro Phe
1100                1105                1110

Asn Val Phe Asp Tyr Lys Thr Asn Phe Asn Tyr Glu Tyr Asp Thr
1115                1120                1125

Leu Glu Phe Asn Gly Leu Ser Ile Ser Gln Leu Asn Lys Lys Leu
1130                1135                1140

Glu Ala Ile Lys Ser Gln Asp Arg Phe Phe Ala Gly Phe Leu Leu
1145                1150                1155

Ser Gly Phe Lys Lys Ser Ser Leu Val Lys Phe Asn Ile Cys Thr
1160                1165                1170

Asp Ser Ser Asn Cys His Pro Ala Gly Glu Phe Tyr Leu Leu Gly
1175                1180                1185

Asp Glu Asn Glu Met Pro Trp Ala Tyr Asp Arg Val Phe Lys Tyr
1190                1195                1200

Asp Ile Thr Glu Lys Leu His Asp Leu Lys Leu His Ala Glu Asp
1205                1210                1215

His Phe Tyr Ile Asp Tyr Glu Val Phe Asp Leu Lys Pro Ala Ser
1220                1225                1230

Leu Gly Lys Asp Leu Phe Lys Gln Pro Ser Val Ile His Glu Pro
1235                1240                1245

Arg Ile Gly His His Glu Gly Glu Val Tyr Gln Ala Glu Val Thr
1250                1255                1260

Ser Ala Asn Arg Ile Arg Lys Asn Ile Glu Asn Leu Ser Leu Gly
1265                1270                1275

Glu Leu Glu Ser Leu Arg Ala Ala Phe Leu Glu Ile Glu Asn Asp
1280                1285                1290

Gly Thr Tyr Glu Ser Ile Ala Lys Phe His Gly Ser Pro Gly Leu
1295                1300                1305

Cys Gln Leu Asn Gly Asn Pro Ile Ser Cys Cys Val His Gly Met
1310                1315                1320

Pro Thr Phe Pro His Trp His Arg Leu Tyr Val Val Val Val Glu
1325                1330                1335

Asn Ala Leu Leu Lys Lys Gly Ser Ser Val Ala Val Pro Tyr Trp
1340                1345                1350

Asp Trp Thr Lys Arg Ile Glu His Leu Pro His Leu Ile Ser Asp
1355                1360                1365

Ala Thr Tyr Tyr Asn Ser Arg Gln His His Tyr Glu Thr Asn Pro
1370                1375                1380

Phe His His Gly Lys Ile Thr His Glu Asn Glu Ile Thr Thr Arg
1385                1390                1395

Asp Pro Lys Asp Ser Leu Phe His Ser Asp Tyr Phe Tyr Glu Gln
```

```
                1400                1405                1410
Val Leu Tyr Ala Leu Glu Gln Asp Asn Phe Cys Asp Phe Glu Ile
    1415                1420                1425

Gln Leu Glu Ile Leu His Asn Ala Leu His Ser Leu Leu Gly Gly
    1430                1435                1440

Lys Gly Lys Tyr Ser Met Ser Asn Leu Asp Tyr Ala Ala Phe Asp
    1445                1450                1455

Pro Val Phe Phe Leu His His Ala Thr Thr Asp Arg Ile Trp Ala
    1460                1465                1470

Ile Trp Gln Asp Leu Gln Arg Phe Arg Lys Arg Pro Tyr Arg Glu
    1475                1480                1485

Ala Asn Cys Ala Ile Gln Leu Met His Thr Pro Leu Gln Pro Phe
    1490                1495                1500

Asp Lys Ser Asp Asn Asn Asp Glu Ala Thr Lys Thr His Ala Thr
    1505                1510                1515

Pro His Asp Gly Phe Glu Tyr Gln Asn Ser Phe Gly Tyr Ala Tyr
    1520                1525                1530

Asp Asn Leu Glu Leu Asn His Tyr Ser Ile Pro Gln Leu Asp His
    1535                1540                1545

Met Leu Gln Glu Arg Lys Arg His Asp Arg Val Phe Ala Gly Phe
    1550                1555                1560

Leu Leu His Asn Ile Gly Thr Ser Ala Asp Gly His Val Phe Val
    1565                1570                1575

Cys Leu Pro Thr Gly Glu His Thr Lys Asp Cys Ser His Glu Ala
    1580                1585                1590

Gly Met Phe Ser Ile Leu Gly Gly Gln Thr Glu Met Ser Phe Val
    1595                1600                1605

Phe Asp Arg Leu Tyr Lys Leu Asp Ile Thr Lys Ala Leu Lys Lys
    1610                1615                1620

Asn Gly Val His Leu Gln Gly Asp Phe Asp Leu Glu Ile Glu Ile
    1625                1630                1635

Thr Ala Val Asn Gly Ser His Leu Asp Ser His Val Ile His Ser
    1640                1645                1650

Pro Thr Ile Leu Phe Glu Ala Gly Thr Asp Ser Ala His Thr Asp
    1655                1660                1665

Asp Gly His Thr Glu Pro Val Met Ile Arg Lys Asp Ile Thr Gln
    1670                1675                1680

Leu Asp Lys Arg Gln Gln Leu Ser Leu Val Lys Ala Leu Glu Ser
    1685                1690                1695

Met Lys Ala Asp His Ser Ser Asp Gly Phe Gln Ala Ile Ala Ser
    1700                1705                1710

Phe His Ala Leu Pro Pro Leu Cys Pro Ser Pro Ala Ala Ser Lys
    1715                1720                1725

Arg Phe Ala Cys Cys Val His Gly Met Ala Thr Phe Pro Gln Trp
    1730                1735                1740

His Arg Leu Tyr Thr Val Gln Phe Gln Asp Ser Leu Arg Lys His
    1745                1750                1755

Gly Ala Val Val Gly Leu Pro Tyr Trp Asp Trp Thr Leu Pro Arg
    1760                1765                1770

Ser Glu Leu Pro Glu Leu Leu Thr Val Ser Thr Ile His Asp Pro
    1775                1780                1785

Glu Thr Gly Arg Asp Ile Pro Asn Pro Phe Ile Gly Ser Lys Ile
    1790                1795                1800
```

-continued

Glu Phe Glu Gly Glu Asn Val His Thr Lys Arg Asp Ile Asn Arg
1805                    1810                1815

Asp Arg Leu Phe Gln Gly Ser Thr Lys Thr His His Asn Trp Phe
1820                    1825                1830

Ile Glu Gln Ala Leu Leu Ala Leu Glu Gln Thr Asn Tyr Cys Asp
1835                    1840                1845

Phe Glu Val Gln Phe Glu Ile Met His Asn Gly Val His Thr Trp
1850                    1855                1860

Val Gly Gly Lys Glu Pro Tyr Gly Ile Gly His Leu His Tyr Ala
1865                    1870                1875

Ser Tyr Asp Pro Leu Phe Tyr Ile His His Ser Gln Thr Asp Arg
1880                    1885                1890

Ile Trp Ala Ile Trp Gln Ser Leu Gln Arg Phe Arg Gly Leu Ser
1895                    1900                1905

Gly Ser Glu Ala Asn Cys Ala Val Asn Leu Met Lys Thr Pro Leu
1910                    1915                1920

Lys Pro Phe Ser Phe Gly Ala Pro Tyr Asn Leu Asn Asp His Thr
1925                    1930                1935

His Asp Phe Ser Lys Pro Glu Asp Thr Phe Asp Tyr Gln Lys Phe
1940                    1945                1950

Gly Tyr Ile Tyr Asp Thr Leu Glu Phe Ala Gly Trp Ser Ile Arg
1955                    1960                1965

Gly Ile Asp His Ile Val Arg Asn Arg Gln Glu His Ser Arg Val
1970                    1975                1980

Phe Ala Gly Phe Leu Leu Glu Gly Phe Gly Thr Ser Ala Thr Val
1985                    1990                1995

Asp Phe Gln Val Cys Arg Thr Ala Gly Asp Cys Glu Asp Ala Gly
2000                    2005                2010

Tyr Phe Thr Val Leu Gly Gly Glu Lys Glu Met Pro Trp Ala Phe
2015                    2020                2025

Asp Arg Leu Tyr Lys Tyr Asp Ile Thr Glu Thr Leu Asp Lys Met
2030                    2035                2040

Asn Leu Arg His Asp Glu Ile Phe Gln Ile Glu Val Thr Ile Thr
2045                    2050                2055

Ser Tyr Asp Gly Thr Val Leu Asp Ser Gly Leu Ile Pro Thr Pro
2060                    2065                2070

Ser Ile Ile Tyr Asp Pro Ala His His Asp Ile Ser Ser His His
2075                    2080                2085

Leu Ser Leu Asn Lys Val Arg His Asp Leu Ser Thr Leu Ser Glu
2090                    2095                2100

Arg Asp Ile Gly Ser Leu Lys Tyr Ala Leu Ser Ser Leu Gln Ala
2105                    2110                2115

Asp Thr Ser Ala Asp Gly Phe Ala Ala Ile Ala Ser Phe His Gly
2120                    2125                2130

Leu Pro Ala Lys Cys Asn Asp Ser His Asn Asn Glu Val Ala Cys
2135                    2140                2145

Cys Ile His Gly Met Pro Thr Phe Pro His Trp His Arg Leu Tyr
2150                    2155                2160

Thr Leu Gln Phe Glu Gln Ala Leu Arg Arg His Gly Ser Ser Val
2165                    2170                2175

Ala Val Pro Tyr Trp Asp Trp Thr Lys Pro Ile His Asn Ile Pro
2180                    2185                2190

-continued

```
His Leu Phe Thr Asp Lys Glu Tyr Tyr Asp Val Trp Arg Asn Lys
2195                2200                2205

Val Met Pro Asn Pro Phe Ala Arg Gly Tyr Val Pro Ser His Asp
2210                2215                2220

Thr Tyr Thr Val Arg Asp Val Gln Glu Gly Leu Phe His Leu Thr
2225                2230                2235

Ser Thr Gly Glu His Ser Ala Leu Leu Asn Gln Ala Leu Leu Ala
2240                2245                2250

Leu Glu Gln His Asp Tyr Cys Asp Phe Ala Val Gln Phe Glu Val
2255                2260                2265

Met His Asn Thr Ile His Tyr Leu Val Gly Gly Pro Gln Val Tyr
2270                2275                2280

Ser Leu Ser Ser Leu His Tyr Ala Ser Tyr Asp Pro Ile Phe Phe
2285                2290                2295

Ile His His Ser Phe Val Asp Lys Val Trp Ala Val Trp Gln Ala
2300                2305                2310

Leu Gln Glu Lys Arg Gly Leu Pro Ser Asp Arg Ala Asp Cys Ala
2315                2320                2325

Val Ser Leu Met Thr Gln Asn Met Arg Pro Phe His Tyr Glu Ile
2330                2335                2340

Asn His Asn Gln Phe Thr Lys Lys His Ala Val Pro Asn Asp Val
2345                2350                2355

Phe Lys Tyr Glu Leu Leu Gly Tyr Arg Tyr Asp Asn Leu Glu Ile
2360                2365                2370

Gly Gly Met Asn Leu His Glu Ile Glu Lys Glu Ile Lys Asp Lys
2375                2380                2385

Gln His His Val Arg Val Phe Ala Gly Phe Leu Leu His Gly Ile
2390                2395                2400

Arg Thr Ser Ala Asp Val Gln Phe Gln Ile Cys Lys Thr Ser Glu
2405                2410                2415

Asp Cys His His Gly Gly Gln Ile Phe Val Leu Gly Gly Thr Lys
2420                2425                2430

Glu Met Ala Trp Ala Tyr Asn Arg Leu Phe Lys Tyr Asp Ile Thr
2435                2440                2445

His Ala Leu His Asp Ala His Ile Thr Pro Glu Asp Val Phe His
2450                2455                2460

Pro Ser Glu Pro Phe Phe Ile Lys Val Ser Val Thr Ala Val Asn
2465                2470                2475

Gly Thr Val Leu Pro Ala Ser Ile Leu His Ala Pro Thr Ile Ile
2480                2485                2490

Tyr Glu Pro Gly Leu Asp His His Glu Asp His His Ser Ser Ser
2495                2500                2505

Met Ala Gly His Gly Val Arg Lys Glu Ile Asn Thr Leu Thr Thr
2510                2515                2520

Ala Glu Val Asp Asn Leu Lys Asp Ala Met Arg Ala Val Met Ala
2525                2530                2535

Asp His Gly Pro Asn Gly Tyr Gln Ala Ile Ala Ala Phe His Gly
2540                2545                2550

Asn Pro Pro Met Cys Pro Met Pro Asp Gly Lys Asn Tyr Ser Cys
2555                2560                2565

Cys Thr His Gly Met Ala Thr Phe Pro His Trp His Arg Leu Tyr
2570                2575                2580

Thr Lys Gln Met Glu Asp Ala Leu Thr Ala His Gly Ala Arg Val
```

-continued

```
              2585                2590                2595
Gly Leu Pro Tyr Trp Asp Gly Thr Thr Ala Phe Thr Ala Leu Pro
    2600                2605                2610
Thr Phe Val Thr Asp Glu Glu Asp Asn Pro Phe His His Gly His
    2615                2620                2625
Ile Asp Tyr Leu Gly Val Asp Thr Thr Arg Ser Pro Arg Asp Lys
    2630                2635                2640
Leu Phe Asn Asp Pro Glu Arg Gly Ser Glu Ser Phe Phe Tyr Arg
    2645                2650                2655
Gln Val Leu Leu Ala Leu Glu Gln Thr Asp Phe Cys Gln Phe Glu
    2660                2665                2670
Val Gln Phe Glu Ile Thr His Asn Ala Ile His Ser Trp Thr Gly
    2675                2680                2685
Gly Leu Thr Pro Tyr Gly Met Ser Thr Leu Glu Tyr Thr Thr Tyr
    2690                2695                2700
Asp Pro Leu Phe Trp Leu His His Ala Asn Thr Asp Arg Ile Trp
    2705                2710                2715
Ala Ile Trp Gln Ala Leu Gln Glu Tyr Arg Gly Leu Pro Tyr Asp
    2720                2725                2730
His Ala Asn Cys Glu Ile Gln Ala Met Lys Arg Pro Leu Arg Pro
    2735                2740                2745
Phe Ser Asp Pro Ile Asn His Asn Ala Phe Thr His Ser Asn Ala
    2750                2755                2760
Lys Pro Thr Asp Val Phe Glu Tyr Ser Arg Phe Asn Phe Gln Tyr
    2765                2770                2775
Asp Asn Leu Arg Phe His Gly Met Thr Ile Lys Lys Leu Glu His
    2780                2785                2790
Glu Leu Glu Lys Gln Lys Glu Asp Arg Thr Phe Ala Ala Phe
    2795                2800                2805
Leu Leu His Gly Ile Lys Lys Ser Ala Asp Val Ser Phe Asp Val
    2810                2815                2820
Cys Asn His Asp Gly Glu Cys His Phe Ala Gly Thr Phe Ala Ile
    2825                2830                2835
Leu Gly Gly Glu His Glu Met Pro Trp Ser Phe Asp Arg Leu Phe
    2840                2845                2850
Arg Tyr Asp Ile Thr Gln Val Leu Lys Gln Met His Leu Glu Tyr
    2855                2860                2865
Asp Ser Asp Phe Thr Phe His Met Arg Ile Ile Asp Thr Ser Gly
    2870                2875                2880
Lys Gln Leu Pro Ser Asp Leu Ile Lys Met Pro Thr Val Glu His
    2885                2890                2895
Ser Pro Gly Gly Lys His His Glu Lys His His Glu Asp His His
    2900                2905                2910
Glu Asp Ile Leu Val Arg Lys Asn Ile His Ser Leu Ser His His
    2915                2920                2925
Glu Ala Glu Glu Leu Arg Asp Ala Leu Tyr Lys Leu Gln Asn Asp
    2930                2935                2940
Glu Ser His Gly Gly Tyr Glu His Ile Ala Gly Phe His Gly Tyr
    2945                2950                2955
Pro Asn Leu Cys Pro Glu Lys Gly Asp Glu Lys Tyr Pro Cys Cys
    2960                2965                2970
Val His Gly Met Ser Ile Phe Pro His Trp His Arg Leu His Thr
    2975                2980                2985
```

```
Ile Gln Phe Glu Arg Ala Leu Lys Lys His Gly Ser His Leu Gly
    2990                2995                3000

Ile Pro Tyr Trp Asp Trp Thr Gln Thr Ile Ser Ser Leu Pro Thr
    3005                3010                3015

Phe Phe Ala Asp Ser Gly Asn Asn Asn Pro Phe Phe Lys Tyr His
    3020                3025                3030

Ile Arg Ser Ile Asn Gln Asp Thr Val Arg Asp Val Asn Glu Ala
    3035                3040                3045

Ile Phe Gln Gln Thr Lys Phe Gly Glu Phe Ser Ser Ile Phe Tyr
    3050                3055                3060

Leu Ala Leu Gln Ala Leu Glu Glu Asp Asn Tyr Cys Asp Phe Glu
    3065                3070                3075

Val Gln Tyr Glu Ile Leu His Asn Glu Val His Ala Leu Ile Gly
    3080                3085                3090

Gly Ala Glu Lys Tyr Ser Met Ser Thr Leu Glu Tyr Ser Ala Phe
    3095                3100                3105

Asp Pro Tyr Phe Met Ile His His Ala Ser Leu Asp Lys Ile Trp
    3110                3115                3120

Ile Ile Trp Gln Glu Leu Gln Lys Arg Arg Val Lys Pro Ala His
    3125                3130                3135

Ala Gly Ser Cys Ala Gly Asp Ile Met His Val Pro Leu His Pro
    3140                3145                3150

Phe Asn Tyr Glu Ser Val Asn Asn Asp Asp Phe Thr Arg Glu Asn
    3155                3160                3165

Ser Leu Pro Asn Ala Val Val Asp Ser His Arg Phe Asn Tyr Lys
    3170                3175                3180

Tyr Asp Asn Leu Asn Leu His Gly His Asn Ile Glu Glu Leu Glu
    3185                3190                3195

Glu Val Leu Arg Ser Leu Arg Leu Lys Ser Arg Val Phe Ala Gly
    3200                3205                3210

Phe Val Leu Ser Gly Ile Arg Thr Thr Ala Val Val Lys Val Tyr
    3215                3220                3225

Ile Lys Ser Gly Thr Asp Ser Asp Asp Glu Tyr Ala Gly Ser Phe
    3230                3235                3240

Val Ile Leu Gly Gly Ala Lys Glu Met Pro Trp Ala Tyr Glu Arg
    3245                3250                3255

Leu Tyr Arg Phe Asp Ile Thr Glu Thr Val His Asn Leu Asn Leu
    3260                3265                3270

Thr Asp Asp His Val Lys Phe Arg Phe Asp Leu Lys Lys Tyr Asp
    3275                3280                3285

His Thr Glu Leu Asp Ala Ser Val Leu Pro Ala Pro Ile Ile Val
    3290                3295                3300

Arg Arg Pro Asn Asn Ala Val Phe Asp Ile Ile Glu Ile Pro Ile
    3305                3310                3315

Gly Lys Asp Val Asn Leu Pro Pro Lys Val Val Lys Arg Gly
    3320                3325                3330

Thr Lys Ile Met Phe Met Ser Val Asp Glu Ala Val Thr Thr Pro
    3335                3340                3345

Met Leu Asn Leu Gly Ser Tyr Thr Ala Met Phe Lys Cys Lys Val
    3350                3355                3360

Pro Pro Phe Ser Phe His Ala Phe Glu Leu Gly Lys Met Tyr Ser
    3365                3370                3375
```

```
Val Glu  Ser Gly Asp Tyr Phe  Met Thr Ala Ser  Thr Thr Glu Leu
    3380             3385              3390

Cys Asn  Asp Asn Asn Leu Arg  Ile His Val His  Val Asp Asp Glu
    3395             3400              3405

<210> SEQ ID NO 19
<211> LENGTH: 128
<212> TYPE: PRT
<213> ORGANISM: Bos taurus

<400> SEQUENCE: 19

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ile Ile Glu Pro
65                  70                  75                  80

Ser Leu Arg Gln Leu Ala Gln Lys Tyr Asn Cys Asp Lys Met Ile Cys
                85                  90                  95

Arg Lys Cys Tyr Ala Arg Leu His Pro Arg Ala Val Asn Cys Arg Lys
            100                 105                 110

Lys Lys Cys Gly His Thr Asn Asn Leu Arg Pro Lys Lys Lys Val Lys
        115                 120                 125

<210> SEQ ID NO 20
<211> LENGTH: 624
<212> TYPE: PRT
<213> ORGANISM: Bos taurus

<400> SEQUENCE: 20

Cys Thr Cys Thr Thr Cys Ala Ala Cys Cys Ala Gly Gly Cys Gly Gly
1               5                   10                  15

Cys Cys Gly Ala Gly Cys Ala Gly Cys Ala Gly Cys Gly Cys Gly Cys Ala
            20                  25                  30

Gly Ala Gly Ala Thr Gly Cys Ala Gly Ala Thr Cys Thr Thr Thr Gly
        35                  40                  45

Thr Gly Ala Ala Gly Ala Cys Cys Cys Thr Gly Ala Cys Gly Gly Gly
    50                  55                  60

Cys Ala Ala Gly Ala Cys Ala Thr Cys Ala Cys Cys Cys Thr Thr
65                  70                  75                  80

Gly Ala Gly Gly Thr Cys Gly Ala Gly Cys Cys Cys Ala Gly Thr Gly
                85                  90                  95

Ala Cys Ala Cys Cys Ala Thr Thr Gly Ala Gly Ala Ala Thr Gly Thr
            100                 105                 110

Cys Ala Ala Ala Gly Cys Cys Ala Ala Ala Thr Cys Cys Ala Ala
        115                 120                 125

Gly Ala Cys Ala Ala Gly Gly Ala Gly Gly Gly Cys Ala Thr Cys Cys
    130                 135                 140

Cys Ala Cys Cys Thr Gly Ala Cys Ala Gly Cys Ala Gly Cys Gly Gly
145                 150                 155                 160

Gly Cys Thr Gly Ala Thr Cys Thr Thr Cys Gly Cys Thr Gly Gly Cys
                165                 170                 175
```

-continued

```
Ala Ala Ala Cys Ala Gly Cys Thr Gly Gly Ala Gly Ala Thr Gly
                180                 185                 190

Gly Cys Cys Gly Cys Ala Cys Thr Cys Thr Gly Thr Cys Ala Gly Ala
                195                 200                 205

Thr Thr Ala Thr Ala Ala Thr Ala Thr Cys Cys Ala Gly Ala Ala Ala
        210                 215                 220

Gly Ala Gly Thr Cys Cys Ala Cys Cys Cys Thr Gly Cys Ala Cys Thr
225                 230                 235                 240

Thr Gly Gly Thr Gly Cys Thr Thr Cys Gly Thr Cys Thr Gly Cys Gly
                245                 250                 255

Ala Gly Gly Cys Gly Gly Cys Ala Thr Cys Ala Thr Cys Gly Ala Gly
                260                 265                 270

Cys Cys Thr Thr Cys Cys Cys Thr Cys Cys Gly Cys Cys Ala Gly Cys
                275                 280                 285

Thr Cys Gly Cys Thr Cys Ala Gly Ala Ala Ala Thr Ala Cys Ala Ala
        290                 295                 300

Cys Thr Gly Cys Gly Ala Cys Ala Ala Gly Ala Thr Gly Ala Thr Cys
305                 310                 315                 320

Thr Gly Cys Cys Gly Cys Ala Ala Gly Thr Gly Thr Thr Ala Cys Gly
                325                 330                 335

Cys Cys Cys Gly Cys Cys Thr Gly Cys Ala Cys Cys Cys Cys Cys Gly
                340                 345                 350

Thr Gly Cys Thr Gly Thr Cys Ala Cys Thr Gly Cys Cys Gly Cys Cys
        355                 360                 365

Ala Ala Gly Ala Ala Gly Ala Ala Gly Thr Gly Thr Gly Gly Cys Cys
370                 375                 380

Ala Cys Ala Cys Ala Ala Cys Ala Ala Cys Cys Thr Gly Cys Gly
385                 390                 395                 400

Cys Cys Cys Cys Ala Ala Gly Ala Ala Gly Ala Ala Gly Gly Thr Cys
                405                 410                 415

Ala Ala Ala Thr Ala Ala Ala Gly Cys Thr Cys Thr Thr Cys Cys Ala
        420                 425                 430

Cys Cys Thr Gly Cys Thr Thr Cys Thr Cys Cys Thr Thr Thr Gly Cys
        435                 440                 445

Cys Cys Gly Cys Ala Gly Gly Gly Cys Gly Gly Cys Cys Thr Cys Cys
        450                 455                 460

Thr Gly Cys Cys Cys Ala Ala Gly Cys Cys Cys Cys Gly Thr Gly Gly
465                 470                 475                 480

Thr Cys Cys Thr Gly Gly Gly Cys Cys Thr Cys Ala Ala Thr Ala Ala
                485                 490                 495

Ala Gly Thr Thr Thr Cys Cys Cys Thr Thr Thr Cys Gly Thr Thr Gly
            500                 505                 510

Ala Cys Thr Gly Gly Ala Gly Cys Ala Gly Thr Ala Ala Ala Ala Ala
        515                 520                 525

Ala Ala Ala Ala Ala Ala Ala Ala Ala Ala Ala Ala Ala Ala
            530                 535                 540

Ala Ala Ala Ala Ala Ala Ala Ala Ala Ala Ala Ala Ala Ala Ala
545                 550                 555                 560

Ala Ala Ala Ala Ala Ala Ala Ala Ala Ala Ala Ala Ala Ala Ala
                565                 570                 575

Ala Ala Ala Ala Ala Ala Ala Ala Ala Ala Ala Ala Ala Ala Ala
            580                 585                 590

Ala Ala Ala Ala Ala Ala Ala Ala Ala Ala Ala Ala Ala Ala Gly
```

```
                    595                 600                 605
Ala Ala Ala Ala Ala Ala Ala Ala Ala Ala Ala Ala Ala Ala Ala
        610                 615                 620

<210> SEQ ID NO 21
<211> LENGTH: 15
<212> TYPE: PRT
<213> ORGANISM: Measles virus

<400> SEQUENCE: 21

Leu Ser Glu Ile Lys Gly Val Ile Val His Arg Leu Glu Gly Val
1               5                   10                  15

<210> SEQ ID NO 22
<211> LENGTH: 1315
<212> TYPE: PRT
<213> ORGANISM: Clostridium tetani

<400> SEQUENCE: 22

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
```

```
            290                 295                 300
Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
        370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
        450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
        530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
                580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
        610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
                660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
        690                 695                 700

Asp Asn Phe Leu Glu Lys Arg Tyr Glu Lys Trp Ile Glu Val Tyr Lys
705                 710                 715                 720
```

-continued

Leu Val Lys Ala Lys Trp Leu Gly Thr Val Asn Thr Gln Phe Gln Lys
            725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
            755                 760                 765

Glu Gln Ile Ala Asp Glu Ile Asn Asn Leu Lys Asn Lys Leu Glu Glu
            770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
            805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
            835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
            885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
            915                 920                 925

Glu Ser Ser Glu Val Ile Val His Lys Ala Met Asp Ile Glu Tyr Asn
            930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
            965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
            995                 1000                1005

Gly Glu Val Arg Gln Ile Thr Phe Arg Asp Leu Pro Asp Lys Phe
            1010                1015                1020

Asn Ala Tyr Leu Ala Asn Lys Trp Val Phe Ile Thr Ile Thr Asn
            1025                1030                1035

Asp Arg Leu Ser Ser Ala Asn Leu Tyr Ile Asn Gly Val Leu Met
            1040                1045                1050

Gly Ser Ala Glu Ile Thr Gly Leu Gly Ala Ile Arg Glu Asp Asn
            1055                1060                1065

Asn Ile Thr Leu Lys Leu Asp Arg Cys Asn Asn Asn Asn Gln Tyr
            1070                1075                1080

Val Ser Ile Asp Lys Phe Arg Ile Phe Cys Lys Ala Leu Asn Pro
            1085                1090                1095

Lys Glu Ile Glu Lys Leu Tyr Thr Ser Tyr Leu Ser Ile Thr Phe
            1100                1105                1110

Leu Arg Asp Phe Trp Gly Asn Pro Leu Arg Tyr Asp Thr Glu Tyr
            1115                1120                1125

```
Tyr Leu Ile Pro Val Ala Ser Ser Ser Lys Asp Val Gln Leu Lys
    1130                1135                1140

Asn Ile Thr Asp Tyr Met Tyr Leu Thr Asn Ala Pro Ser Tyr Thr
    1145                1150                1155

Asn Gly Lys Leu Asn Ile Tyr Arg Arg Leu Tyr Asn Gly Leu
    1160                1165                1170

Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Arg Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Trp Tyr Phe Asn His
    1280                1285                1290

Leu Lys Asp Lys Ile Leu Gly Cys Asp Trp Tyr Phe Val Pro Thr
    1295                1300                1305

Asp Glu Gly Trp Thr Asn Asp
    1310                1315

<210> SEQ ID NO 23
<211> LENGTH: 18
<212> TYPE: PRT
<213> ORGANISM: Clostridium tetani

<400> SEQUENCE: 23

Val Asp Asp Ala Leu Ile Asn Ser Thr Lys Ile Tyr Ser Tyr Phe Pro
1               5                   10                  15

Ser Val

<210> SEQ ID NO 24
<211> LENGTH: 15
<212> TYPE: PRT
<213> ORGANISM: Clostridium tetani

<400> SEQUENCE: 24

Gln Tyr Ile Lys Ala Asn Ser Lys Phe Ile Gly Ile Thr Glu Leu
1               5                   10                  15

<210> SEQ ID NO 25
<211> LENGTH: 21
<212> TYPE: PRT
<213> ORGANISM: Clostridium tetani

<400> SEQUENCE: 25

Phe Asn Asn Phe Thr Val Ser Phe Trp Leu Arg Val Pro Lys Val Ser
1               5                   10                  15

Ala Ser His Leu Glu
            20

<210> SEQ ID NO 26
```

```
<211> LENGTH: 11
<212> TYPE: PRT
<213> ORGANISM: Anaplasma marginale

<400> SEQUENCE: 26

Ser Ser Ala Gly Gly Gln Gln Gln Glu Ser Ser
1               5                   10

<210> SEQ ID NO 27
<211> LENGTH: 20
<212> TYPE: PRT
<213> ORGANISM: Plasmodium falciparum

<400> SEQUENCE: 27

Asp Glu Lys Lys Ile Ala Lys Met Glu Lys Ala Ser Ser Val Phe Asn
1               5                   10                  15

Val Val Asn Ser
            20

<210> SEQ ID NO 28
<211> LENGTH: 18
<212> TYPE: PRT
<213> ORGANISM: Infleunza HA B epitope

<400> SEQUENCE: 28

Ser Lys Ala Phe Ser Asn Cys Tyr Pro Tyr Asp Val Pro Asp Tyr Ala
1               5                   10                  15

Ser Leu

<210> SEQ ID NO 29
<211> LENGTH: 12
<212> TYPE: PRT
<213> ORGANISM: Artificial Sequence
<220> FEATURE:
<223> OTHER INFORMATION: Identified : PADRE
<220> FEATURE:
<221> NAME/KEY: misc_feature
<222> LOCATION: (3)..(3)
<223> OTHER INFORMATION: Xaa can be any naturally occurring amino acid

<400> SEQUENCE: 29

Ala Lys Xaa Val Ala Ala Trp Thr Leu Lys Ala Ala
1               5                   10

<210> SEQ ID NO 30
<211> LENGTH: 11
<212> TYPE: PRT
<213> ORGANISM: Concholepas concholepas

<400> SEQUENCE: 30

Leu Met Arg Lys Asp Val Asp Thr Leu Thr Asp
1               5                   10

<210> SEQ ID NO 31
<211> LENGTH: 7
<212> TYPE: PRT
<213> ORGANISM: Concholepas concholepas
<220> FEATURE:
<221> NAME/KEY: misc_feature
<222> LOCATION: (2)..(2)
<223> OTHER INFORMATION: Xaa can be any naturally occurring amino acid

<400> SEQUENCE: 31

Leu Xaa Arg Lys Asn Val Asp
1               5
```

<210> SEQ ID NO 32
<211> LENGTH: 386
<212> TYPE: PRT
<213> ORGANISM: Gallus gallus

<400> SEQUENCE: 32

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 33
<211> LENGTH: 607
<212> TYPE: PRT
<213> ORGANISM: Bos taurus

<400> SEQUENCE: 33

Met Lys Trp Val Thr Phe Ile Ser Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
            35                  40                  45

Ile Ala Phe Ser Gln Tyr Leu Gln Gln Cys Pro Phe Asp Glu His Val
        50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
            115                 120                 125

His Lys Asp Asp Ser Pro Asp Leu Pro Lys Leu Lys Pro Asp Pro Asn
        130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
        195                 200                 205

Arg Glu Lys Val Leu Ala Ser Ser Ala Arg Gln Arg Leu Arg Cys Ala
210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val

```
                355                 360                 365
Leu Leu Arg Leu Ala Lys Glu Tyr Glu Ala Thr Leu Glu Glu Cys Cys
    370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
        435                 440                 445

Val Ser Arg Ser Leu Gly Lys Val Gly Thr Arg Cys Cys Thr Lys Pro
    450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
        515                 520                 525

Leu Phe Thr Phe His Ala Asp Ile Cys Thr Leu Pro Asp Thr Glu Lys
    530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 34
<211> LENGTH: 124
<212> TYPE: PRT
<213> ORGANISM: Vibrio cholerae

<400> SEQUENCE: 34

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120
```

<210> SEQ ID NO 35
<211> LENGTH: 9
<212> TYPE: PRT
<213> ORGANISM: Cytomegalovirus

<400> SEQUENCE: 35

Asn Leu Val Pro Met Val Ala Thr Val
1               5

<210> SEQ ID NO 36
<211> LENGTH: 23
<212> TYPE: PRT
<213> ORGANISM: Rhipicephalus microplus

<400> SEQUENCE: 36

Pro Val Ser Thr Pro Ala Pro Thr Val Pro Arg Ser Asp Ser Ser
1               5                   10                  15

Ser Ser Gly Thr His Gly Val
            20

<210> SEQ ID NO 37
<211> LENGTH: 11
<212> TYPE: PRT
<213> ORGANISM: Rhipicephalus microplus

<400> SEQUENCE: 37

Thr Thr His Gly Asp Asn Gly Ala Ala Ala His
1               5                   10

<210> SEQ ID NO 38
<211> LENGTH: 29
<212> TYPE: PRT
<213> ORGANISM: Rhipicephalus microplus

<400> SEQUENCE: 38

Ile Arg Pro Ala Ser Val Thr Ser Ala Pro Thr Ala Pro Ser Pro Ala
1               5                   10                  15

Pro Thr Val Ala Ser Thr Val Pro Ser Ala Thr Thr Arg
            20                  25

<210> SEQ ID NO 39
<211> LENGTH: 18
<212> TYPE: PRT
<213> ORGANISM: Rhipicephalus microplus

<400> SEQUENCE: 39

Ile Arg Pro Ala Ser Val Thr Ser Ala Pro Thr Ala Pro Ser Pro Ala
1               5                   10                  15

Pro Thr

<210> SEQ ID NO 40
<211> LENGTH: 19
<212> TYPE: PRT
<213> ORGANISM: Rhipicephalus microplus

<400> SEQUENCE: 40

Thr Ala Pro Ser Pro Ala Pro Thr Val Ala Ser Thr Val Pro Ser Ala
1               5                   10                  15

Thr Thr Arg

<210> SEQ ID NO 41
<211> LENGTH: 48

```
<212> TYPE: PRT
<213> ORGANISM: Rhipicephalus microplus

<400> SEQUENCE: 41

Pro Phe Ala Pro Thr Val Leu Pro Thr Val Gly Ala Ala Ala Pro Thr
1               5                   10                  15

Val Arg Gly Pro Val Pro Arg Val Gly Thr Phe Pro Val Pro Ala Thr
            20                  25                  30

Thr Val Ala Ser Ala Asp Phe Pro Thr Ser Ala Pro Ala Asn Val Ser
        35                  40                  45

<210> SEQ ID NO 42
<211> LENGTH: 21
<212> TYPE: PRT
<213> ORGANISM: Rhipicephalus microplus

<400> SEQUENCE: 42

Pro Phe Ala Pro Thr Val Leu Pro Thr Val Gly Ala Ala Ala Pro Thr
1               5                   10                  15

Val Arg Gly Pro Val
            20

<210> SEQ ID NO 43
<211> LENGTH: 21
<212> TYPE: PRT
<213> ORGANISM: Rhipicephalus microplus

<400> SEQUENCE: 43

Pro Val Pro Ala Thr Thr Val Ala Ser Ala Asp Phe Pro Thr Ser Ala
1               5                   10                  15

Pro Ala Asn Val Ser
            20

<210> SEQ ID NO 44
<211> LENGTH: 23
<212> TYPE: PRT
<213> ORGANISM: Rhipicephalus australis

<400> SEQUENCE: 44

Pro Val Asn Thr Pro Ala Pro Thr Val Pro Pro Arg Ser Asp Ser Ser
1               5                   10                  15

Ser Ser Gly Thr His Val Gly
            20

<210> SEQ ID NO 45
<211> LENGTH: 11
<212> TYPE: PRT
<213> ORGANISM: Rhipicephalus australis

<400> SEQUENCE: 45

Thr Ala His Glu Asp Asn Gly Ala Ala Ala His
1               5                   10

<210> SEQ ID NO 46
<211> LENGTH: 10
<212> TYPE: PRT
<213> ORGANISM: Rhipicephalus microplus

<400> SEQUENCE: 46

Phe Pro Leu Gln Gly Glu Ala Tyr Thr Ile
1               5                   10
```

```
<210> SEQ ID NO 47
<211> LENGTH: 10
<212> TYPE: PRT
<213> ORGANISM: Rhipicephalus australis

<400> SEQUENCE: 47

Phe Pro Leu Gln Gly Glu Pro Thr Arg Ser
1               5                   10

<210> SEQ ID NO 48
<211> LENGTH: 12
<212> TYPE: PRT
<213> ORGANISM: Rhipicephalus microplus

<400> SEQUENCE: 48

Ser Ser Phe Ile Glu Gly Pro Arg Asp Glu Ile Glu
1               5                   10

<210> SEQ ID NO 49
<211> LENGTH: 12
<212> TYPE: PRT
<213> ORGANISM: Rhipicephalus australis

<400> SEQUENCE: 49

Ser Ser Phe Ile Glu Gly Pro Arg Asp Glu Ile Glu
1               5                   10

<210> SEQ ID NO 50
<211> LENGTH: 57
<212> TYPE: PRT
<213> ORGANISM: Rhipicephalus microplus

<400> SEQUENCE: 50

Phe Ser Asn Asn Lys Gly Tyr Asp His Lys Thr Gly Phe Ser Ala Ser
1               5                   10                  15

Asp Ser Lys Thr Phe Gly Ala Gly Gln Gln Gln Gly Ser Ala Gly Phe
            20                  25                  30

Gln Gly Gly Ala Ala Gly His Gln Ala Gly Phe Gly Gln Ser Ser His
        35                  40                  45

Gly His Thr Thr Gly Val Gly His Ala
    50                  55

<210> SEQ ID NO 51
<211> LENGTH: 21
<212> TYPE: PRT
<213> ORGANISM: Rhipicephalus microplus

<400> SEQUENCE: 51

Phe Ser Asn Asn Lys Gly Tyr Asp His Lys Thr Gly Phe Ser Ala Ser
1               5                   10                  15

Asp Ser Lys Thr Phe
            20

<210> SEQ ID NO 52
<211> LENGTH: 15
<212> TYPE: PRT
<213> ORGANISM: Rhipicephalus microplus

<400> SEQUENCE: 52

His Gln Gln Gly Ser Gly Ala Phe Thr Gly Gly Ser Ala His Arg
1               5                   10                  15

<210> SEQ ID NO 53
```

<211> LENGTH: 64
<212> TYPE: PRT
<213> ORGANISM: Rhipicephalus microplus

<400> SEQUENCE: 53

Ala Phe Lys Lys Thr Ser Ser Thr Pro Ser Ala Val Leu Glu Pro Pro
1               5                   10                  15

Gln Ser Phe Thr Val Thr Ala Pro Ser Gln Asp Pro Pro Leu Leu Asp
            20                  25                  30

Ala Ser Ser Gly Ser Ser Thr Leu Ala Pro Leu Ala Glu Ser Ala
        35                  40                  45

Pro Pro Thr Val Ser Thr Ser Val Ser Asn Asp Ala Glu Thr Thr Thr
    50                  55                  60

<210> SEQ ID NO 54
<211> LENGTH: 15
<212> TYPE: PRT
<213> ORGANISM: Rhipicephalus microplus

<400> SEQUENCE: 54

Trp Ser Ala Arg Ala Asn Asn Asn Gln Asp Ser Met Arg Gln Asp
1               5                   10                  15

<210> SEQ ID NO 55
<211> LENGTH: 34
<212> TYPE: PRT
<213> ORGANISM: Rhipicephalus microplus

<400> SEQUENCE: 55

Ala Phe Lys Lys Thr Ser Ser Thr Pro Ser Ala Val Leu Glu Pro Pro
1               5                   10                  15

Gln Ser Phe Thr Val Thr Ala Pro Ser Gln Asp Pro Pro Leu Leu Asp
            20                  25                  30

Ala Ser

<210> SEQ ID NO 56
<211> LENGTH: 21
<212> TYPE: PRT
<213> ORGANISM: Rhipicephalus microplus

<400> SEQUENCE: 56

Ala Phe Lys Lys Thr Ser Ser Thr Pro Ser Ala Val Leu Glu Pro Pro
1               5                   10                  15

Gln Ser Phe Thr Val
            20

<210> SEQ ID NO 57
<211> LENGTH: 21
<212> TYPE: PRT
<213> ORGANISM: Rhipicephalus microplus

<400> SEQUENCE: 57

Asp Pro Pro Leu Leu Asp Ala Ser Ser Gly Ser Ser Thr Leu Ala
1               5                   10                  15

Pro Leu Ala Glu Ser
            20

<210> SEQ ID NO 58
<211> LENGTH: 18
<212> TYPE: PRT
<213> ORGANISM: Rhipicephalus microplus

```
<400> SEQUENCE: 58

Ser Thr Ala Gln Lys Pro Cys Glu Gly Gly Glu Lys Asn Cys Thr
1               5                   10                  15

Gly Lys

<210> SEQ ID NO 59
<211> LENGTH: 11
<212> TYPE: PRT
<213> ORGANISM: Rhipicephalus microplus

<400> SEQUENCE: 59

Asp Arg Asn Glu Gly Gln Lys Cys Ser Gly Lys
1               5                   10

<210> SEQ ID NO 60
<211> LENGTH: 10
<212> TYPE: PRT
<213> ORGANISM: Rhipicephalus microplus

<400> SEQUENCE: 60

Ser Asn Gln Gln Gly Asn Arg Cys Thr Ser
1               5                   10

<210> SEQ ID NO 61
<211> LENGTH: 16
<212> TYPE: PRT
<213> ORGANISM: Rhipicephalus microplus

<400> SEQUENCE: 61

Gly His Tyr Thr Asp Thr Cys Asn Asp Arg Asn Cys His Pro Ser Thr
1               5                   10                  15

<210> SEQ ID NO 62
<211> LENGTH: 18
<212> TYPE: PRT
<213> ORGANISM: Rhipicephalus australis

<400> SEQUENCE: 62

Ser Thr Ala Gln Lys Pro Cys Glu Gly Gly Glu Lys Asn Cys Thr
1               5                   10                  15

Gly Lys

<210> SEQ ID NO 63
<211> LENGTH: 11
<212> TYPE: PRT
<213> ORGANISM: Rhipicephalus australis

<400> SEQUENCE: 63

Asp Arg Asn Glu Gly Gln Lys Cys Ser Gly Lys
1               5                   10

<210> SEQ ID NO 64
<211> LENGTH: 10
<212> TYPE: PRT
<213> ORGANISM: Rhipicephalus australis

<400> SEQUENCE: 64

Ser Asn Gln Gln Gly Asn Arg Cys Thr Ser
1               5                   10

<210> SEQ ID NO 65
<211> LENGTH: 16
<212> TYPE: PRT
```

```
<213> ORGANISM: Rhipicephalus australis

<400> SEQUENCE: 65

Gly Arg Tyr Thr Asp Ser Cys Asn Asp Arg Asn Cys His Pro Ser Thr
1               5                   10                  15

<210> SEQ ID NO 66
<211> LENGTH: 15
<212> TYPE: PRT
<213> ORGANISM: Rhipicephalus australis

<400> SEQUENCE: 66

Met Leu Arg Gly Ala Leu Ala Ala Ile Leu Leu Leu Ile Ser Ser
1               5                   10                  15

<210> SEQ ID NO 67
<211> LENGTH: 10
<212> TYPE: PRT
<213> ORGANISM: Rhipicephalus australis

<400> SEQUENCE: 67

Thr Phe Val Arg Ser Ala Ser Leu Pro Ala
1               5                   10

<210> SEQ ID NO 68
<211> LENGTH: 15
<212> TYPE: PRT
<213> ORGANISM: Rhipicephalus microplus

<400> SEQUENCE: 68

Met Leu Arg Gly Ala Leu Ala Ala Ile Leu Leu Leu Ile Ser Ser
1               5                   10                  15

<210> SEQ ID NO 69
<211> LENGTH: 10
<212> TYPE: PRT
<213> ORGANISM: Rhipicephalus microplus

<400> SEQUENCE: 69

Ser Phe Glu Arg Phe Ala Pro Pro Pro Asp
1               5                   10

<210> SEQ ID NO 70
<211> LENGTH: 12
<212> TYPE: PRT
<213> ORGANISM: Rhipicephalus microplus

<400> SEQUENCE: 70

Phe Thr Thr Tyr Asp Arg Asp Asn Asp Ala Ser Ala
1               5                   10

<210> SEQ ID NO 71
<211> LENGTH: 12
<212> TYPE: PRT
<213> ORGANISM: Rhipicephalus australis

<400> SEQUENCE: 71

Phe Ser Thr Tyr Asp Leu Asp Asn Asp Ala Ser Gly
1               5                   10

<210> SEQ ID NO 72
<211> LENGTH: 42
<212> TYPE: PRT
<213> ORGANISM: Rhipicephalus microplus
```

```
<400> SEQUENCE: 72

Ser Lys Phe Asp Cys Pro Pro Gly Gln His Phe Ser Pro Ala Asp Asn
1               5                   10                  15

Arg Cys Ala Thr Pro Glu Glu Ala Lys Cys Asp Pro Ala Phe Ala Asp
                20                  25                  30

Asn Asp Ala Thr Asp Asp Glu Ala Ile Asn
            35                  40

<210> SEQ ID NO 73
<211> LENGTH: 21
<212> TYPE: PRT
<213> ORGANISM: Rhipicephalus microplus

<400> SEQUENCE: 73

Ala Asp Asn Arg Cys Ala Thr Pro Glu Glu Ala Lys Cys Asp Pro Ala
1               5                   10                  15

Phe Ala Asp Asn Asp
            20

<210> SEQ ID NO 74
<211> LENGTH: 16
<212> TYPE: PRT
<213> ORGANISM: Rhipicephalus microplus

<400> SEQUENCE: 74

Asp Pro Ala Phe Ala Asp Asn Asp Ala Thr Asp Asp Glu Ala Ile Asn
1               5                   10                  15

<210> SEQ ID NO 75
<211> LENGTH: 42
<212> TYPE: PRT
<213> ORGANISM: Rhipicephalus australis

<400> SEQUENCE: 75

Ser Lys Phe Asp Cys Pro Pro Gly Gln His Phe Ser Pro Ala Asp Asn
1               5                   10                  15

Arg Cys Ala Thr Pro Glu Glu Ala Lys Cys Asp Pro Ala Phe Ala Asp
                20                  25                  30

Asn Asp Ala Thr Asp Asp Glu Ala Ile Asn
            35                  40

<210> SEQ ID NO 76
<211> LENGTH: 21
<212> TYPE: PRT
<213> ORGANISM: Rhipicephalus australis

<400> SEQUENCE: 76

Ala Asp Asn Arg Cys Ala Thr Pro Glu Glu Ala Lys Cys Asp Pro Ala
1               5                   10                  15

Phe Ala Asp Asn Asp
            20

<210> SEQ ID NO 77
<211> LENGTH: 16
<212> TYPE: PRT
<213> ORGANISM: Rhipicephalus australis

<400> SEQUENCE: 77

Asp Pro Ala Phe Ala Asp Asn Asp Ala Thr Asp Asp Glu Ala Ile Asn
1               5                   10                  15
```

```
<210> SEQ ID NO 78
<211> LENGTH: 24
<212> TYPE: PRT
<213> ORGANISM: Rhipicephalus microplus

<400> SEQUENCE: 78

Gly Ala Leu Thr Pro Glu Pro Thr Asn Thr Asn Ala Thr Ala Leu Pro
1               5                   10                  15

Val Pro Thr Pro Leu Pro Leu His
            20

<210> SEQ ID NO 79
<211> LENGTH: 19
<212> TYPE: PRT
<213> ORGANISM: Rhipicephalus microplus

<400> SEQUENCE: 79

Ser Pro Arg Arg Cys Lys Pro Leu Gly Lys Arg Gly Asp Pro Cys Ser
1               5                   10                  15

Pro Arg Ser

<210> SEQ ID NO 80
<211> LENGTH: 11
<212> TYPE: PRT
<213> ORGANISM: Rhipicephalus microplus

<400> SEQUENCE: 80

Cys Gly Pro Asn Glu Gly Thr Cys Glu Asp Gly
1               5                   10

<210> SEQ ID NO 81
<211> LENGTH: 23
<212> TYPE: PRT
<213> ORGANISM: Rhipicephalus microplus

<400> SEQUENCE: 81

Val Gly His Ala Ser Gly Val Gly Ala Pro Gly Leu Gly Val Val Gly
1               5                   10                  15

Asn Pro Gly Leu Val Gly Ala
            20

<210> SEQ ID NO 82
<211> LENGTH: 16
<212> TYPE: PRT
<213> ORGANISM: Rhipicephalus microplus

<400> SEQUENCE: 82

Val Gly His Ala Ser Gly Val Gly Ala Pro Gly Leu Gly Val Val Gly
1               5                   10                  15

<210> SEQ ID NO 83
<211> LENGTH: 21
<212> TYPE: PRT
<213> ORGANISM: Rhipicephalus microplus

<400> SEQUENCE: 83

Thr Ser Ala Gly Gly His Gln Ser Gly Tyr Gln Gly Gly Ala Ala Gly
1               5                   10                  15

His Asn Gln Gly Ser
            20

<210> SEQ ID NO 84
<211> LENGTH: 21
```

```
<212> TYPE: PRT
<213> ORGANISM: Rhipicephalus microplus

<400> SEQUENCE: 84

Ala Ala Gly His Asn Gln Gly Ser Gly Ala Phe Ala Gly Gly Ala Ser
1               5                   10                  15

Gly Ser Thr Val Asn
            20

<210> SEQ ID NO 85
<211> LENGTH: 21
<212> TYPE: PRT
<213> ORGANISM: Rhipicephalus microplus

<400> SEQUENCE: 85

Gly Ala Ser Gly Ser Thr Val Asn Ala Phe Lys Asn Asp Ala Gly Tyr
1               5                   10                  15

Ser His Ser Ser Gly
            20

<210> SEQ ID NO 86
<211> LENGTH: 10
<212> TYPE: PRT
<213> ORGANISM: Rhipicephalus microplus

<400> SEQUENCE: 86

Val Ser Leu Gly Glu Pro Gly Tyr Ile Gly
1               5                   10

<210> SEQ ID NO 87
<211> LENGTH: 42
<212> TYPE: PRT
<213> ORGANISM: Rhipicephalus microplus

<400> SEQUENCE: 87

Phe Gly Gly Gly Tyr Glu Asp Gly Tyr Gly Ala Ala His Gly Ala Val
1               5                   10                  15

Ala Gly Gly Asp Gln Ala Gly Phe Gln Lys Gly Ala Ala Gly His Ala
            20                  25                  30

Gln Gly Ser Gly Arg Tyr Ala Gly Gly Thr
        35                  40

<210> SEQ ID NO 88
<211> LENGTH: 21
<212> TYPE: PRT
<213> ORGANISM: Rhipicephalus microplus

<400> SEQUENCE: 88

Phe Gly Gly Gly Tyr Glu Asp Gly Tyr Gly Ala Ala His Gly Ala Val
1               5                   10                  15

Ala Gly Gly Asp Gln
            20

<210> SEQ ID NO 89
<211> LENGTH: 21
<212> TYPE: PRT
<213> ORGANISM: Rhipicephalus microplus

<400> SEQUENCE: 89

Gly Ala Val Ala Gly Gly Asp Gln Ala Gly Phe Gln Lys Gly Ala Ala
1               5                   10                  15

Gly His Ala Gln Gly
            20
```

<210> SEQ ID NO 90
<211> LENGTH: 16
<212> TYPE: PRT
<213> ORGANISM: Rhipicephalus microplus

<400> SEQUENCE: 90

Gly Ala Ala Gly His Ala Gln Gly Ser Gly Arg Tyr Ala Gly Gly Thr
1               5                   10                  15

<210> SEQ ID NO 91
<211> LENGTH: 15
<212> TYPE: PRT
<213> ORGANISM: Rhipicephalus microplus

<400> SEQUENCE: 91

Leu Phe Val Val Thr Val Phe Thr Leu Leu Ala Cys Ser Ala Thr
1               5                   10                  15

<210> SEQ ID NO 92
<211> LENGTH: 15
<212> TYPE: PRT
<213> ORGANISM: Rhipicephalus microplus

<400> SEQUENCE: 92

Leu Gly Gly Leu Gly Gly Ala Gly Leu Gly Gly Ala Gly Ile Val
1               5                   10                  15

<210> SEQ ID NO 93
<211> LENGTH: 19
<212> TYPE: PRT
<213> ORGANISM: Rhipicephalus microplus

<400> SEQUENCE: 93

Pro Gly Leu Val Gly Gly Gly Leu Gly Gln Gly Phe Gly Gln Gly Phe
1               5                   10                  15

Gln Ser Gly

<210> SEQ ID NO 94
<211> LENGTH: 97
<212> TYPE: PRT
<213> ORGANISM: Rhipicephalus microplus

<400> SEQUENCE: 94

Phe Gly Ser Ser Ala Gly Gly His Gln Gly Gly Phe Gln Gly Gly Ala
1               5                   10                  15

Gly Gly His Asn Leu Gly Ala Thr Gly Phe Ala Gly Gly Ala Ala Gly
                20                  25                  30

Ser Lys Val Asn Ser Tyr Asn Asp Asn Arg Gly Tyr Ser His Thr Ser
            35                  40                  45

Ser Phe Ser Ser Ser Asp Gly Lys Thr Phe Gly Thr Gly Asn Lys Gln
        50                  55                  60

Gly Ser Ser Gly Phe Gln Gly Ala Gly Gly His Gln Ala Gly Phe
65                  70                  75                  80

Gly Gln Ser Gly Phe Gly Ser Ala Gly Gly Val Ser Gly Gly Gly Leu
                85                  90                  95

Gly

<210> SEQ ID NO 95
<211> LENGTH: 21

```
<212> TYPE: PRT
<213> ORGANISM: Rhipicephalus microplus

<400> SEQUENCE: 95

Leu Gly Ala Thr Gly Phe Ala Gly Gly Ala Gly Ser Lys Val Asn
1               5                   10                  15

Ser Tyr Asn Asp Asn
            20

<210> SEQ ID NO 96
<211> LENGTH: 15
<212> TYPE: PRT
<213> ORGANISM: Rhipicephalus microplus

<400> SEQUENCE: 96

Leu Arg Val Thr Asp Met Phe Val Arg Val Arg Pro Leu Pro Ala
1               5                   10                  15

<210> SEQ ID NO 97
<211> LENGTH: 15
<212> TYPE: PRT
<213> ORGANISM: Rhipicephalus microplus

<400> SEQUENCE: 97

Val Val Ala Val Ala Ala Val Ser Val Val Ser Ser Gln Glu Leu
1               5                   10                  15

<210> SEQ ID NO 98
<211> LENGTH: 15
<212> TYPE: PRT
<213> ORGANISM: Rhipicephalus microplus

<400> SEQUENCE: 98

Met Ile Ser Ile Val Val Phe Val Gly Leu Ala Ser Leu Ala Gly
1               5                   10                  15

<210> SEQ ID NO 99
<211> LENGTH: 660
<212> TYPE: PRT
<213> ORGANISM: Rhipicephalus microplus

<400> SEQUENCE: 99

Met Ala Ala Arg Ser Gly Ser Ser Ala Ala Asp Arg Phe Val Ala Val
1               5                   10                  15

Ala Leu Leu Ala Thr Ala Leu Tyr Ala Thr Ala Ala Asp Asn Phe
                20                  25                  30

Asp Thr Tyr Leu Ala Thr Leu Ser Asn Val Ser Ala Leu Ile Lys Asp
            35                  40                  45

Glu Ala Met Gly Val Ala Phe Ile Glu Gly Leu Asn Asp Pro Tyr Thr
        50                  55                  60

Thr Ile Asn Asn Val Asp Ser Ser Ser Trp Asp Tyr Ala Ser Asn
65                  70                  75                  80

Ile Thr Asp Tyr Asn Gln Asn Met Ser Asn Lys Val Ser Thr Glu Val
                85                  90                  95

Ser Lys Met Glu Arg Gln Phe Gly Ile Thr Ala Lys Arg Phe Asp Trp
            100                 105                 110

His Asn Phe Lys Asn Asp Ser Leu Lys Arg Leu Phe Arg His Val Ala
        115                 120                 125

Thr Ile Gly Leu Ala Ala Leu Pro Asp Asp Lys Leu Glu Asn Ala Thr
    130                 135                 140
```

```
Ser Leu Ser Ser Lys Met Ala Ala Ile Tyr Gly Ser Thr Lys Val Thr
145                 150                 155                 160

Val Gly Lys Asp Lys Asp Leu Pro Leu Glu Pro Asp Leu Thr Arg Asn
                165                 170                 175

Met Lys Glu Val Gly Asn Tyr Asp Lys Leu Leu Gln Thr Trp Leu Ala
            180                 185                 190

Trp His Asn Ala Val Gly Pro Ala Ile Lys Gln Tyr Tyr Ile Pro Tyr
        195                 200                 205

Ile Lys Leu Ser Asn Glu Ala Ala Ser Leu Asp Gly Tyr Asp Asn Ile
    210                 215                 220

Lys Ser Ala Trp Leu Ser Asp Tyr Glu Thr Glu Asn Met Thr Glu Ile
225                 230                 235                 240

Val Asp Lys Leu Trp Glu Asp Leu Ser Pro Leu Tyr Lys Lys Leu His
                245                 250                 255

Ala Tyr Val Arg Met Lys Leu Arg Glu Ile Tyr Pro Gly Arg Leu Pro
            260                 265                 270

Glu Asp Gly Thr Ile Pro Ala His Leu Leu Gly Asn Met Trp Ala Gln
        275                 280                 285

Glu Trp Gly Thr Leu Tyr Pro His Leu Thr Met Glu Asp Lys Pro Leu
    290                 295                 300

Asp Ile Ser Lys Thr Met Val Glu Gln Lys Trp Asp Ala Gln Lys Met
305                 310                 315                 320

Phe His Ala Ala Glu Asp Phe Phe Thr Ser Leu Gly Leu Asp Asn Met
                325                 330                 335

Thr Ser Glu Phe Trp Ser Lys Ser Ile Leu Thr Lys Pro Glu Asp Arg
            340                 345                 350

Glu Ile Gln Cys His Ala Ser Ala Trp Asn Met Tyr Asn Gly Asp Asp
        355                 360                 365

Phe Arg Ile Lys Met Cys Thr Asp Pro Ser Val Glu Glu Leu Arg Thr
    370                 375                 380

Val His His Glu Met Gly His Ile Glu Tyr Tyr Met Gln Tyr Lys His
385                 390                 395                 400

Leu His Val Leu Leu Gln Glu Gly Ala Asn Glu Gly Phe His Glu Ala
                405                 410                 415

Val Gly Asp Leu Ile Ala Leu Ser Val Ala Thr Lys Thr His Tyr Gly
            420                 425                 430

Lys Leu Ser Leu Leu Lys Pro Thr Asp Lys Tyr Asn Ala Val Asp Leu
        435                 440                 445

Leu Leu Met Ser Ala Leu Asp Lys Ile Ala Phe Leu Pro Phe Gly Tyr
    450                 455                 460

Leu Leu Asp Lys Trp Arg Trp Thr Ile Phe Thr Gly Glu Thr Pro Phe
465                 470                 475                 480

Asp Lys Met Asn Glu Lys Phe Trp Glu Tyr Arg Ile Lys Tyr Gln Gly
                485                 490                 495

Val Ser Pro Pro Val Lys Arg Asn Glu Ser Phe Phe Asp Gly Gly Ala
            500                 505                 510

Lys Tyr His Val Ala Leu His Val Pro Tyr Leu Arg Tyr Phe Val Ala
        515                 520                 525

Phe Ile Leu Gln Phe Gln Phe His Glu His Leu Cys Thr Val Ala Lys
    530                 535                 540

Lys Val Asp Glu His His Pro Phe His Glu Cys Asp Ile Tyr Gly Glu
545                 550                 555                 560

Lys Asn Ala Gly Asp Val Leu Lys Lys Gly Leu Ser Leu Gly Arg Ser
```

```
                    565                 570                 575
Lys Pro Trp Pro Asp Val Leu Glu Ile Met Ala Gly Thr Arg Gln Met
                580                 585                 590

Ser Ala Ser Ser Leu Lys Lys Tyr Tyr Glu Pro Leu Glu Lys Trp Leu
            595                 600                 605

Asp Glu Arg Ile Lys Asn Glu Val Val Gly Trp Asp Lys Ala Asn Val
        610                 615                 620

Gln Asp Tyr Met Gly Val Pro Ser Phe Ala Asn Lys Val Asp Phe Ser
625                 630                 635                 640

Ala Ala Ala Val Leu Ala Ser Ile Gly Val Ile Leu Phe Cys Trp Lys
                645                 650                 655

Asn Ile Ser Leu
            660

<210> SEQ ID NO 100
<211> LENGTH: 45
<212> TYPE: PRT
<213> ORGANISM: Rhipicephalus microplus

<400> SEQUENCE: 100

Cys Leu Ser Lys His Val Leu Arg Lys Leu Gln Ala Cys Glu His Ser
1               5                   10                  15

Ser Ile Cys Ser Asp Phe Gly Asn Glu Phe Cys Arg Asn Ala Cys Asp
            20                  25                  30

Cys Gly Glu Trp Gly Ala Met Asn Met Thr Thr Arg Cys
        35                  40                  45

<210> SEQ ID NO 101
<211> LENGTH: 45
<212> TYPE: PRT
<213> ORGANISM: Rhipicephalus microplus

<400> SEQUENCE: 101

Cys Leu Ser Lys His Val Leu Arg Lys Leu Gln Ala Cys Glu His Cys
1               5                   10                  15

Asp Cys Gly Glu Trp Gly Ala Met Asn Met Thr Thr Arg Ser Ser Ile
            20                  25                  30

Cys Ser Asp Phe Gly Asn Glu Phe Cys Arg Asn Ala Cys
        35                  40                  45

<210> SEQ ID NO 102
<211> LENGTH: 51
<212> TYPE: PRT
<213> ORGANISM: Rhipicephalus microplus

<400> SEQUENCE: 102

Cys Leu Ser Lys His Val Leu Arg Lys Leu Gln Ala Cys Glu His Lys
1               5                   10                  15

Glu Lys Ser Ser Ile Cys Ser Asp Phe Gly Asn Glu Phe Cys Arg Asn
            20                  25                  30

Ala Lys Glu Lys Cys Asp Cys Gly Glu Trp Gly Ala Met Asn Met Thr
        35                  40                  45

Thr Arg Cys
    50

<210> SEQ ID NO 103
<211> LENGTH: 14
<212> TYPE: PRT
<213> ORGANISM: Rhipicephalus microplus
```

<400> SEQUENCE: 103

Pro Asp Met Met Asp Phe Val Arg Ser Asn Gly Pro Met Thr
1               5                   10

<210> SEQ ID NO 104
<211> LENGTH: 693
<212> TYPE: DNA
<213> ORGANISM: Rhipicephalus microplus

<400> SEQUENCE: 104

```
atgcattctg actacgtgtt gtggaatgtc gtactatttg tcgttatggt tgccacaagt      60
acagctcaaa aaccatgcga aggaggtggt gaaaaaaatt gcacaggaaa agaaaaatgg     120
tgtttggttg atgagaatgg aggtgttcac gaaaagtgtc gcgacttgga ttgtagttct     180
tcaagatttt cctgttggtt tcaatgcgaa ggggatacaa cactggcctg ccataaaagc     240
cccacggacg atatatgcat atgctcatgc gtgaaaaact tttgcgacag gaatgagggc     300
cagaaatgca gcggtaaaac aaaatggtgc tttaatgaaa cagcaggctt cactgaaatg     360
tgtggtgagt caggttgcga tgcctcaaaa agtcactgga agtttgcaa  acacctggt      420
accgagatgt cctgcgagaa ggcctcagac agtgatgcat gccactgcac ctgcgtggaa     480
agagtttgca gtaaccaaca aggaaacaga tgcaccagca acaaaatgaa atggtgtata     540
atcagtgaca aaggacgcta tactgactct tgtaatgacc ggaattgcca cccttcaaca     600
ctcccgtgga aaatttgcta tagacgtgat tataagccgt cttgccgaaa gacgacccct     660
ggtacttgcc tgtgcacctg tgtgaaaggc taa                                  693
```

<210> SEQ ID NO 105
<211> LENGTH: 775
<212> TYPE: DNA
<213> ORGANISM: Rhipicephalus microplus

<400> SEQUENCE: 105

```
atgaagtttt tcgcaacagt cactctcctt gcactcgtgg caagtgctgc gttcgccgaa      60
gaggatgcca agaaagttga agaaggaa gataagaagg acgtcgaagg acgtggcgga     120
tttttgggag gcggacccgg ctttggtgtc ggcgtggttc ctggtgtcgt aggcagcccc     180
ggtgtcgttg gtcctggagt tgtcgccaac cccgcactgg taggagccgg tgtcggccac     240
ggcgtcggcc acggcgtcgg ccacggcgtc ggcttgggag cagttggtgt cggccacggt     300
gtcggccccg gtgtcggctt gggcggagtt ggcgttggcc acggaggcgg cttccagaca     360
ggttttggta caagcactgg agcacagcag gcgggcttcc agagaggcgc tgctggacac     420
cagcaaggat ccgagccctt cacaggggt tcagctcaca ggactgttaa cgccttcagc     480
aacaacaagg gctacgacca caagaccggc ttttcagctt ccgatagcaa gacctttgga     540
gcaggccaac agcagggatc tgcgggtttc cagggaggtg ccgctggaca tcaggctgga     600
ttcgggcagt cgtctcacgg ccatactacc ggtgtcggcc acgcgggtgt cggcgttgtc     660
ggctgagagc tccgcagttc aagcttcgtc tccttttgtc atcacacccc agtgcttggc     720
agttctgtca ttgcaagaag aaagatttca ataaaatgca caacctttt tgaaa          775
```

<210> SEQ ID NO 106
<211> LENGTH: 882
<212> TYPE: DNA
<213> ORGANISM: Rhipicephalus microplus

<400> SEQUENCE: 106

-continued

```
tctaatacga ctcactatag ggcaagcagt ggtatcaacg cagagtacat ggggcacgga      60
ggtcgctcat ctgctgccgt gcacgagaca cattttttgag gaactcgcag ccgcatcgac   120
aaccaagatg gtcaattcga aagtcgtggt caacggggtg gcagtggtcg cggtcgtcgt   180
catggttgtt gtgtccgtgg tcgtgccggt agtccaggga aagcccaagg ccagcagtgg   240
tggaccagcg gccggcgccc cggacttctc gaagttcttg gaccacctc ttcccagcga    300 ggactgcgtg ggtgtggtgg ccgccccagg tgctgccgcc ctggtggccg acccgaacga   360
ctgcaccaag tactccgtgt gctcggagac gttcagctcg aagttcgact gcccacccgg   420
ccagcacttc agcccggccg acaacagatg cgcgaccccg gaggaggcca agtgcgaccc   480
cgcttttgcc gacaacgatg ccaccgacga cgaagcaatc aacgtcgatg tgaagtccgt   540
tgctgtcgat gtcgttgacg ctgccgacgt ggagggtgat gccgccaaca tcatcgccac   600
cgatgtctaa acattcggtc tgcaccgcac gctggctgtg tgtgcacgca agtaccgaca   660
tcttgtctat actcgacgac caccttcgct ggagacgtgc gtgaaacagg gccacacatt   720
acggaacaag gatgcccatg gattccttct tagcctccga gatacctgtt gcaaagaaat   780
aaaagcgatg gtgttgtgtg ttcctgaaat aaaaaaaaaa aaaaaaaaaa aaaaaagtac   840
tctgcgttga taccactgct tgccctatag tgagtcgtat ta                      882
```

<210> SEQ ID NO 107
<211> LENGTH: 816
<212> TYPE: DNA
<213> ORGANISM: Rhipicephalus microplus

<400> SEQUENCE: 107

```
atggcacgtg aaattgttct tgtctgcatg atcgctgccg tggcaagaac cgcactgtcg    60
gcaccgaaag ctagagtttc tagaaagaat attcaagatc gcatacagca gttagcgaag   120
gacttcgagg ctcatcttca agatgcctcc atgcctcgac attgcgctga attgcttgaa   180
aacggccaac acataagcgg agtgtacacc atcttccacg aggctgctgg aacttcgggg   240
caagatgtat actgtgacat ggacactgac gacggaggat ggacagtcat tcaacgccgt   300
gggcagtacg gacacaatgc ttactacttt taccggaact ggactgagta cgccaatggt   360
ttcggaaacc cagctgatga gtactggatt ggtaacaaag cgctgcacgc cctcacgtca   420
ggagacgagg aaatggtact gcgaatcgta ttgagcaaca gcactgaaga tagcacgtat   480
ttcgattaca agactttcac cgttgcaagt gaacaacaac tgtttcaact acgcatagga   540
aatttttcgg aaatgacagg tgaccctatg gaaagactttt caggccagaa attcacaacc   600
tacgatcgtg acaatgatgc ctcggcgttc aactgcgctg agcgcttgcg tggtgcctgg   660
tggtacatcc tctgtgacga cagtaacctc aacggactca acttgaatgg ccaccatgac   720
agctccgggg atggtattgt gtgggaaggt acgtcttcgg acgcggcgca ctactcttac   780
ccgaaagttg aaatgatgat ccgaccagcg aaatag                             816
```

IMMUNOSTIMULATING COMPOSITIONS AND USES THEREFORE

FIELD OF THE INVENTION

This invention relates generally to methods and compositions for stimulating immune responses. More particularly, the present invention relates to compositions comprising one or more polypeptides for eliciting an immune response in a subject. The present invention further relates to the use of these compositions for treating or preventing tick infestation.

RELATED APPLICATIONS

This application is a national phase application under 35 U.S.C. § 371 of International Application No. PCT/AU2018/050080, filed Feb. 6, 2018, which claims priority from Australian provisional application No. AU 2017900358, filed Feb. 6, 2017, the contents of each of which are hereby incorporated by reference in their entirety.

Pursuant to 37 C.F.R. 1.821(c), a sequence listing is submitted herewith as an ASCII compliant text file named "FPAPP0010S_ST.25.txt", created on Aug. 2, 2019 and having a size of ~127 kilobytes. The content of the aforementioned file is hereby incorporated by reference in its entirety.

BACKGROUND OF THE INVENTION

Beef exports contribute approximately $4.5 billion to the Australian economy (2010-2011). The control of cattle ticks is vital to the continued success of the cattle industry in terms of compliance with regulatory protocols for domestic and international livestock movement and to enhance animal welfare through avoiding stress and debilitation. These ticks transmit protozoan (*Babesia bovis* and *B. bigemina*) and bacterial (*Anaplasma marginale*) organisms which cause babesiosis and anaplasmosis ("tick fever"). The tick-disease complex is the most important affecting world-wide livestock production (deCastro, 1997), leading to severe economic losses in dairy and beef production and restriction in traffic of animals costing >$US22-30 billion annually (Lew-Tabor and Rodriguez Valle, 2016). For example, cattle industries in northern Australia incur approximately $175 million in annual losses, due to the impact of ticks (see, Playford et al., 2005).

Cattle are particularly susceptible when they first encounter ticks, but some individuals and breeds develop a degree of resistance after repeated exposure. *Bos indicus* cattle and crosses (tropical breeds which predominate in northern Australia) develop stronger resistance than do *Bos taurus* cattle (British & European breeds). Chemical treatments (acaricides) are used to control ticks, however ticks have developed resistance to most current acaricides, and there is a market imperative to reduce chemical residues in both cattle and the environment. An efficacious vaccine would allow the tick line to be diminished and minimize the use of synthetic acaricides applied to treat cattle for ticks, thereby decreasing chemical footprints in milk, meat and the environment.

The previously available tick vaccine (TICKGARD PLUS) was based on a concealed tick gut antigen Bm86, which was not boosted during natural tick challenge (Rand et al., 1989) was not effective against ticks from different geographical locations (Garcia-Garcia et al., 1999). As successful administration of TICKGARD PLUS requires three or four booster shots per year, it was subsequently poorly adopted and is now no longer manufactured commercially.

The cost for control of babesiosis in Australia is approximately $28 million (Lew-Tabor and Rodiguez Valle, 2016). It has been estimated that 80% of the world population of 1,200 million cattle is at risk of ticks and tick-borne disease and global losses amount to around US$22-30 billion. Around 500 million cattle are exposed to babesiosis worldwide, and mortality rates of around 50% is common when susceptible cattle are imported into endemic areas. The cattle tick, *Rhipicephalus* (*Boophilus*) *microplus* is a major problem for cattle producers because of the direct effects of infestation and the diseases transmitted. Control of cattle ticks is required to ensure compliance with regulatory protocols for interstate and international livestock movement and to enhance animal welfare through avoiding stress and debilitation.

The application of traditional acaricides to control ticks has led to a rise in drug resistance problems among different regional populations of *R. microplus*. In Australia, for example, there are tick populations resistant to synthetic pyrethroids, amitraz and flumethren. There is also a need to develop less toxic chemicals for the control of tick infestations. In the case of tick-borne disease caused by *Babesia* species, there is only one drug currently registered for use.

There is a need for new treatments and compositions for preventing or reducing the incidence of tick infestations in livestock populations.

SUMMARY OF THE INVENTION

The present invention is predicated in part on the discovery of immunostimulatory molecules that elicit significant cellular and/or humoral immune responses. The identified polypeptide antigens have utility in therapeutic and prophylactic applications for combating tick infestations, as described hereafter.

Accordingly, in one aspect, the present invention provides immunostimulatory compositions that comprise at least one immunogen in the form of a polypeptide antigen that comprises, consists of or consists essentially of an amino acid sequence that corresponds to at least a portion of a tick polypeptide.

More specifically, the invention provides for a composition comprising:
  a recombinant or synthetic polypeptide comprising, consisting of, or consisting essentially of at least one polypeptide with an amino acid sequence corresponding to a tick polypeptide selected from TC12130, MPAAN50tr, MPAA730tr, TC12142, TC10097, TC9753, TC13011, TC8992, and TC5995 or fragments or variants thereof;
  an adjuvant for potentiating an immune response to the polypeptide.

The composition preferably comprises or consists of at least one of the polypeptides selected from TC12142, TC9753, TC8992 and TC5995, or fragments or variants thereof.

In any embodiment of the invention, the polypeptide in the composition may include an immunogenic polypeptide, or immunogenic fragment or variant thereof, selected from: TC12130 (for example, as set forth in SEQ ID NO: 1), MPAAN50tr (for example, as set forth in SEQ ID NO: 3), MPAA730tr (for example, as set forth in SEQ ID NO: 5), TC12142 (for example, as set forth in SEQ ID NO: 7), TC10097 (for example, as set forth in SEQ ID NO: 9), TC9753 (for example, as set forth in SEQ ID NO: 10)

TC13011 (for example, as set forth in SEQ ID NO: 12), TC8992 (for example, as set forth in SEQ ID NO: 14), and TC5995 (for example, as set forth in SEQ ID NO: 16), as further described herein.

In any embodiment of the invention, the composition comprises at least two polypeptides, at least three polypeptides, at least four polypeptides, at least five polypeptides, at least six polypeptides, at least seven polypeptides, at least eight polypeptides or all nine polypeptides, wherein the immunogens are polypeptides comprise polypeptides, fragments or variants thereof, in the group consisting of: TC12130, MPAAN50tr, MPAA730tr, TC12142, TC10097, TC9753, TC13011, TC8992, and TC5995.

It will be appreciated that where the compositions described herein comprise more than one polypeptide, the polypeptides can be provided as part of a single recombinant protein, or alternatively as multiple, individual polypeptide molecules.

Preferably, the composition at least comprises the polypeptides, or variants or fragments thereof, selected from: TC12142, TC9753, TC5995 and TC8992 and may further comprise additional polypeptides, or components for eliciting an immune response in a subject to a tick antigen.

In one preferred embodiment, the recombinant or synthetic polypeptide in the composition consists of the polypeptide TC12142 (SEQ ID NO: 7), or a fragment or variant thereof.

In another preferred embodiment, the recombinant or synthetic polypeptide in the composition consists of the polypeptide TC9753 (SEQ ID NO: 10), or a fragment or variant thereof.

In another preferred embodiment, the recombinant or synthetic polypeptide in the composition consists of the polypeptide TC5995 (SEQ ID NO: 16), or a fragment or variant thereof.

In still another preferred embodiment, the recombinant or synthetic polypeptide in the composition consists of the polypeptide TC8992 (SEQ ID NO: 14) or a fragment or variant thereof.

More preferably, the composition comprises at least two of the polypeptides TC12142, TC9753, TC5995 and TC8992, including fragments or variants thereof, or at least three of the polypeptides TC12142, TC9753, TC5995 and TC8992 including fragments or variants thereof, or all four of the polypeptides TC12142, TC9753, TC5995 and TC8992, or fragments or derivatives thereof.

Preferably, the adjuvant for use in the compositions described herein is selected from Freund's adjuvant (complete or incomplete), a saponin adjuvant (such as Quil-A) or a mineral oil adjuvant (such as the Montanide® series of adjuvants).

It will be understood that the immunostimulatory compositions described herein may further comprise one or more additional immunogens, wherein the immunogen is one that is not recited in the list above. Preferably, the additional immunogen is one which is useful for eliciting an immune response in a subject to a tick, thereby minimizing or reducing tick infestation in the subject. For example, the immunogen may include the antigen Bm86, as further described herein.

In some embodiments, the recombinant or synthetic polypeptides of the above compositions are provided in the form of at least one polypeptide antigen as described above, conjugated to a carrier protein which suitably comprises at least one T-cell epitope. One such preferred carrier protein is the Keyhole Limpet Hemocyanin (KLH) carrier protein (SEQ ID NO: 18).

In certain embodiments, the polypeptides having utility in the compositions and methods of the invention, correspond to at least an immunogenic fragment (portion) or variant of the aforementioned immunogenic polypeptides. For example, in some embodiments, the polypeptide corresponds to at least a portion of the tick polypeptide TC12130 with the native amino acid sequence as set forth in SEQ ID NO: 1 or any of the variants or fragments of TC12130 set out in Table 1.

In specific embodiments, the polypeptide antigen may comprise, consist, or consist essentially of one or both of the amino acid sequences PVSTPAPTVPPRSDSSSSGTHGV (SEQ ID NO: 36 corresponding to residues 123-145 of SEQ ID NO: 1) and TTHGDNGAAAH (SEQ ID NO: 37 corresponding to residues 178-188 of SEQ ID NO: 1).

In some of the same embodiments or in other embodiments, the polypeptide antigen corresponds to at least a portion of the tick polypeptide MPAAN50tr with the native amino acid sequence as set forth in SEQ ID NO: 3. For example, the polypeptide antigen may comprise, consist, or consist essentially of the amino acid sequence FPLQGEPTRS (corresponding to residues 311-320 of SEQ ID NO: 3).

In some of the same embodiments or in other embodiments, the polypeptide antigen corresponds to at least a portion of the tick polypeptide MPAA730tr with the native amino acid sequence as set forth in SEQ ID NO: 5. For example, the polypeptide antigen may comprise, consist, or consist essentially of the amino acid sequence SSFIEGPRDEIE (SEQ ID NO: 48 corresponding to residues 265-276 of SEQ ID NO: 5).

In some of the same embodiments or in other embodiments, the polypeptide antigen corresponds to at least a portion of the tick polypeptide TC12142 with the native amino acid sequence as set forth in SEQ ID NO: 7. For example, the polypeptide antigen may comprise, consist, or consist essentially of one or both of: the predicted B-cell amino acid epitope amino acid sequences peptides of TC12142 as set out in Table 1.

In some specific embodiments, the polypeptide antigen comprises, consists or consists essentially of the amino acid sequence FSNNKGYDHKTGFSASDSKTF (SEQ ID NO: 51 corresponding to residues 159-179 of SEQ ID NO: 7).

In some of the same embodiments or in other embodiments, the polypeptide antigen corresponds to at least a portion of the tick polypeptide TC10097 with the native amino acid sequence as set forth in SEQ ID NO: 9. For example, the polypeptide antigen may comprise, consist, or consist essentially of one or both of the predicted B-cell epitope amino acid sequences derived from TC10097 as set out in Table 1.

In some of the same embodiments or in other embodiments, the polypeptide antigen corresponds to at least a portion of the tick polypeptide TC9753 with the native amino acid sequence as set forth in SEQ ID NO: 10. In an exemplary embodiment of this type, the polypeptide antigen may comprise, consist, or consist essentially of at least one of the amino acid sequences derived from TC9753 as set out in Table 1.

In specific embodiments the polypeptide antigen comprises, consists, or consists essentially of the amino acid sequence STAQKPCEGGGEKNCTGK (SEQ ID NO: 58 corresponding to residues 20-37 of SEQ ID NO: 10).

In some of the same embodiments or in other embodiments, the polypeptide antigen corresponds to at least a portion of the tick polypeptide TC13011 with the native amino acid sequence as set forth in SEQ ID NO: 12. In an exemplary embodiment of this type, the polypeptide antigen comprises, consists, or consists essentially of the amino acid sequence SFERFAPPPD (SEQ ID NO: 69 corresponding to residues 137-146 of SEQ ID NO: 12). In some of the same and other embodiments the polypeptide antigen comprises, consists or consists essentially of the amino acid sequence MLRGALAAILLLISS (SEQ ID NO: 68 corresponding to residues 1-15 of SEQ ID NO: 12), which is a T cell epitope as recognized by the major histocompatibility complex class II cell surface receptor HLA DRB1*0101.

In some of the same embodiments or in other embodiments, the polypeptide antigen corresponds to at least a portion of the tick polypeptide TC8992 with the native amino acid sequence as set forth in SEQ ID NO: 14. For example, the polypeptide antigen may comprise, consist, or consist essentially of the amino acid sequence FTTYDRDN-DASA (SEQ ID NO: 70 corresponding to residues 198-209 of SEQ ID NO: 14).

In some of the same embodiments or in other embodiments, the polypeptide antigen corresponds to at least a portion of the tick polypeptide TC5995 with the native amino acid sequence as set forth in SEQ ID NO: 16. For example, the polypeptide antigen may comprise, consist, or consist essentially of the amino acid sequence SKFDCPPGQHFSPADNRCATPEEAKCDPAFADN-DATDDEAIN (SEQ ID NO: 72 corresponding to residues 91-132 of SEQ ID NO: 16) or an immunogenic fragment thereof (for example, ADNRCATPEEAKCDPAFADND (i.e., SEQ ID NO: 73 amino acid residues 104-124 of SEQ ID NO: 16) and DPAFADNDATDDEAIN (i.e., SEQ ID NO: 74 amino acid residues 117-132 of SEQ ID NO: 16)).

In any embodiment of the invention, the compositions may comprise any one or more of the above mentioned polypeptides or peptides (or variants or fragments thereof), in combination with one or more T-cell epitopes. It will be appreciated that the combination may be in the form of two or more polypeptides provided on different protein molecules within the composition, or alternatively, any peptide or polypeptide described above, conjugated to a T-cell epitope including via a linker peptide.

In some embodiments where the polypeptide antigen comprises a T-cell epitope, the composition may further comprise one or more promiscuous T-cell helper epitopes. By way of an example, promiscuous T-cell helper epitopes that can be used with the present invention include those having an amino acid sequence selected from SEQ ID NOs: 21, 22, 23, 24, 25, 26, 27, 28, 29 and 35. The polypeptide antigen may be encoded by a nucleic acid molecule that also encodes a promiscuous T-cell helper epitope. In some embodiments, the compositions may include more than one (i.e., a plurality) of promiscuous T-cell helper epitopes, optionally conjugated or otherwise linked to one another.

In some embodiments, the compositions further comprise an adjuvant. For example, oil adjuvants (including water in oil (w/o) adjuvants and water in oil in water (w/o/w) adjuvants are particularly suitable for livestock (e.g., cattle) immunization. By way of an example, the Freund's adjuvant, the Montanide® series of adjuvants and saponin adjuvants are suitable adjuvants for formulating with the compositions of the present invention.

In some embodiments, the compositions further comprise a pharmaceutically acceptable carrier, excipient, or diluent.

In another aspect, the present invention provides nucleic acid compositions, wherein the nucleic acid compositions comprise a nucleic acid construct comprising a polynucleotide encoding a polypeptide as described above. Preferably, the polynucleotide is operably connected to a regulatory polynucleotide, enabling expression of the polypeptide.

In some embodiments, the present invention provides a construct system for eliciting an immune response to a tick polypeptide, wherein the construct system comprises: a first nucleic acid construct comprising a first coding sequence that encodes a first polypeptide antigen comprising an amino acid sequence that corresponds to at least a portion of the tick polypeptide; and a second nucleic acid construct comprising a second coding sequence that encodes second polypeptide antigen comprising an amino acid sequence that corresponds to at least a portion of the tick polypeptide and that is operably connected to a third coding sequence that encodes a ubiquitin polypeptide; wherein the first nucleic acid construct and the second nucleic acid construct are operably linked to a common regulatory polynucleotide or to a different regulatory polynucleotide; and wherein the tick polypeptide is selected from TC12130, MPAAN50tr, MPAA730tr, TC12142, TC10097, TC9753, TC13011, TC8992, and TC5995.

In some embodiments, the first nucleic acid construct and/or the second nucleic acid construct is codon optimised to permit enhanced expression of an antigen encoded thereby in a target cell. In some embodiments, the first nucleic acid construct and/or the second nucleic acid construct is codon optimised to permit high expression of encoded antigen in a target cell than in another cell. In some embodiments, at least about 70%, 75%, 80%, 85%, 90%, 95%, or 100% (or any percentage integer in between) of the wild-type codons are codon optimized.

In any embodiment of the invention the compositions described herein, further comprise a pharmaceutically acceptable carrier, excipient, or diluent.

In another aspect, the present invention provides a method of eliciting an immune response to a tick polypeptide in a subject (e.g, a mammal, preferably livestock), the method comprising administering to the subject an effective amount of at least one polypeptide antigen with an amino acid sequence that corresponds to at least a portion of a tick polypeptide, or an effective amount of a polynucleotide from which the polypeptide is expressible, wherein the tick polypeptide is selected from TC12130, MPAAN50tr, MPAA730tr, TC12142, TC10097, TC9753, TC13011, TC8992, and TC5995. Preferably, the tick polypeptide is selected from TC12142, TC9753, TC5995 and TC8992. In some embodiments, at least two, at least three or all four peptides TC12142, TC9753, TC5995 and TC8992 are used in the method. Preferably, the polypeptide is administered in conjunction with an adjuvant for potentiating the immune response to the tick polypeptide. More preferably, the adjuvant is selected from Freund's adjuvant (complete or incomplete), a saponin or a mineral oil adjuvant.

In some embodiments, the method elicits in the subject one or both of a humoral immune response and a cellular immune response. In some embodiments, the cellular immune response is a $CD4^+$ immune response.

In yet another aspect, the present invention provides a method of treating a subject (e.g., livestock) with a tick infestation, the method comprising administering to the subject an effective amount of a composition that comprises at least one polypeptide antigen with an amino acid sequence corresponding to at least a portion of a tick polypeptide, or a polynucleotide from which the polypeptide is expressible, wherein the tick polypeptide is selected from TC12130, MPAAN50tr, MPAA730tr, TC12142, TC10097, TC9753, TC13011, TC8992, and TC5995. Preferably, the tick polypeptide is selected from TC12142, TC9753, TC5995 and TC8992. In some embodiments, at least two, at least three or all four peptides TC12142, TC9753, TC5995 and TC8992 are used in the method.

Still further, the present invention provides a method for treating or preventing or reducing the severity of a tick infestation, comprising administering to the subject, a composition as described herein.

The invention also provides for a method for reducing the risk of transmission of a tick infestation in a population of animals, the method comprising administering to one or more subjects in the population, a composition as described herein.

In some embodiments of the methods broadly described above, the composition is administered to the subject intradermally, subcutaneously, intravenously, or other convenient method for providing the polypeptides to the subject for the purpose of stimulating an immune response.

In any method of the present invention, the compositions described herein may be administered as part of a "priming immunizations". The animal that receives the priming immunization may or may not have already been exposed to the tick polypeptide(s) against which the prime immunization is designed, for instance, by prior infestation. Still further, the compositions may be administered as part of one or more "booster immunizations". In various embodiments, the boost immunization is administered at a dose higher than, lower than, or equal to the effective dose that is normally administered when the boost immunization is administered alone without priming. In certain advantageous embodiments, the boost immunization is administered to an animal at a lower dose then the effective dose that would be used when the immunization is administered to the mammal alone without priming.

The methods of the invention are suitable for eliciting an immune response to a tick polypeptide in any subject that is prone to tick infestation (including mammals that are carriers of ticks). By way of an illustrative example, the methods of the present invention can be performed on an ungulate, for example any one of cattle, buffalo, deer, antelope, horses, sheep, donkeys, rhinoceroses, peccaries, pigs, giraffes, okapi, pronghorn, ox, antelopes, camels, llamas, chevrotains, hippopotamuses, tapirs and zebras. Suitably, the methods are performed on cattle, and more particularly beef cattle and/or dairy cattle. In other embodiments, the methods and compositions of the invention are useful for eliciting an immune response to a tick in a companion animal, including but not limited to dogs, cats, guinea pigs, mice, rats, and rabbits.

Any one of the compositions as described above and elsewhere here in can be used in the methods of the present invention.

In yet another aspect, the present invention provides a method of producing an antigen-binding molecule (e.g., an antibody, such as a neutralising antibody) that is immunointeractive with a tick polypeptide, wherein the method comprises immunizing an animal with one or more tick polypeptides as described herein, and optionally an adjuvant for potentiating an immune response in the animal to the one or more polypeptides; isolating an antigen-binding protein produced by the animal, wherein the antigen binding protein is capable of binding to one or more of the tick polypeptides with which the animal was immunized.

In some embodiments the antigen-binding molecule is a derivative antigen-binding molecule produced by the methods of this aspect. By way of an example, the derivative antigen-binding molecule is selected from antibody fragments (such as Fab, Fab', F(ab')$_2$, Fv), single chain (scFv) and domain antibodies, and fusion proteins comprising an antibody, and any other modified configuration of the immunoglobulin molecule that comprises an antigen binding and/or recognition site.

In some embodiments, the antigen-binding molecule (or derivative antigen-binding molecules) produced by these methods are formulated into a composition, wherein the compositions also comprise a pharmaceutically acceptable carrier, diluent, or adjuvant.

TABLE 1

Brief Description of the Sequences

Figure 1:
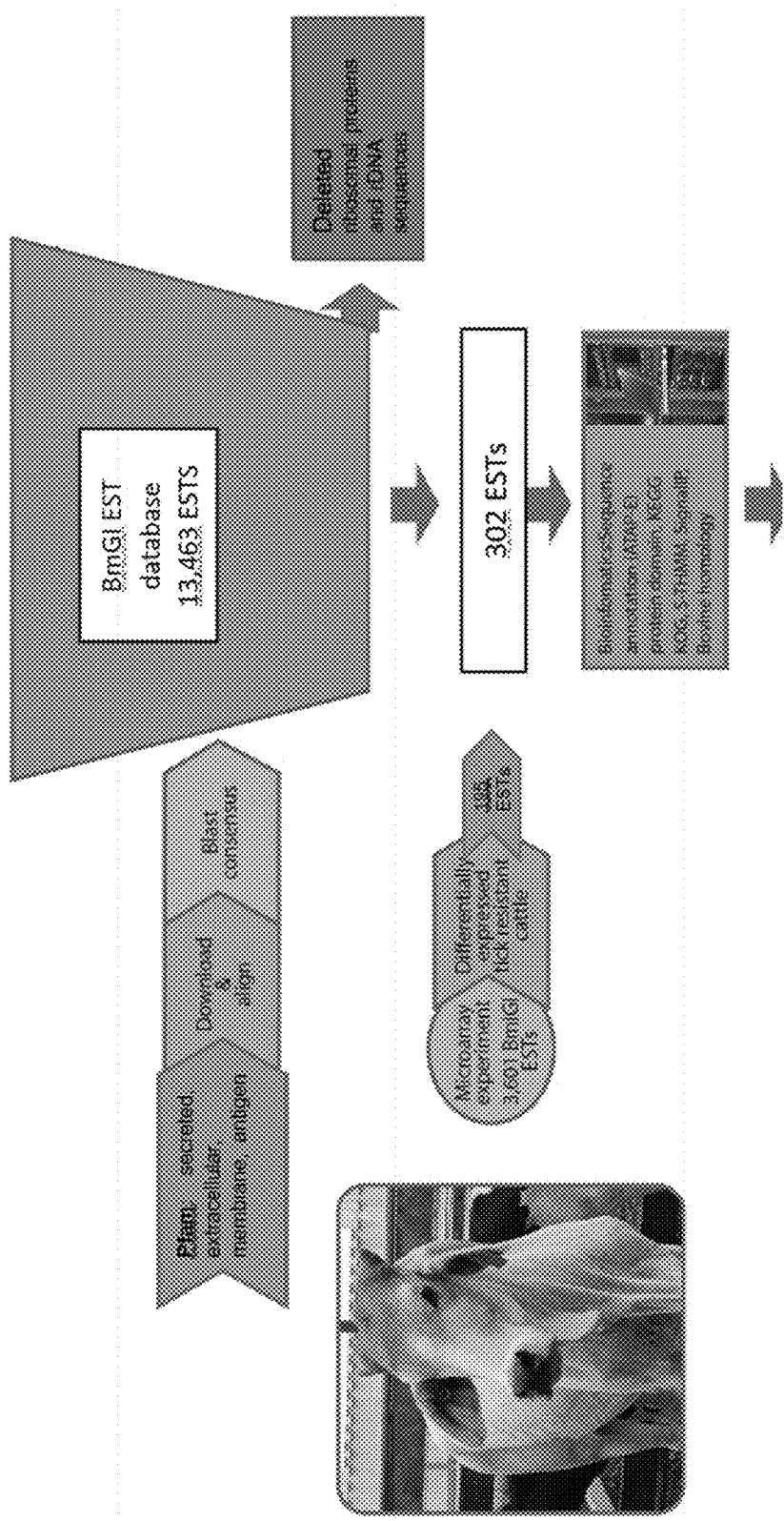
FIGS. 1 to 3: graphical flowcharts showing the peptide vaccine candidate discovery process.

| SEQ ID NUMBER | SEQUENCE description | LENGTH |
|---|---|---|
| SEQ ID NO: 1 | TC12130 full length polypeptide from R. microplus<br>MKPVSLFLLAVYLLVVQAEDLAGRTFGFGQSHPALQHAHHGHGMS<br>PQTQVHFNHVLPPHHGSDTGHAHGHSHHGHAASGNHHQVVHGH<br>QHNHQQSVQPGAATEPAASNVHTVPVLMCRVVKVPVSTPAPTVPP<br>RSDSSSSGTHGVGSHIAHSISHVFGTVVNPVVALLKNASVWLNRTT<br>HGDNGAAAHHHNHHHQSAVPHSLVLQKNSIRPASVTSAPTAPSPA<br>PTVASTVPSATTRSRLTMVPPFAPTVLPTVGAAAPTVRGPVPRVGT<br>FPVPATTVASADFPTSAPANVSSTLPVLIPVTDSSTSTLSTVVSSTLP<br>AAHVTTLAASTTTAPDSLNFRAIPFTPTATSSELPATTPVDATSTAAV<br>SVETTAEFLDPTVVTTQNPQPADVSTTHFPSTASIETPRRGVTLDP<br>RAGPFTLLVTSPKVPATGLPLQEQSNAATSPPSTLPVEPRALTTSTP<br>EATTSLPVSTDAPSLPLAGTILPPTVGTTFVRMSTVVSIDPVANRVP<br>PVTTTASGTLTPVPLSTAKLPVPLLSTTLGSTTSPLANFTFFGVRSV<br>RPKTR | 558 aa |
| SEQ ID NO: 2 | TC12130 full length polypeptide from R. australis<br>MKPVSLFLLAVCLLVVQAEYFAGRTFGFGHSHPALQHAHHGHGMS<br>SQAQGHINHVLPPHRGSHAGHAHGHSHHGQVPNAHQHQLVHVH<br>QHNHQQSAQPSAATAPAASNVSTVPVLMCRVVKVPVNTPAPTVPP<br>RSDSSSSGTHVGSHIAHSISHVFGTVVNPVMALLKNASVWLNRTAH<br>EDNGAAAHHHNHHHQSAVPHSLVLQKKVQVIGQRDNIPNGPASIST<br>RPASVTSAPTTPSPAPTVASTVPSAATRSRLTMVPPFAPTVLPTVV<br>PRHLL | 276 aa |

TABLE 1-continued

Brief Description of the Sequences

| SEQ ID NUMBER | SEQUENCE description | LENGTH |
|---|---|---|
| SEQ ID NO: 3 | MPAAN50tr full length polypeptide from *R. australis*<br>MELQATILLVFTLIVGSSAEFALQLGWHDPNVTEIRGRALGDPIPIILT<br>NYNNMQFYGIITIGTPPQSFKLLMDTGSSNFWVPSINCDQSMACRD<br>HAKYDSSKSSTFTKSGRYIRIRYSGGVVRGITSIDNVGVGPATVTQY<br>KFAEMDHSDGKLFRNAKYDGIFGLAFPSISQNNQLPLFDAMVKQGV<br>VRQAVFSLYLSKQPSEQNGGEIYFGGINAQRYTGAIHYVPVSQAAH<br>WQVVMDNINVQGTTLCVGGCPTVVDSGTSFLSGPSADVETLNRVI<br>GATKTPAGYFEVNCATIASLPPITFNLNGKSFPLQGEAYTIRIPLTTG<br>GEQCFTRISESDASGTNLWILGAVFTQTYYTVFDKVQNRVGFATAV | 373 aa |
| SEQ ID NO: 4 | MPAAN50tr full length polypeptide from *R. microplus*<br>MELQATILLVFTLIVGSSAEFALQLGWHDPNVTEIRGRALGDPIPIILT<br>NYNNMQFYGIITIGTPPQSFKLLMDTGSSNFWVPSINCDQSMACRD<br>HAKYDSSKSSTFTKSGRYIRIRYSGGVVRGITSIDNVGVGPATVTQY<br>KFAEMDHSDGKLFRNAKYDGIFGLAFPSISQNNQLPLFDAMVKQGV<br>VRQAVFSLYLSKQPSEQNGGEIYFGGINAQRYTGAIHYVPVSQAAH<br>WQVVMDNINVQGTTLCVGGCPTVVDSGTSFLSGPSADVETLNRVI<br>GATKTAAGYFEVNCATISSLPPITFNLNGKSFPLQGEPTRS | 320 aa |
| SEQ ID NO: 5 | MPAA730tr full length polypeptide from *R. microplus*<br>MSPLGITLLLGLLGVSTAQFSISLWRNKTDFEPRRRTWLDAAAVIPE<br>ELENEKNLHYYGLIGLGTPPQRFKVIFDTGSANLWVPSVKCPDTED<br>GCKDKKKYDSSKSSTYKADGRKFRIEYGSGIVEGIYSTDVLTIGNGK<br>VNPQTFAEATKAQGSIFKAAQFDGLLGLGYPALAEDNVVPVFDNM<br>MKQNLLPKPVFSVYLNRDPKATPGGEIYFGGINSNRYTGSITYTSVT<br>KKSYWQFKMQGMQVKKDKTFCVGGCDAVMDTGSSFIEGPRDEIE<br>RLNKYLRATEEPAGDWRVKCANIPKMPKISFTIGGREFTMTADQYII<br>QVQGSKKVKCYSGFAVSDTPTKKFWVIGQVFIGSFYTIFDRGSDRI<br>GFATVA | 375 aa |
| SEQ ID NO: 6 | MPAA730tr full length polypeptide from *R. australis*<br>MSPLGITLLLGLLGVSTAQFSISLWRNKTDFEPRRRTWLDAAAVIPE<br>ELENEKNLHYYGLIGLGTPPQSFKVIFDTGSANLWVPSVKCPDTED<br>GCKDKKKYDSSKSSTYKADGRKFRIEYGSGIVEGIYSTDVLTIGNGK<br>VNPQTFAEATKAQGSIFKAAKFDGLLGLGYPALAEDNVVPVFDNM<br>MKQNLLPKPVFSVYLNRDPKATPGGEIYFGGINSNRYTGSITYTSVT<br>KKSYWQFKMQGMQVKKDKTFCVGGCDAVMDTGSSFIEGPRDEIE<br>RLNKYLRATEE | 287 aa |
| SEQ ID NO: 7 | TC12142 full length polypeptide from *R. microplus*<br>MKFFATVTLLALVASAAFAEEEDAKKVEKKEDKKDVEGRGGFLGGG<br>PGFGVGVVPGVVGSPGVVGPGVVANPALVGAGVGHGVGHGVGH<br>GVGLGAVGVGHGVGPGVGLGGVGVGHGGGFQTGFGTSTGAQQA<br>GFQRGAAGHQQGSGAFTGGSAHRTVNAFSNNKGYDHKTGFSAS<br>DSKTFGAGQQQGSAGFQGGAAGHQAGFGQSSHGHTTGVGHAGV<br>GVVG | 221 aa |
| SEQ ID NO: 8 | TC12142 full length polypeptide from *R. australis*<br>MKFFATVTLLALVASATFAEEEGPKKAEKKEDKKDIEGRGGFLGGGP<br>GYGVGVVPGVVGSPGVVGPGVVANPALVGAGLGHGVGLGAVGV<br>GHGVGHGVSPGVGLGGVGVGQGGGFQTGFGTSTGAQQAGFQR<br>GAAGHQQGSGAFTGGSAHRTVNAFSNKQGYDHKTGFSASDSKTF<br>GAGQQQGSAGFQGGAAGHQAGFGQSSHGQTSGVGHAGVGVV | 216 aa |
| SEQ ID NO: 9 | TC10097 full length polypeptide from *R. microplus*<br>MLSQRTCVLLTALLVVCRINSALGSGLNSTVCNGLCLYSVDANLFC<br>EVAFVAPPCSTKRQLCCTEIRAIESLARVKEDTAVMDNNVWSARAN<br>NNQDSMRQDRSMYTDLLRLIVIQALRTAISSEYKAIKEKSMPATAIST<br>TTTAQYDPTWPEENDRFKTFKPAYAFKKTSSTPSAVLEPPQSFTVT<br>APSQDPPLLDASSSGSSTLAPLADSAPPTVSTSVSSDAETTMEKLL<br>YPCPGNCVPTFLTWFCDATNSDYECSSGRVCCMPITTTTPAEDVV<br>PECPGTCIPPAIFGLCKRPARLILKTTTCGRDLICCTETPMLL | 320 aa |
| SEQ ID NO: 10 | TC9753 full length polypeptide from *R. microplus*<br>MHCDYVLWNVVLFVVMVATSTAQKPCEGGGEKNCTGKEKWCLVD<br>ENGGVHEKCRDLDCSFSRFSCWFQCQGDTTLACHKSPTDDQCIC<br>SCVKNFCDRNEGQKCSGKTKWCFNETAGFTEWCGESGCDASKS<br>HWKVCKTPGTEMSCEKASDSDACHCTCVERVCSNQQGNRCTSN<br>KMKWCMISDKGHYTDTCNDRNCHPSTLPWKICYRRDYKPSCRKTT<br>LGTCLCTCVKG | 230 aa |
| SEQ ID NO: 11 | TC9753 full length polypeptide from *R. australis*<br>MHSDYVLWNVVLFVVMVATSTAQKPCEGGGEKNCTGKEKWCLVD<br>ENGGVHEKCRDLDCSSSRFSCWFQCEGDTTLACHKSPTDDICICS<br>CVKNFCDRNEGQKCSGKTKWCFNETAGFTEMCGESGCDASKSH | 230 aa |

TABLE 1-continued

| Brief Description of the Sequences | | |
|---|---|---|
| SEQ ID NUMBER | SEQUENCE description | LENGTH |
| | WKVCKTPGTEMSCEKASDSDACHCTCVERVCSNQQGNRCTSNK MKWCIISDKGRYTDSCNDRNCHPSTLPWKICYRRDYKPSCRKTTL GTCLCTCVKG | |
| SEQ ID NO: 12 | TC13011 full length polypeptide from *R. australis* MLRGALAAILLLISSDLMIHTAGLDIKQFVRRRERIWTYKTTRRDNVQ CEVDKLLYSTTLSITFKKCVFLRNRRCELQTTGVFDTDHTERMTTLH RGIFTRTETLLFLSRDRSCAVVKVYSLTNWNQSYYDMRVTNTFVRS ASLPACRTFFNRIIRPQTSHLVFFPRCLRLMRQRNEDEE | 180 aa |
| SEQ ID NO: 13 | TC13011 full length polypeptide from *R. microplus* MLRGALAAILLLISSDLMIHTAGLDIKQFVRRRERIWTYKTTRRDNVQ CEVDKLLYSTTLSITFKKCVFLRNRRCELQITGVFDTDIMERMTTIDR DIFTATETLLFLSRDHSCAVMKVESLTNWDQFYYDMRVPGSFERFA PPPDCRVFFDRIIGPQVAHRVFFPRCIRLMSQRNQE | 178 aa |
| SEQ ID NO: 14 | TC8992 full length polypeptide from *R. microplus* MAREIVLVCMIAAVARTALSAPKARVSRKNIQDRIQQLAKDFEAHLQ DASMPRHCAELLENGQHISGVYTIFHEAAGTSGQDVYCDMDTDDG GWTVIQRRGQYGHNAYYFYRNVVTEYANGFGNPADEYWIGNKALH ALTSGDEEMVLRIVLSNSTEDSTYFDYKTFTVASEQQLFQLRIGNFS EMTGDPMERLSGQKFTTYDRDNDASAFNCAERLRGAVVWYILCDD SNLNGLNLNGHHDSSGDGIVWEGTSSDAAHYSYPKVEMMIRPAK | 271 aa |
| SEQ ID NO: 15 | TC8992 full length polypeptide from *R. australis* MIAAVARTGLSAPKARVSRKNIQDRIQQLAKDFEAHLQDASMPRHC AELLDNGQHISGVYTIFHEAAGTSGQDVYCDMDTDDGGVVTVIQRR GQYGHNAYYFYRNWTEYANGFGNPADEYWIGNKALHALTSGDEE MVLRIVLSNSTEDSTYFDYKTFIVASEEELFQLRIGNFTGMSGDPME RLSGRQFSTYDLDNDASGYNCAERLRGAWWYFLCEDSNLNGLNL NGHHDSSGDGIVWEGTSSDAAHYSYPKVEMMIRPAN | 262 aa |
| SEQ ID NO: 16 | TC5995 full length polypeptide from *R. microplus* MVNSRVVVNGVAVVAVVVMVVVSVVVPVVQGKPKAGSGGPAAGA PDFSKFLGPPLPSEDCVGVVAAPGAAALVADPNDCTKYSVCSETF SSKFDCPPGQHFSPADNRCATPEEAKCDPAFADNDATDDEAINVD VKSVAVDVVDAADVEVDAANIVATDV | 160 aa |
| SEQ ID NO: 17 | TC5995 full length polypeptide from *R. australis* MVNSKVVVNGVAVVAVVVMVVVSVVVPVVQGKPKASSGGPAAGA PDFSKFLGPPLPSEDCVGVVAAPGAAALVADPNDCTKYSVCSETF SSKFDCPPGQHFSPADNRCATPEEAKCDPAFADNDATDDEAINVD VKSVAVDVVDAADVEGDAANIIATDV | 160 aa |
| SEQ ID NO: 18 | Keyhole Limpet Hemocyanin 1 polypeptide sequence | 3408 aa |
| SEQ ID NO: 19 | Bovine ubiquitin polypeptide (UniProtKB Acc. No. P63048) | 128 aa |
| SEQ ID NO: 20 | Bovine ubiquitin nucleic acid sequence | 228 nt |
| SEQ ID NO: 21 | Measles virus protein F peptide (residues 289-302) | 15 aa |
| SEQ ID NO: 22 | Native tetanus toxin (UniProtKB Acc. No. P04958) | 1315 aa |
| SEQ ID NO: 23 | Tetanus toxin peptide (residues 583-599) | 18 aa |
| SEQ ID NO: 24 | Tetanus toxin peptide (residues 830-844) | 15 aa |
| SEQ ID NO: 25 | Tetanus toxin peptide (residues 947-957) | 21 aa |
| SEQ ID NO: 26 | Anaplasma marginale polypeptide | 11 aa |
| SEQ ID NO: 27 | Plasmodium falciparum CSP protein | 20 aa |

TABLE 1-continued

Brief Description of the Sequences

| SEQ ID NUMBER | SEQUENCE description | LENGTH |
|---|---|---|
| SEQ ID NO: 28 | Influenza HA B epitope | 18 aa |
| SEQ ID NO: 29 | PADRE epitope sequence | 12 aa |
| SEQ ID NO: 30 | Concholepas concholepas hemocyanin subunit A (UniProtKB accession No. P84619) | 11 aa |
| SEQ ID NO: 31 | Concholepas concholepas hemocyanin subunit B (UniProtKB accession No. P84620) | 7 aa |
| SEQ ID NO: 32 | Chicken Ovalbumin (UniProtKB accession No. P01012) | 386 aa |
| SEQ ID NO: 33 | Bovine serum albumin (UniProtKB accession no. P02769) | 607 aa |
| SEQ ID NO: 34 | Cholera toxin B polypeptide (UniProt accession no. P01556) | 124 aa |
| SEQ ID NO: 35 | CMV CTL peptide epitope pp65$_{495-503}$ | 9 aa |
| SEQ ID NO: 36 | TC12130 peptide epitope from R. microplus PVSTPAPTVPPRSDSSSSGTHGV | 23 aa |
| SEQ ID NO: 37 | TC12130 peptide epitope from R. microplus TTHGDNGAAAH | 11 aa |
| SEQ ID NO: 38 | TC12130 peptide epitope from R. microplus IRPASVTSAPTAPSPAPTVASTVPSATTR | 29 aa |
| SEQ ID NO: 39 | TC12130 peptide epitope from R. microplus IRPASVTSAPTAPSPAPT | 18 aa |
| SEQ ID NO: 40 | TC12130 peptide epitope from R. microplus TAPSPAPTVASTVPSATTR | 19 aa |
| SEQ ID NO: 41 | TC12130 peptide epitope from R. microplus PFAPTVLPTVGAAAPTVRGPVPRVGTFPVPATTVASADFPTSAPANVS | 48 aa |
| SEQ ID NO: 42 | TC12130 peptide epitope from R. microplus PFAPTVLPTVGAAAPTVRGPV | 21 aa |
| SEQ ID NO: 43 | TC12130 peptide epitope from R. microplus PVPATTVASADFPTSAPANVS | 21 aa |
| SEQ ID NO: 44 | TC12130 peptide epitope from R. australis PVNTPAPTVPPRSDSSSSGTHVG | 23 aa |
| SEQ ID NO: 45 | TC12130 peptide epitope from R. australis TAHEDNGAAAH | 11 aa |
| SEQ ID NO: 46 | MPAAN50tr peptide epitope from R. australis FPLQGEAYTI | 10 aa |
| SEQ ID NO: 47 | MPAAN50tr peptide epitope from R. microplus FPLQGEPTRS | 10 aa |
| SEQ ID NO: 48 | MPAA730tr peptide epitope from R. australis SSFIEGPRDEIE | 12 aa |
| SEQ ID NO: 49 | MPAA730tr peptide epitope from R. microplus SSFIEGPRDEIE | 12 aa |
| SEQ ID NO: 50 | TC12142 peptide epitope from R. microplus FSNNKGYDHKTGFSASDSKTFGAGQQQGSAGFQGGAAGHQAGFGQSSHGHTTGVGHA | 57 aa |
| SEQ ID NO: 51 | TC12142 peptide epitope from R. microplus FSNNKGYDHKTGFSASDSKTF | 21 |

TABLE 1-continued

Brief Description of the Sequences

| SEQ ID NUMBER | SEQUENCE description | LENGTH |
|---|---|---|
| SEQ ID NO: 52 | TC12142 peptide epitope from R. microplus<br>HQQGSGAFTGGSAHR | 15 aa |
| SEQ ID NO: 53 | TC10097 peptide epitope from R. microplus<br>AFKKTSSTPSAVLEPPQSFTVTAPSQDPPLLDASSSGSSTLAPLAE<br>SAPPTVSTSVSNDAETTT | 64 aa |
| SEQ ID NO: 54 | TC10097 peptide epitope from R. microplus<br>WSARANNNQDSMRQD | 15 aa |
| SEQ ID NO: 55 | TC10097 peptide epitope from R. microplus<br>AFKKTSSTPSAVLEPPQSFTVTAPSQDPPLLDAS | 35 aa |
| SEQ ID NO: 56 | TC10097 peptide epitope from R. microplus<br>AFKKTSSTPSAVLEPPQSFTV | 21 aa |
| SEQ ID NO: 57 | TC10097 peptide epitope from R. microplus<br>DPPLLDASSSGSSTLAPLAES | 21 aa |
| SEQ ID NO: 58 | TC9753 peptide epitope from R. microplus<br>STAQKPCEGGGEKNCTGK | 18 aa |
| SEQ ID NO: 59 | TC9753 peptide epitope from R. microplus<br>DRNEGQKCSGK | 11 aa |
| SEQ ID NO: 60 | TC9753 peptide epitope from R. microplus<br>SNQQGNRCTS | 10 aa |
| SEQ ID NO: 61 | TC9753 peptide epitope from R. microplus<br>GHYTDTCNDRNCHPST | 16 aa |
| SEQ ID NO: 62 | TC9753 peptide epitope from R. australis<br>STAQKPCEGGGEKNCTGK | 18 aa |
| SEQ ID NO: 63 | TC9753 peptide epitope from R. australis<br>DRNEGQKCSGK | 11 aa |
| SEQ ID NO: 64 | TC9753 peptide epitope from R. australis<br>SNQQGNRCTS | 10 aa |
| SEQ ID NO: 65 | TC9753 peptide epitope from R. australis<br>GRYTDSCNDRNCHPST | 16 aa |
| SEQ ID NO: 66 | TC13011 polypeptide epitope from R. australis<br>MLRGALAAILLLISS | 15 aa |
| SEQ ID NO: 67 | TC13011 polypeptide epitope from R. australis<br>TFVRSASLPA | 10 aa |
| SEQ ID NO: 68 | TC13011 polypeptide epitope from R. microplus<br>MLRGALAAILLLISS | 15 aa |
| SEQ ID NO: 69 | TC13011 polypeptide epitope from R. microplus<br>SFERFAPPPD | 10 aa |
| SEQ ID NO: 70 | TC8992 polypeptide epitope from R. microplus<br>FTTYDRDNDASA | 12 aa |
| SEQ ID NO: 71 | TC8992 polypeptide epitope from R. australis<br>FSTYDLDNDASG | 12 aa |
| SEQ ID NO: 72 | TC5995 polypeptide epitope from R. microplus<br>SKFDCPPGQHFSPADNRCATPEEAKCDPAFADNDATDDEAIN | 42 aa |
| SEQ ID NO: 73 | TC5995 polypeptide epitope from R. microplus<br>ADNRCATPEEAKCDPAFADND | 21 aa |
| SEQ ID NO: 74 | TC5995 polypeptide epitope from R. microplus<br>DPAFADNDATDDEAIN | 16 aa |
| SEQ ID NO: 75 | TC5995 polypeptide fra epitope gment from R. australis<br>SKFDCPPGQHFSPADNRCATPEEAKCDPAFADNDATDDEAIN | 42 aa |
| SEQ ID NO: 76 | TC5995 polypeptide epitope from R. australis<br>ADNRCATPEEAKCDPAFADND | 21 aa |

TABLE 1-continued

Brief Description of the Sequences

| SEQ ID NUMBER | SEQUENCE description | LENGTH |
|---|---|---|
| SEQ ID NO: 77 | TC5995 polypeptide epitope from *R. australis* DPAFADNDATDDEAIN | 16 aa |
| SEQ ID NO: 78 | TC5943 polypeptide from *R. microplus* GALTPEPTNTNATALPVPTPLPLH | 24 aa |
| SEQ ID NO: 79 | TC5943 polypeptide epitope from *R. microplus* SPRRCKPLGKRGDPCSPRS | 19 aa |
| SEQ ID NO: 80 | TC5943 polypeptide epitope from *R. microplus* CGPNEGTCEDG | 11 aa |
| SEQ ID NO: 81 | TC5802 polypeptide from *R. microplus* VGHASGVGAPGLGVVGNPGLVGA | 23 aa |
| SEQ ID NO: 82 | TC5802 polypeptide epitope from *R. microplus* VGHASGVGAPGLGVVG | 16 aa |
| SEQ ID NO: 83 | TC5802 polypeptide epitope from *R. microplus* TSAGGHQSGYQGGAAGHNQGS | 21 aa |
| SEQ ID NO: 84 | TC5802 polypeptide epitope from *R. microplus* AAGHNQGSGAFAGGASGSTVN | 21 aa |
| SEQ ID NO: 85 | TC5802 polypeptide epitope from *R. microplus* GASGSTVNAFKNDAGYSHSSG | 21 aa |
| SEQ ID NO: 86 | TC6382 polypeptide epitope from *R. microplus* VSLGEPGYIG | 10 aa |
| SEQ ID NO: 87 | TC6382 polypeptide epitope from *R. microplus* FGGGYEDGYGAAHGAVAGGDQAGFQKGAAGHAQGSGRYAGGT | 42 aa |
| SEQ ID NO: 88 | TC6382 polypeptide epitope from *R. microplus* FGGGYEDGYGAAHGAVAGGDQ | 21 aa |
| SEQ ID NO: 89 | TC6382 polypeptide epitope from *R. microplus* GAVAGGDQAGFQKGAAGHAQG | 21 aa |
| SEQ ID NO: 90 | TC6382 polypeptide epitope from *R. microplus* GAAGHAQGSGRYAGGT | 16 aa |
| SEQ ID NO: 91 | TC6382 polypeptide epitope from *R. microplus* LFVVTVFTLLACSAT | 15 aa |
| SEQ ID NO: 92 | TC8946 polypeptide epitope from *R. microplus* LGGLGGAGLGGAGIV | 15 aa |
| SEQ ID NO: 93 | TC8946 polypeptide epitope from *R. microplus* PGLVGGGLGQGFGQGFQSG | 19 aa |
| SEQ ID NO: 94 | TC8946 polypeptide epitope from *R. microplus* FGSSAGGHQGGFQGGAGGHNLGATGFAGGAAGSKVNSYNDNRG YSHTSSFSSSDGKTFGTGNKQGSSGFQGGAGGHQAGFGQSGFG SAGGVSGGGLG | 97 aa |
| SEQ ID NO: 95 | TC8946 polypeptide epitope from *R. microplus* LGATGFAGGAAGSKVNSYNDN | 21 aa |
| SEQ ID NO: 96 | TC12850 polypeptide epitope from *R. microplus* LRVTDMFVRVRPLPA | 15 aa |
| SEQ ID NO: 97 | TC13324 T-cell epitope VVAVAAVSVVSSQEL | 15 aa |
| SEQ ID NO: 98 | TC5967 T cell epitope MISIVVFVGLASLAG | 15 aa |
| SEQ ID NO: 99 | Bm86 polypeptide sequence from *R. microplus* MAARSGSSAADRFVAVALLATALYATAAADNFDTYLATLSNVSALIK DEAMGVAFIEGLNDPYTTINNVDSSSSWDYASNITDYNQMSNKVS TEVSKMERQFGITAKRFDWHNFKNDSLKRLFRHVATIGLAALPDDK LENATSLSSKMAAIYGSTKVTVGKDKDLPLEPDLTRNMKEVGNYDK LLQTWLAWHNAVGPAIKQYYIPYIKLSNEAASLDGYDNIKSAWLSDY | 660 aa |

TABLE 1-continued

Brief Description of the Sequences

| SEQ ID NUMBER | SEQUENCE description | LENGTH |
|---|---|---|
| | ETENMTEIVDKLWEDLSPLYKKLHAYVRMKLREIYPGRLPEDGTIPA<br>HLLGNMWAQEWGTLYPHLTMEDKPLDISKTMVEQKWDAQKMFHA<br>AEDFFTSLGLDNMTSEFWSKSILTKPEDREIQCHASAWNMYNGDD<br>FRIKMCTDPSVEELRTVHHEMGHIEYYMQYKHLHVLLQEGANEGF<br>HEAVGDLIALSVATKTHYGKLSLLKPTDKYNAVDLLLMSALDKIAFLP<br>FGYLLDKWRWTIFTGETPFDKMNEKFWEYRIKYQGVSPPVKRNES<br>FFDGGAKYHVALHVPYLRYFVAFILQFQFHEHLCTVAKKVDEHHPF<br>HECDIYGEKNAGDVLKKGLSLGRSKPWPDVLEIMAGTRQMSASSL<br>KKYYEPLEKWLDERIKNEVVGWDKANVQDYMGVPSFANKVDFSAA<br>AVLASIGVILFCWKNISL | |
| SEQ ID NO: 100 | Bm86 fusion protein sequence SBm4912 R. microplus<br>CLSKHVLRKLQACEHSSICSDFGNEFCRNACDCGEWGAMNMTTRC | 45 aa |
| SEQ ID NO: 101 | Bm86 fusion protein sequence SBm7462 R. microplus<br>CLSKHVLRKLQACEHCDCGEWGAMNMTTRSSICSDFGNEFCRNAC | 45 aa |
| SEQ ID NO: 102 | Bm86 fusion protein sequence SBm19733 R. microplus<br>CLSKHVLRKLQACEHKEKSSICSDFGNEFCRNAKEKCDCGEWGA<br>MNMTTRC | 45 aa |
| SEQ ID NO: 103 | TC12173 T-cell epitope<br>PDMMDFVRSNGPMT | 14 aa |

DETAILED DESCRIPTION OF THE EMBODIMENTS

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

The terms "antigen" and "epitope" are well understood in the art and refer to the portion of a macromolecule which is specifically recognized by a component of the immune system, e.g., an antibody or a T-cell antigen receptor. Epitopes are recognized by antibodies in solution, e.g., free from other molecules. Epitopes are also recognized by T-cell antigen receptor that is present on the cell surface of a CD4+ T helper cell when the epitope is associated with a class II major histocompatibility complex (MHC) molecule.

By "antigen-binding molecule" is meant a molecule that has binding affinity for a tick polypeptide. It will be understood that this term extends to immunoglobulins, immunoglobulin fragments and non-immunoglobulin derived protein frameworks that exhibit antigen-binding activity.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

By "corresponds to" or "corresponding to" is meant an antigen which encodes an amino acid sequence that displays substantial sequence similarity or identity to an amino acid sequence in a target antigen. In general the antigen will display at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to at least a portion of the target antigen.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements (e.g., 1, 2, 3, 4, 5, 6, 7, 8, 9, 10, 11, 12, 13, 14, 15, 16, 17, 18, 19, 20, or more than 20 additional amino acid residues at the N-terminus or C-terminus of a polypeptide sequence) are optional and may or may not be present depending upon whether or not they affect the activity or action of the listed elements.

By "effective amount," in the context of modulating an immune response or treating or preventing a disease or condition, is meant the administration of that amount of composition to an individual in need thereof, either in a single dose or as part of a series, that is effective for achieving that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

It will be understood that "eliciting", "stimulating" or "inducing" an immune response as contemplated herein includes stimulating a new immune response and/or enhancing a previously existing immune response.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

The term "expression" with respect to a gene sequence refers to transcription of the gene and, as appropriate, translation of the resulting mRNA transcript to a protein. Thus, as will be clear from the context, expression of a coding sequence results from transcription and translation of the coding sequence. Conversely, expression of a non-coding sequence results from the transcription of the non-coding sequence.

By "expression vector" is meant any autonomous genetic element capable of directing the synthesis of a protein encoded by the vector. Such expression vectors are known by practitioners in the art.

"Immune response" or "immunological response" refers to the concerted action of any one or more of lymphocytes, antigen-presenting cells, phagocytic cells, granulocytes, and soluble macromolecules produced by the above cells or the liver (including antibodies, cytokines, and complement) that results in selective damage to, destruction of, or elimination from the body of invading pathogens, cells or tissues infected with pathogens. In some embodiments, an "immune response" encompasses the development in an individual of a humoral and/or a cellular immune response to a polypeptide that is encoded by an introduced synthetic coding sequence of the invention. A "humoral immune response" includes and encompasses an immune response mediated by antibody molecules, while a "cellular immune response" includes and encompasses an immune response mediated by T-lymphocytes and/or other white blood cells. Hence, an immunological response may include one or more of the following effects: the production of antibodies by B-cells; and/or memory/effector T-cells directed specifically to an antigen or antigens present in the composition or vaccine of interest. In some embodiments, these responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art (see, e.g., Montefiori et al., 1988, *J Clin Microbiol*. 26:231-235; Lew-Tabor et al., 2014, *Ticks Tick Bourne Dis*, 5(5): 500-10; and Rodriguez-Mallon, 2016, *Methods Mol Biol*, 1404: 243-59). The innate immune system of mammals also recognizes and responds to molecular features of pathogenic organisms and cancer cells via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature dendritic cells of, for example, the monocyte and plasmacytoid lineage (MDC, PDC), as well as gamma, delta, alpha and beta T-cells and B-cells and the like. Thus, the present invention also contemplates an immune response wherein the immune response involves both an innate and adaptive response.

Reference herein to "immuno-interactive" includes reference to any interaction, reaction, or other form of association between molecules and in particular where one of the molecules is, or mimics, a component of the immune system.

A composition is "immunogenic" if it is capable of either: a) generating an immune response (e.g., a $CD4^+$ immune response) against an a tick polypeptide in an individual; or b) reconstituting, boosting, or maintaining an immune response (e.g., a $CD4^+$ immune response) in an individual beyond what would occur if the agent or composition was not administered. An agent or composition is immunogenic if it is capable of attaining either of these criteria when administered in single or multiple doses. The immune response may include a cellular immune response and/or humoral immune response in a subject.

Throughout this specification, unless the context requires otherwise, the words "include," "includes" and "including" will be understood to imply the inclusion of a stated step or element or group of steps or elements but not the exclusion of any other step or element or group of steps or elements.

By "infestation" is meant to refer to a bite of one or more than one tick. An infestation can be the presence and attachment of a tick to a subject or, in certain embodiments, can refer to a subject coming in contact with a tick, but the tick does not remain attached. An infestation may or may not result in a condition or disorder that is directly or indirectly (e.g., through a hosting pathogenic organism) caused by a tick (e.g., bovine tick fever caused by *Babesia* and/or *Anaplasma*).

The term "gene" as used herein refers to any and all discrete coding regions of a genome, as well as associated non-coding and regulatory regions. The gene is also intended to mean an open reading frame encoding one or more specific polypeptides, and optionally comprising one or more introns, and adjacent 5' and 3' non-coding nucleotide sequences involved in the regulation of expression. In this regard, the gene may further comprise regulatory nucleic acids such as promoters, enhancers, termination and/or polyadenylation signals that are naturally associated with a given gene, or heterologous control signals. Genes may or may not be capable of being used to produce a functional protein. Genes can include both coding and non-coding regions.

By "linker" is meant a molecule or group of molecules (such as a monomer or polymer) that connects two molecules and often serves to place the two molecules in a desirable configuration.

As used herein, the term "mammal" refers to any mammal including, without limitation, cattle and other ungulates. The term also includes companion animals such as dogs, cats, guinea pigs, rabbits, mice and rats. The term does not denote a particular age. Thus, both adult and newborn individuals are intended to be covered.

The terms "operably connected," "operably linked" and the like as used herein refer to an arrangement of elements wherein the components so described are configured so as to perform their usual function. Thus, a given regulatory nucleic acid such as a promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence. Terms such as "operably connected," therefore, include placing a structural gene under the regulatory control of a promoter, which then controls the transcription and optionally translation of the gene.

By "pharmaceutically-acceptable carrier" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

"Polypeptide," "peptide" and "protein" are used interchangeably herein to refer to a polymer of amino acid residues and to variants and synthetic analogues of the same. As used herein, the terms "polypeptide," "peptide" and "protein" are not limited to a minimum length of the product. Thus, peptides, oligopeptides, dimers, multimers, and the like, are included within the definition. Both full-length proteins and portions thereof are encompassed by the definition. The terms "biologically active portions" or "fragments" are used interchangeably herein, to describe an immunogenic portion of a tick polypeptide. These portions can be a polypeptide which is, for example, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or more amino acid residues in length. Suitably, the portion or fragment has no less than about 1%, 10%, 25%, or 50% of an activity of the full-length polypeptide from which it is derived.

The terms "prime immunization", "priming immunization" and the like refer to primary antigen stimulation by using an immunostimulatory composition according to the present invention. The animal that receives the priming immunization may or may not have already been exposed to the tick polypeptide(s) against which the prime immunization is designed, for instance, by prior infestation.

The terms "boost immunization", "boosting immunization", "booster immunization" and the like refer to additional immunization administered to or effective in a mammal after the primary immunization. In various embodiments, the boost immunization is administered at a dose higher than, lower than, or equal to the effective dose that is normally administered when the boost immunization is administered alone without priming. In certain advantageous embodiments, the boost immunization is administered to an animal at a lower dose then the effective dose that would be used when the immunization is administered to the mammal alone without priming.

By "promiscuous T-cell epitope" is meant a highly immunogeic peptide that can be characterized in part by their capacity to bind several isotypic and allotypic forms of MHC class II molecules. By helping to bypass MHC restriction, they can induce T-cell and antibody responses in members of a genetically diverse population expressing diverse MHC haplotypes. The promiscuous T-cell epitopes can therefore be combined with antigens that, by themselves, are poorly immunogenic, to generate potent peptide immunogens. In some embodiments, the T-cell epitope comprises a heterologous CD4 T cell epitope to enhance the immunogenicity of the immunostimulatory compositions.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, 5 T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gin, Cys and Met) occurs in both sequences to yield the number of matched positions, dividing the number of matched positions by the total number of positions in the window of comparison (i.e., the window size), and multiplying the result by 100 to 10 yield the percentage of sequence identity. For the purposes of the present invention, "sequence identity" will be understood to mean the "match percentage" calculated by the DNASIS computer program (Version 2.5 for Windows; available from Hitachi Software engineering Co., Ltd., South San Francisco, Calif., USA) using standard defaults as used in the reference manual accompanying the software.

"Similarity" refers to the percentage number of amino acids that are identical or constitute conservative substitutions as defined in Table 6. Similarity may be determined using sequence comparison programs such as GAP (Deveraux et al. 1984, Nucleic Acids Research 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

By "subject" is meant any animal that is susceptible to infestation by a tick. A subject can include, but is not limited to vertebrates, including mammals such as livestock animals, including cattle, sheep, goats, pigs, horses chickens, turkeys, ostriches, ducks, and geese; companion animals (pets), such as cats, dogs, and horses; and animals that might be held in a zoo. "Ungulates" are members of a diverse group of primarily hoofed mammals that include odd-toed ungulates such as horses and rhinoceroses, and even-toes ungulates, such as cattle, pigs, giraffes, camels, deer, and hippopotamuses.

By "tick" is meant to refer to organisms belonging to the superfamily Ixodoidea. Ticks according to the invention can be at any developmental stage (e.g. larvae, nymphs, or adults).

By "treat," "treating," "treatment," and the like are meant to refer to reducing or ameliorating a disorder and/or symptoms associated therewith. It will be appreciated that, although not precluded, treating a disorder or condition does not require that the disorder, condition or symptoms associated therewith be completely eliminated.

The term "ubiquitin molecule" refers to a member of the protein superfamily of ubiquitin and ubiquitin-like proteins, which when conjugated to a target protein results in the introduction of that target protein into the cellular degradation machinery, including the proteasome.

The term "wild-type", with respect to an organism, polypeptide, or nucleic acid sequence, refers to an organism, polypeptide or nucleic acid sequence that is naturally occurring or available in at least one naturally occurring organism which is not changed, mutated, or otherwise manipulated by man.

2. Immunogenic Compositions

The present invention is based in part on the determination by the inventors that a number of polypeptides from *Rhipicephalus microplus* species complex are capable of stimulating or eliciting an immune response in an animal when administered to the animal (e.g., cattle and other livestock). Further, the present inventors have also determined that the immune response elicited by the polypeptides is surprisingly effective to prevent and treatment tick infestations, and in doing so, is also effective at reducing diseases that are transmitted by ticks. The present invention provides immunogenic compositions comprising at least one polypeptide antigen with an amino acid sequence that corresponds to tick polypeptides in compositions and methods for treating or preventing tick infestations in a subject.

In any embodiment of the invention, the composition comprises at least two immunogens, in the form of two different polypeptides, fragments or variants thereof, selected from the group consisting of: TC12130, MPAAN50tr, MPAA730tr, TC12142, TC10097, TC9753, TC13011, TC8992, and TC5995, wherein the first and second polypeptides are as shown in Table 2 below:

TABLE 2

| Immunogen 1 | Immunogen 2 |
| --- | --- |
| TC12130 | MPAAN50tr, TC12142, TC10097, TC9753, TC13011, TC8992, or TC5995 |
| MPAAN50tr | TC12142, TC10097, TC9753, TC13011, TC8992, or TC5995 |
| TC12142 | TC10097, TC9753, TC13011, TC8992, or TC5995 |
| TC10097 | TC9753, TC13011, TC8992, or TC5995 |
| TC9753 | TC12142, TC13011, TC8992, or TC5995 |
| TC13011 | TC8992, or TC5995 |
| TC8992 | TC5995, TC12142, or TC9753 |
| TC5995 | TC12142, TC9753, or TC8992 |

Preferably, the at least two immunogens are selected from TC12142, TC9753, TC5995 and TC8992. For example, the at least immunogens may be: TC12142 and TC9753; TC5995 and TC8992; TC12142 and TC5995; TC12142 and TC8992; TC9753 and TC5995; or TC9753 and TC8992.

In other embodiments, the composition comprises at least three polypeptide antigens as selected from Table 3:

TABLE 3

| Immunogen 1 | Immunogen | Immunogen 3 |
| --- | --- | --- |
| TC12130 | MPAAN50tr | TC12142 |
|  |  | TC10097 |
|  |  | TC9753 |
|  |  | TC13011 |
|  |  | TC8992 |
|  |  | TC5995 |
|  | TC12142 | TC10097 |
|  |  | TC9753 |
|  |  | TC13011 |
|  |  | TC8992 |
|  |  | TC5995 |
|  | TC10097 | TC9753 |
|  |  | TC13011 |
|  |  | TC8992 |
|  |  | TC5995 |
|  | TC9753 | TC13011 |
|  |  | TC8992 |
|  |  | TC5995 |
|  | TC13011 | TC8992 |
|  |  | TC5995 |
|  | TC8992 | TC5995 |
| MPAAN50tr | TC12142 | TC10097 |
|  |  | TC9753 |
|  |  | TC13011 |
|  |  | TC8992 |
|  |  | TC5995 |
|  | TC10097 | TC9753 |
|  |  | TC13011 |
|  |  | TC8992 |
|  |  | TC5995 |
|  | TC9753 | TC13011 |
|  |  | TC8992 |
|  |  | TC5995 |
|  | TC13011 | TC8992 |
|  |  | TC5995 |
|  | TC8992 | TC5995 |
| TC12142 | TC10097 | TC9753 |
|  |  | TC13011 |
|  |  | TC8992 |
|  |  | TC5995 |

TABLE 3-continued

| Immunogen 1 | Immunogen | Immunogen 3 |
|---|---|---|
|  | TC9753 | TC13011 |
|  |  | TC8992 |
|  |  | TC5995 |
| TC10097 | TC9753 | TC13011 |
|  |  | TC8992 |
|  |  | TC5995 |
|  | TC13011 | TC8992 |
|  |  | TC5995 |
|  | TC8992 | TC5995 |
| TC9753 | TC13011 | TC8992 |
|  |  | TC5995 |
|  | TC8992 | TC5995 |
| TC13011 | TC8992 | TC5995 |

Preferably, the at least three immunogens are selected from TC12142, TC9753, TC5995 and TC8992. For example, the at least three immunogens may be: TC12142, TC9753, and TC5995; TC12142, TC9753, and TC8992; TC9753, TC5995 and TC8992; or TC12142, TC5995 and TC8992

In still other embodiments, the composition comprises at least four polypeptide antigens that correspond to at least a portion of the tick polypeptides, as selected from Table 4:

TABLE 4

| Immunogen 1 | Immunogen 2 | Immunogen 3 | Immunogen 4 |
|---|---|---|---|
| TC12130 | MPAAN50tr | TC12142 | TC10097 |
|  |  |  | TC9753 |
|  |  |  | TC13011 |
|  |  |  | TC8992 |
|  |  |  | TC5995 |
|  |  | TC10097 | TC9753 |
|  |  |  | TC13011 |
|  |  |  | TC8992 |
|  |  |  | TC5995 |
|  |  | TC9753 | TC13011 |
|  |  |  | TC8992 |
|  |  |  | TC5995 |
|  |  | TC13011 | TC8992 |
|  |  |  | TC5995 |
|  |  | TC8992 | TC5995 |
|  | TC12142 | TC10097 | TC9753 |
|  |  |  | TC13011 |
|  |  |  | TC8992 |
|  |  |  | TC5995 |
|  |  | TC9753 | TC13011 |
|  |  |  | TC8992 |
|  |  |  | TC5995 |
|  |  | TC13011 | TC8992 |
|  |  |  | TC5995 |
|  |  | TC8992 | TC5995 |
| MPAAN50tr | TC12142 | TC10097 | TC9753 |
|  |  |  | TC13011 |
|  |  |  | TC8992 |
|  |  |  | TC5995 |
|  |  | TC9753 | TC13011 |
|  |  |  | TC8992 |
|  |  |  | TC5995 |
|  |  | TC10097 | TC9753 |
|  |  |  | TC13011 |
|  |  |  | TC8992 |
|  |  |  | TC5995 |
|  |  | TC13011 | TC8992 |
|  |  |  | TC5995 |
|  |  | TC8992 | TC5995 |
| TC12142 | TC10097 | TC9753 | TC13011 |
|  |  |  | TC8992 |
|  |  |  | TC5995 |
|  |  | TC13011 | TC8992 |
|  |  |  | TC5995 |
|  |  | TC8992 | TC5995 |
| TC10097 | TC9753 | TC13011 | TC8992 |
|  |  |  | TC5995 |
|  |  | TC8992 | TC5995 |
|  | TC13011 | TC8992 | TC5995 |
| TC9753 | TC13011 | TC8992 | TC5995 |

Preferably, the at least four immunogens are TC12142, TC9753, TC5995 and TC8992.

In yet other embodiments, the composition comprises at least five polypeptide antigens that correspond to at least a portion of the tick polypeptides, as selected from Table 5:

TABLE 5

| Immunogen 1 | Immunogen 2 | Immunogen 3 | Immunogen 4 | Immunogen 5 |
|---|---|---|---|---|
| TC12130 | MPAAN50tr | TC12142 | TC10097 | TC9753 |
|  |  |  |  | TC13011 |
|  |  |  |  | TC8992 |
|  |  |  |  | TC5995 |
|  |  |  | TC9753 | TC13011 |
|  |  |  |  | TC8992 |
|  |  |  |  | TC5995 |
|  |  |  | TC13011 | TC8992 |
|  |  |  |  | TC5995 |
|  |  |  | TC8992 | TC5995 |
|  |  | TC10097 | TC9753 | TC13011 |
|  |  |  |  | TC8992 |
|  |  |  |  | TC5995 |
|  |  |  | TC13011 | TC8992 |
|  |  |  |  | TC5995 |
|  |  |  | TC8992 | TC5995 |
|  |  | TC12142 | TC10097 | TC9753 |
|  |  |  |  | TC13011 |
|  |  |  |  | TC8992 |
|  |  |  |  | TC5995 |
|  |  |  | TC13011 | TC8992 |
|  |  |  |  | TC5995 |
|  |  |  | TC8992 | TC5995 |
|  | MPAAN50tr | TC12142 | TC10097 | TC9753 |
|  |  |  |  | TC13011 |
|  |  |  |  | TC8992 |
|  |  |  |  | TC5995 |
|  |  |  | TC13011 | TC8992 |
|  |  |  |  | TC5995 |
|  |  |  | TC8992 | TC5995 |
|  |  | TC9753 | TC13011 | TC8992 |
|  |  |  |  | TC5995 |
|  |  |  | TC8992 | TC5995 |
|  |  | TC10097 | TC9753 | TC13011 |
|  |  |  |  | TC8992 |
|  |  |  |  | TC5995 |
|  |  |  | TC13011 | TC8992 |
|  |  |  |  | TC5995 |
|  |  |  | TC8992 | TC5995 |
|  |  | TC13011 | TC8992 | TC5995 |

Preferably, at least four of the five immunogens include TC12142, TC9753, TC5995 and TC8992.

In still other embodiments, the composition comprises six polypeptide antigens, each polypeptide antigen corresponding to at least a portion of one of the tick polypeptides TC12130, MPAAN50tr, TC12142, TC10097, TC9753, and TC13011. Preferably, at least four of the six immunogens include TC12142, TC9753, TC5995 and TC8992.

Still further, the present invention provides for immunostimulatory compositions comprising, consisting or consisting essentially of at least seven polypeptide antigens, at least 8 polypeptide antigens, or all 9 of the polypeptide antigens TC12130, MPAAN50tr, MPAA730tr, TC12142, TC10097, TC9753, TC13011, TC8992, and TC5995.

2.1 Tick Polypeptides

The polypeptide antigens suitable for use in the compositions of the present invention correspond to at least one immunogenic epitope of a tick polypeptide. In some embodiments, the immunogenic epitope is present in one or more orthologous tick polypeptides (i.e., conserved in a tick species other than the species in which the tick polypeptide was identified or derived).

In some preferred embodiments, the tick polypeptides are obtained or derived from a tick of the Ixodidae family. Non-limiting examples of ticks belonging to the Ixodidae family include *Rhipicephalus (Boophilus) microplus, R. annulatus, R. australis, R. kohlsi, R. geigyi, R. appendiculatus, R. sanguineus* (brown dog tick), *R. bursa, Amblyomma variegatum* (tropical bont tick), *A. americanum* (lone star tick), *A. cajennense* (cayenne tick), *A. hebraeum* (African bont tick), *Boophilus decoloratus, Dermacentor reticulatus* (American levi tick), *D. andersoni* (Rocky Mountain wood tick), *D. marginazus* (ornate sheep tick), *D. variabilis* (American dog tick), *Haemaphysalis inermis, Ha. leachii, Ha. punctata, Hyalomma anatolicum anatolicum, Hy. dromedarii, Hy. marginatum marginatum, Ixodes ricinus* (castor bean tick), *I. persulcatus* (taiga tick), *I. scapularis* (commonly known as deer tick, blacklegged tick, and bear tick), and *I. hexagonus*. Notably, the "*R. microplus* species complex" has been designated into at least three clades, including *R. microplus* clade A, *R. microplus* clade B, *R. microplus* clade C and 2 other species *R. australis* and *R. annulatus*. (see, Burger et al, 2014; *Mol Phylogenet Evol* 78: 241-253; and Low et al., 2015 *Parasites & Vectors* 8:341).

In view of their substantial structural and sequence similarity, tick polypeptide orthologues are generally considered to have the same or similar levels of immunogenicity as one another. The present inventors thus consider that conserved tick polypeptides obtained from any tick species will be useful in eliciting an immune response in animals for treating or preventing a tick infestation.

In some embodiments, the at least one polypeptide antigen corresponds to at least a portion of a tick polypeptide derived from *R. microplus*. In some embodiments of this type, the at least one polypeptide antigen corresponds to at least a portion of the tick polypeptide TC12130. The tick polypeptide TC12130 is predicted to be a glycoprotein, and the full-length native amino acid sequence is as follows:

[SEQ ID NO: 1]
MKPVSLFLLAVYLLVVQAEDLAGRTFGFGQSHPALQHAHHGHGMSPQTQV

HFNHVLPPHHGSDTGHAHGHSHHGHAASGNHHQVVHGHQHNHQQSVQPGA

ATEPAASNVHTVPVLMCRVVKVPVSTPAPTVPPRSDSSSSGTHGVGSHIA

HSISHVFGTVVNPVVALLKNASVWLNRTTHGDNGAAAHHHNHHHQSAVPH

SLVLQKNSIRPASVTSAPTAPSPAPTVASTVPSATTRSRLTMVPPFAPTV

LPTVGAAAPTVRGPVPRVGTFPVPATTVASADFPTSAPANVSSTLPVLIP

VTDSSTSTLSTVVSSTLPAAHVTTLAASTTTAPDSLNFRAIPFTPTATSS

ELPATTPVDATSTAAVSVETTAEFLDPTVVTTQNPQPADVSTTHFPSTAS

IETPRRGVTLDPRAGPFTLLVTSPKVPATGLPLQEQSNAATSPPSTLPVE

PRALTTSTPEATTSLPVSTDAPSLPLAGTILPPTVGTTFVRMSTVVSIDP

VANRVPPVTTTASGTLTPVPLSTAKLPVPLLSTTLGSTTSPLANFTFFGV

RSVRPKTR.

For example, the tick polypeptide is a portion of the full-length native TC12130 amino acid sequence set forth in SEQ ID NO: 1. Suitable portions of this type may comprise, consist, or consist essentially of one or more of the amino acid sequences PVSTPAPTVPPRSDSSSSGTHGV (SEQ ID NO: 36) (corresponding to residues 123-145 of SEQ ID NO: 1), TTHGDNGAAAH (SEQ ID NO: 37) (corresponding to residues 178-188 of SEQ ID NO: 1), IRPASVT-SAPTAPSPAPTVASTVPSATTR (SEQ ID NO: 38) (corresponding to residues 209-237 of SEQ ID NO: 1) or an immunogenic fragment thereof (e.g., IRPASVT-SAPTAPSPAPT (SEQ ID NO: 39) or TAPSPAPTVASTVP-SATTR (SEQ ID NO: 40)), and PFAPTVLPTVGAAAPTVRGPVPRVGTFPVPATTVASA-DFPTSAPANVS (SEQ ID NO: 41) (corresponding to residues 245-292 of SEQ ID NO: 1) or an immunogenic fragment thereof (e.g., PFAPTVLPTVGAAAPTVRGPV (SEQ ID NO: 42) or PVPATTVASADFPTSAPANVS (SEQ ID NO: 43)). These tick polypeptide sequences are predicted to be B-cell epitopes, and are therefore particularly suitable for generating effective antibodies against the native TC12130 polypeptide.

In other illustrative embodiments, the polypeptide antigens may be derived from a functional orthologue of the native TC12130 tick polypeptide originally identified in *R. microplus*. By way of a non-limiting example, the tick polypeptide can be a functional orthologue of TC12130 as derived from any one *R. annulatus, R. australis*, etc. For example, in some embodiments the tick polypeptide corresponds to at least a portion of T12130 derived from *R. australis*, which has the full-length native amino acid sequence as follows:

[SEQ ID NO: 2]
MKPVSLFLLAVCLLVVQAEYFAGRTFGFGHSHPALQHAHHGHGMSSQAQG

HINHVLPPHRGSHAGHAHGHSHHGQVPNAHQHQLVHVHQHNHQQSAQPSA

ATAPAASNVSTVPVLMCRVVKVPVNTPAPTVPPRSDSSSSGTHVGSHIAH

SISHVFGTVVNPVMALLKNASVWLNRTAHEDNGAAAHHHNHHHQSAVPHS

LVLQKKVQVIGQRDNIPNGPASISTRPASVTSAPTTPSPAPTVASTVPSA

ATRSRLTMVPPFAPTVLPTVVPRHLL.

For example, the polypeptide antigen may comprise one or both of the amino acid sequences PVNTPAPTVP-PRSDSSSSGTHVG (SEQ ID NO: 44) (corresponding to residues 123-145 of SEQ ID NO: 2) and TAHEDNGAAAH (SEQ ID NO: 45) (corresponding to residues 177-187 of SEQ ID NO: 2).

In some embodiments, the polypeptide antigen corresponds to at least a portion of a TC12130-related tick polypeptide (i.e., clustered with TC12130), or a biologically active portion thereof. An illustrative example of a TC12130-related protein includes TC5943 (or a portion thereof with an amino acid sequence comprising GALT-PEPTNTNATALPVPTPLPLH (SEQ ID NO: 78), SPRRCKPLGKRGDPCSPRS (SEQ ID NO: 79), and/or CGPNEGTCEDG (SEQ ID NO: 80).

In some embodiments, the at least one polypeptide antigen corresponds to at least a portion of a tick polypeptide derived from *R. australis*. Thus, in some embodiments of this type the at least one tick polypeptide is the putative aspartic protease MPAAN50tr. The MPAAN50tr tick polypeptide has full-length native amino acid sequence as follows:

[SEQ ID NO: 3]
MELQATILLVFTLIVGSSAEFALQLGWHDPNVTEIRGRALGDPIPIILTN

YNNMQFYGIITIGTPPQSFKLLMDTGSSNFWVPSINCDQSMACRDHAKYD

SSKSSTFTKSGRYIRIRYSGGVVRGITSIDNVGVGPATVTQYKFAEMDHS

DGKLFRNAKYDGIFGLAFPSISQNNQLPLFDAMVKQGVVRQAVFSLYLSK

QPSEQNGGEIYFGGINAQRYTGAIHYVPVSQAAHWQVVMDNINVQGTTLC

VGGCPTVVDSGTSFLSGPSADVETLNRVIGATKTPAGYFEVNCATIASLP

PITFNLNGKSFPLQGEAYTIRIPLTTGGEQCFTRISESDASGTNLWILGA

VFTQTYYTVFDKVQNRVGFATAV.

For example, the tick polypeptide is a fragment of the native MPAAN50tr amino acid sequence set forth in SEQ ID NO: 3. For example, a suitable portion of this type may comprise the amino acid sequence FPLQGEAYTI (SEQ ID NO: 46) (i.e., amino acid residues 311-320 of SEQ ID NO: 3).

In other illustrative embodiments, the polypeptide antigen may be derived from a functional homologue of the native polypeptide identified in R. australis. By way of a non-limiting example, the tick polypeptide can be a functional orthologue of MPAAN50tr as derived from any one of R. microplus, R. annulatus, etc. For example, the tick polypeptide may comprise, consist, or consist essentially of at least a portion of a MPAAN50tr amino acid sequence derived from R. microplus, which has a native full-length amino acid sequence as follows:

[SEQ ID NO: 4]
MELQATILLVFTLIVGSSAEFALQLGWHDPNVTEIRGRALGDPIPIILTN

YNNMQFYGIITIGTPPQSFKLLMDTGSSNFWVPSINCDQSMACRDHAKYD

SSKSSTFTKSGRYIRIRYSGGVVRGITSIDNVGVGPATVTQYKFAEMDHS

DGKLFRNAKYDGIFGLAFPSISQNNQLPLFDAMVKQGVVRQAVFSLYLSK

QPSEQNGGEIYFGGINAQRYTGAIHYVPVSQAAHWQVVMDNINVQGTTLC

VGGCPTVVDSGTSFLSGPSADVETLNRVIGATKTAAGYFEVNCATISSLP

PITFNLNGKSFPLQGEPTRS.

By way of an illustration, a portion of MPAAN50tr may comprise, consist, or consist essentially of the amino acid sequence FPLQGEPTRS (SEQ ID NO: 47) (corresponding to residues 311-320 of SEQ ID NO 4).

In some embodiments, the at least one polypeptide antigen corresponds to at least a portion of the R. microplus tick polypeptide MPAA730tr. The MPAA730tr tick polypeptide is a putative aspartic protease, and has a full-length native amino acid sequence as follows:

[SEQ ID NO: 5]
MSPLGITLLLGLLGVSTAQFSISLWRNKTDFEPRRRTWLDAAAVIPEELE

NEKNLHYYGLIGLGTPPQRFKVIFDTGSANLWVPSVKCPDTEDGCKDKKK

YDSSKSSTYKADGRKFRIEYGSGIVEGIYSTDVLTIGNGKVNPQTFAEAT

KAQGSIFKAAQFDGLLGLGYPALAEDNVVPVFDNMMKQNLLPKPVFSVYL

NRDPKATPGGEIYFGGINSNRYTGSITYTSVTKKSYWQFKMQGMQVKKDK

TFCVGGCDAVMDTGSSFIEGPRDEIERLNKYLRATEEPAGDWRVKCANIP

KMPKISFTIGGREFTMTADQYIIQVQGSKKVKCYSGFAVSDTPTKKFWVI

GQVFIGSFYTIFDRGSDRIGFATVA.

By way of an illustration, the polypeptide antigen may correspond to the full length native MPAA730tr amino acid sequence as set forth in SEQ ID NO: 5, or correspond to a portion of the native MPAA730tr amino acid sequence set forth in SEQ ID NO: 5. For example, a suitable portion of this type may comprise the amino acid sequence SSFIEGPRDEIE (SEQ ID NO: 48) (i.e., amino acid residues 265-276 of SEQ ID NO: 5).

In other illustrative embodiments, the polypeptide antigen may be derived from a functional homologue of the native polypeptide identified in R. australis. By way of a non-limiting example, the tick polypeptide can be a functional orthologue of MPAA730tr as derived from any member of the R. microplus species complex including other R. microplus clades and R. annulatus, for example. For example, the tick polypeptide may comprise a MPAA730tr amino acid sequence derived from R. microplus, which has a native full-length amino acid sequence as follows:

[SEQ ID NO: 6]
MSPLGITLLLGLLGVSTAQFSISLWRNKTDFEPRRRTWLDAAAVIPEELE

NEKNLHYYGLIGLGTPPQSFKVIFDTGSANLWVPSVKCPDTEDGCKDKKK

YDSSKSSTYKADGRKFRIEYGSGIVEGIYSTDVLTIGNGKVNPQTFAEAT

KAQGSIFKAAKFDGLLGLGYPALAEDNVVPVFDNMMKQNLLPKPVFSVYL

NRDPKATPGGEIYFGGINSNRYTGSITYTSVTKKSYWQFKMQGMQVKKDK

TFCVGGCDAVMDTGSSFIEGPRDEIERLNKYLRATEE.

By way of an illustration, a suitable portion may comprise, consist, or consist essentially of the amino acid sequence SSFIEGPRDEIE (SEQ ID NO: 49) (corresponding to residues 265-276 of SEQ ID NO 6).

In some embodiments, the at least one polypeptide antigen corresponds to at least a portion of the R. microplus tick polypeptide TC12142. The TC12142 full-length native amino acid sequence is as follows:

[SEQ ID NO: 7]
MKFFATVTLLALVASAAFAEEDAKKVEKKEDKKDVEGRGGFLGGGPGFGV

GVVPGVVGSPGVVGPGVVANPALVGAGVGHGVGHGVGHGVGLGAVGVGHG

VGPGVGLGGVGVGHGGGFQTGFGTSTGAQQAGFQRGAAGHQQGSGAFTGG

SAHRTVNAFSNNKGYDHKTGFSASDSKTFGAGQQQGSAGFQGGAAGHQAG

FGQSSHGHTTGVGHAGVGVVG.

For example, the polypeptide antigen may be a portion of the native TC12142 tick polypeptide amino acid sequence from R. microplus as set forth in SEQ ID NO: 7. For example, suitable portions of this type may comprise, consist, or consist essentially of one or both of the amino acid sequences: FSNNKGYDHKTGFSASD-SKTFGAGQQQGSAGFQG-GAAGHQAGFGQSSHGHTTGVG HA (SEQ ID NO: 50) (corresponding to residues 159-215 of SEQ ID NO: 7) or an antigenic fragment thereof (for example, FSNNKGYDHKTGFSASDSKTF (SEQ ID NO: 51) (corresponding to residues 159-179 of SEQ ID NO: 7)), and HQQGSGAFTGGSAHR (SEQ ID NO: 52) (corresponding to residues 140-154 of SEQ ID NO: 7).

In other illustrative embodiments, the polypeptide antigen may be derived from a tick polypeptide that is a functional orthologue of the native TC12142 tick polypeptide originally identified in *R. microplus*. By way of a non-limiting example, the tick polypeptide can be a functional orthologue of TC12142 as derived from any one of *R. annulatus, R. australis*, etc. For example, in some embodiments the tick polypeptide corresponds to TC12142 derived from *R. australis*, which has the full-length native amino acid sequence as follows:

[SEQ ID NO: 8]
MKFFATVTLLALVASATFAEEGPKKAEKKEDKKDIEGRGGFLGGGPGYGV

GVVPGVVGSPGVVGPGVVANPALVGAGLGHGVGLGAVGVGHGVGHGVSPG

VGLGGVGVGQGGGFQTGFGTSTGAQQAGFQRGAAGHQQGSGAFTGGSAHR

TVNAFSNKQGYDHKTGFSASDSKTFGAGQQQGSAGFQGGAAGHQAGFGQS

SHGQTSGVGHAGVGVV.

In some embodiments, the polypeptide antigen corresponds to at least a portion of a TC12142-related tick polypeptide (i.e., clustered with TC12142), or a biologically active fragment thereof. An illustrative example of a TC12142-related protein includes:

TC5802 e.g., at least one B-cell epitope selected from:

(SEQ ID NO: 81)
VGHASGVGAPGLGVVGNPGLVGA,, (SEQ ID NO: 82)
VGHASGVGAPGLGVVG,, (SEQ ID NO: 83)
TSAGGHQSGYQGGAAGHNQGS,, (SEQ ID NO: 84)
AAGHNQGSGAFAGGASGSTVN,,
and (SEQ ID NO: 85)
GASGSTVNAFKNDAGYSHSSG),, TC6382, e.g., at least one B-cell epitope selected from:

(SEQ ID NO: 86)
VSLGEPGYIG,, (SEQ ID NO: 87)
FGGGYEDGYGAAHGAVAGGDQAGFQKGAAGHAQGSGRYAGGT,, (SEQ ID NO: 88)
FGGGYEDGYGAAHGAVAGGDQ,, (SEQ ID NO: 89)
GAVAGGDQAGFQKGAAGHAQG,,
and (SEQ ID NO: 90)
GAAGHAQGSGRYAGGT,,
and/or the T-cell epitope (SEQ ID NO: 91)
LFVVTVFTLLACSAT,
and TC8946 (e.g., at least one B-cell epitope selected from:

(SEQ ID NO: 92)
LGGLGGAGLGGAGIV,, (SEQ ID NO: 93)
PGLVGGGLGQGFGQGFQSG, (SEQ ID NO: 94)
FGSSAGGHQGGFQGGAGGHNLGATGFAGGAAGSKVNSYNDNRGYSHTSS

FSSSDGKTFGTGNKQGSSGFQGGAGGHQAGFGQSGFGSAGGVSGG

GLG,,
and (SEQ ID NO: 95)
LGATGFAGGAAGSKVNSYNDN.

In some embodiments, the at least one polypeptide antigen corresponds to at least a portion of the *R. microplus* tick polypeptide TC10097. The full-length native TC10097 tick polypeptide sequence is as follows:

[SEQ ID NO: 9]
MLSQRTCVLLTALLVVCRINSALGSGLNSTVCNGLCLYSVDANLFCEVAF

VAPPCSTKRQLCCTEIRAIESLARVKEDTAVMDNNVWSARANNNQDSMRQ

DRSMYTDLLRLIVIQALRTAISSEYKAIKEKSMPATAISTTTTAQYDPTW

PEENDRFKTFKPAYAFKKTSSTPSAVLEPPQSFTVTAPSQDPPLLDASSS

GSSTLAPLADSAPPTVSTSVSSDAETTMEKLLYPCPGNCVPTFLTWFCDA

TNSDYECSSGRVCCMPITTTTPAEDVVPECPGTCIPPAIFGLCKRPARLI

LKTTTCGRDLICCTETPMLL.

For example, the tick polypeptide may be the full length TC10097 polypeptide sequence as set forth in SEQ ID NO: 9, or a portion of the native TC10097 amino acid sequence set forth in SEQ ID NO: 9. For example, suitable fragments of this type may comprise, consist, or consist essentially of one or both of the amino acid sequences AFKKTSSTPSAVLEPPQSFTVTAPSQDPPLLDASSSGSSTLAPLAES-APPTVSTSVSND AETTT (SEQ ID NO: 53) (corresponding to residues 165-228 of SEQ ID NO: 9) and the amino acid sequences selected from WSARANNNQDSMRQD (SEQ ID NO: 54) (corresponding to residues 86-101 of SEQ ID NO: 9). Alternatively or in addition, the polypeptide antigen comprise, consist, or consist essentially of an antigenic fragment of the full-length predicted B-cell epitope, for example, AFKKTSSTPSAVLEPPQSFTVTAPSQDP-PLLDAS (SEQ ID NO: 55) (corresponding to residues 165-198 of SEQ ID NO: 9), AFKKTSSTP-SAVLEPPQSFTV (SEQ ID NO: 56) (corresponding to residues 165-185 of SEQ ID NO: 9), and DPPLLDAS-SSGSSTLAPLAES (SEQ ID NO: 57) (corresponding to residues 191-203 of SEQ ID NO: 9). In other illustrative examples, the polypeptide antigen may be derived from a functional orthologue of the native tick polypeptide identified above from *R. microplus*. By way of a non-limiting example, the tick polypeptide can be a functional orthologue of TC10097 as derived from any one of *R. annulatus, R. australis*, etc.

In some embodiments, the at least one polypeptide antigen corresponds to at least a portion of the *R. microplus* tick polypeptide TC9753. The full-length native TC9753 tick polypeptide sequence from *R. microplus* is as follows:

[SEQ ID NO: 10]
MHCDYVLWNVVLFVVMVATSTAQKPCEGGGEKNCTGKEKWCLVDENGGVH

EKCRDLDCSFSRFSCWFQCQGDTTLACHKSPTDDQCICSCVKNFCDRNEG

QKCSGKTKWCFNETAGFTEWCGESGCDASKSHWKVCKTPGTEMSCEKASD

SDACHCTCVERVCSNQQGNRCTSNKMKWCMISDKGHYTDTCNDRNCHPST

LPWKICYRRDYKPSCRKTTLGTCLCTCVKG.

By way of an example, the tick polypeptide is a portion of the native TC9753 amino acid sequence as set forth in SEQ ID NO: 10. Such fragments may comprise, consist, or consist essentially of the amino acid sequences selected from STAQKPCEGGGEKNCTGK (SEQ ID NO: 58) (i.e., amino acid residues 20-37 of SEQ ID NO: 10), DRNEGQKCSGK (SEQ ID NO: 59) (corresponding to residues 96-106 of SEQ ID NO:10), SNQQGNRCTS (SEQ ID NO: 60) (corresponding to residues 164-173 of SEQ ID NO: 10), and GHYTDTCNDRNCHPST (SEQ ID NO: 61) (corresponding to residues 185-200 of SEQ ID NO: 10).

In other illustrative embodiments, the polypeptide antigen may be derived from a functional orthologue of the native TC9753 tick polypeptide originally identified in *R. microplus*. By way of a non-limiting example, the tick polypeptide can be a functional orthologue of TC9753 as derived from any one of *R. annulatus, R. australis*, etc. For example, the tick polypeptide corresponds to at least a portion of TC9753 derived from *R. australis*, which has the full-length native amino acid sequence as follows:

[SEQ ID NO: 11]
MHSDYVLWNVVLFVVMVATSTAQKPCEGGGEKNCTGKEKWCLVDENGGVH

EKCRDLDCSSSRFSCWFQCEGDTTLACHKSPTDDICICSCVKNFCDRNEG

QKCSGKTKWCFNETAGFTEMCGESGCDASKSHWKVCKTPGTEMSCEKASD

SDACHCTCVERVCSNQQGNRCTSNKMKWCIISDKGRYTDSCNDRNCHPST

LPWKICYRRDYKPSCRKTTLGTCLCTCVKG.

By way of an example, suitable portions of TC9753 may comprise, consist, or consist essentially of the amino acid sequences selected from STAQKPCEGGGEKNCTGK (SEQ ID NO: 62) (i.e., amino acid residues 20-37 of SEQ ID NO: 11), DRNEGQKCSGK (SEQ ID NO: 63) (corresponding to residues 96-106 of SEQ ID NO: 11), SNQQGNRCTS (SEQ ID NO: 64) (corresponding to residues 164-173 of SEQ ID NO: 11), and GRYTDSCNDRNCHPST (SEQ ID NO: 65) (corresponding to residues 185-200 of SEQ ID NO: 11).

In some embodiments, the at least one polypeptide antigen corresponds to at least a portion of the *R. australis* tick polypeptide TC13011. By way of an example, in one embodiment the full-length native TC13011 tick polypeptide is derived from *R. australis* and comprises the amino acid sequence set forth below:

[SEQ ID NO: 12]
MLRGALAAILLLISSDLMIHTAGLDIKQFVRRRERIWTYKTTRRDNVQCE

VDKLLYSTTLSITFKKCVFLRNRRCELQTTGVFDTDHTERMTTLHRGIFT

RTETLLFLSRDRSCAVVKVYSLTNWNQSYYDMRVTNTFVRSASLPACRTF

FNRIIRPQTSHLVFFPRCLRLMRQRNEDEE.

An alternative example, the tick polypeptide may be a portion of the native TC13011 amino acid sequence as set forth in SEQ ID NO: 12. For example, suitable portions of this type may comprise, consist, or consist essentially of one or both of the B-cell epitope amino acid sequence MLRGALAAILLLISS (SEQ ID NO: 66) (i.e., amino acid residues 1-15 of SEQ ID NO: 12) and the T-cell epitope amino acid sequence TFVRSASLPA (SEQ ID NO: 67) (i.e., amino acid residues 137-146 of SEQ ID NO: 12).

In other illustrative embodiments, the polypeptide antigen may be derived from a functional orthologue of the native tick polypeptide identified in *R. australis*. For example, the tick polypeptide can be a functional orthologue of *R. australis* TC13011 as derived from any one of *R. microplus, R. annulatus*, etc. For example, in some embodiments the tick polypeptide corresponds to at least a portion of TC13011 derived from *R. microplus*, which has the full-length native amino acid sequence as follows:

[SEQ ID NO: 13]
MLRGALAAILLLISSDLMIHTAGLDIKQFVRRRERIWTYKTTRRDNVQCE

VDKLLYSTTLSITFKKCVFLRNRRCELQITGVFDTDIMERMTTIDRDIFT

ATETLLFLSRDHSCAVMKVESLTNWDQFYYDMRVPGSFERFAPPPDCRVF

FDRIIGPQVAHRVFFPRCIRLMSQRNQE.

By way of an illustration, the tick polypeptide may be derived from *R. microplus* and comprise, consist, or consist essentially of one or both of the B-cell epitope amino acid sequence MLRGALAAILLLISS (SEQ ID NO: 68) (i.e., amino acid residues 1-15 of SEQ ID NO: 13) and the T-cell epitope amino acid sequence SFERFAPPPD (SEQ ID NO: 69) (i.e., amino acid residues 137-146 of SEQ ID NO: 13).

In some embodiments, the polypeptide antigen corresponds to at least a portion of a TC13011-related tick polypeptide (i.e., clustered with TC13011. An illustrative example of a TC13011-related protein is TC12850 (e.g., the T-cell epitope LRVTDMFVRVRPLPA (SEQ ID NO: 96)).

In some embodiments, the at least one polypeptide antigen corresponds to at least a portion of the *R. microplus* tick polypeptide TC8992 (which is an ixoderin). By way of an example, in some embodiments the polypeptide antigen comprises, consists or consists essentially of the full-length native TC8992 tick polypeptide with the amino acid sequence set forth below:

[SEQ ID NO: 14]
MAREIVLVCMIAAVARTALSAPKARVSRKNIQDRIQQLAKDFEAHLQDAS

MPRHCAELLENGQHISGVYTIFHEAAGTSGQDVYCDMDTDDGGWTVIQRR

GQYGHNAYYFYRNWTEYANGFGNPADEYWIGNKALHALTSGDEEMVLRIV

LSNSTEDSTYFDYKTFTVASEQQLFQLRIGNFSEMTGDPMERLSGQKFTT

YDRDNDASAFNCAERLRGAWWYILCDDSNLNGLNLNGHHDSSGDGIVWEG

TSSDAAHYSYPKVEMMIRPAK.

By way of an alternative example, the tick polypeptide is a portion of the native TC8992 amino acid sequence as set forth in SEQ ID NO: 14. Suitable fragments of this type may comprise, consist, or consist essentially of the amino acid sequence FTTYDRDNDASA (SEQ ID NO: 70) (i.e., amino acid residues 198-209 of SEQ ID NO: 14).

In other illustrative embodiments, the polypeptide antigen may be derived from a functional orthologue of the native TC8992 tick polypeptide originally identified in *R. microplus*. By way of a non-limiting example, the tick polypeptide may be a functional orthologue of TC8992 as derived from *R. australis, R. annulatus*, etc. For example, in some embodiments the tick polypeptide corresponds to TC8992 derived from *R. australis*, which has the full-length native amino acid sequence as follows:

[SEQ ID NO: 15]
MIAAVARTGLSAPKARVSRKNIQDRIQQLAKDFEAHLQDASMPRHCAELL

DNGQHISGVYTIFHEAAGTSGQDVYCDMDTDDGGWTVIQRRGQYGHNAYY

FYRNWTEYANGFGNPADEYWIGNKALHALTSGDEEMVLRIVLSNSTEDST

YFDYKTFIVASEEELFQLRIGNFTGMSGDPMERLSGRQFSTYDLDNDASG

YNCAERLRGAWWYFLCEDSNLNGLNLNGHHDSSGDGIVWEGTSSDAAHYS

YPKVEMMIRPAN.

By way of an example, suitable portions of this sequence may comprise, consist, or consist essentially of the amino acid sequence FSTYDLDNDASG (SEQ ID NO: 71) (i.e., amino acid residues 189-200 of SEQ ID NO: 15).

In some embodiments, the at least one polypeptide antigen corresponds to at least a portion of the *R. microplus* tick polypeptide TC5995. The full-length native TC5995 tick polypeptide, which is a mucin, has the amino acid sequence set forth below:

[SEQ ID NO: 16]
MVNSRVVVNGVAVVAVVVMVVVSVVVPVVQGKPKAGSGGPAAGAPDFSKF

LGPPLPSEDCVGVVAAPGAAALVADPNDCTKYSVCSETFSSKFDCPPGQH

FSPADNRCATPEEAKCDPAFADNDATDDEAINVDVKSVAVDVVDAADVEV

DAANIVATDV.

For example, the tick polypeptide may be a portion of the native TC5995 amino acid sequence as set forth in SEQ ID NO: 9. Suitable portions of this type may comprise, consist, or consist essentially of the amino acid sequence SKFDCPPGQHFSPADNRCATPEEAKCDPAFADN-DATDDEAIN (SEQ ID NO: 72) (i.e., amino acid residues 91-132 of SEQ ID NO: 16) or an antigenic fragment thereof (for example, one or both of amino acid sequences ADNR-CATPEEAKCDPAFADND (SEQ ID NO: 73) (i.e., amino acid residues 104-124 of SEQ ID NO: 16) and DPAFADN-DATDDEAIN (SEQ ID NO: 74) (i.e., amino acid residues 117-132 of SEQ ID NO: 16)).

In other embodiments, the polypeptide antigen may be derived from a functional orthologue of the native TC5995 tick polypeptide originally identified in *R. microplus*. By way of a non-limiting example, the tick polypeptide can be a functional orthologue of TC5995 as derived from *R. australis, R. annulatus*, etc. For example, in some embodiments the tick polypeptide corresponds to at least a portion of TC5995 derived from *R. australis*, which has the full-length native amino acid sequence as follows:

[SEQ ID NO: 17]
MVNSKVVVNGVAVVAVVVMVVVSVVVPVVQGKPKASSGGPAAGAPDFSKF

LGPPLPSEDCVGVVAAPGAAALVADPNDCTKYSVCSETFSSKFDCPPGQH

-continued
FSPADNRCATPEEAKCDPAFADNDATDDEAINVDVKSVAVDVVDAADVEG

DAANIIATDV.

By way of an example, suitable portions of this type may comprise, consist, or consist essentially of the amino acid sequence SKFDCPPGQHFSPADNRCATPEE AKCDPA-FADNDATDDEAIN (SEQ ID NO: 75) (i.e., amino acid residues 91-132 of SEQ ID NO: 17) or an antigenic fragment thereof (for example, one or both of amino acid sequences ADNRCATPEEAKCDPAFADND (SEQ ID NO: 76) (i.e., amino acid residues 104-124 of SEQ ID NO: 17) and DPAFADNDATDDEAIN (SEQ ID NO: 77) (i.e., amino acid residues 117-132 of SEQ ID NO: 17).

In some embodiments, the polypeptide antigen corresponds to a TC5995-related tick polypeptide (i.e., clustered with TC5995), or a biologically active portion thereof. Illustrative examples of TC5995-related proteins include TC13324 (e.g., the T-cell epitope WAVAAVSVVSSQEL (SEQ ID NO: 97)), and TC5967 (e.g., the T-cell epitope MISIVVFVGLASLAG (SEQ ID NO: 98)).

In further embodiments, the polypeptide antigen may further comprise a T-cell epitope derived from the protein sequence of TC12173. For example, in a preferred, embodiment, the T-cell epitope comprises, consists of or consists essentially of the sequence PDMMDFVRSNGPMTI (SEQ ID NO: 103). Furthermore, the tick polypeptides of the present invention include peptides or polypeptides which arise as a result of the existence of alternative translational and post-translational events.

In illustrative examples, the polypeptide antigen may comprise an amino acid sequence that shares at least 50% (and at least 51% to at least 99% and all integer percentages in between) sequence similarity or sequence identity with a tick polypeptide sequence as set forth in any one of SEQ ID NO: 1 to 17 or SEQ ID NOs 36 to 98 or 103, or a fragment of such polypeptides.

In other illustrative embodiments, the polypeptide antigen may be derived from a functional orthologue of any of the tick polypeptides described herein. By way of an illustrative example, the tick polypeptide can be a functional orthologue of a polypeptide derived from any one of *R. microplus* clades, *R. annulatus, R. microplus*, etc.

The present invention contemplates full-length tick polypeptides as well as their biologically (e.g., immunologically) active fragments. Typically, biologically active fragments of a full-length tick polypeptide may participate in an interaction, for example, an intra-molecular or an inter-molecular interaction and/or are capable of stimulating an immune response to the tick polypeptide. Such biologically active fragments include peptides comprising amino acid sequences sufficiently similar to or derived from the amino acid sequences of a (putative) full-length tick polypeptide, for example, the peptide fragment amino acid sequences set forth Table 1, which include fewer amino acids than a the full-length tick polypeptide from which they are derived, and retain the ability to elicit an immune response (e.g., a cellular immune response and/or a humoral immune response) to the native tick polypeptide. Typically, biologically active fragments will comprise a domain or motif with at least one activity (i.e., an immunostimulatory activity) of a putatively full-length tick polypeptide.

The present invention also contemplates tick polypeptides that are variants of wild-type or naturally-occurring tick polypeptides or their biologically active fragments. Such "variant" peptides or polypeptides include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Non-limiting examples of such variant tick polypeptides include processed forms of a full-length or precursor tick polypeptide, including but not limited to peptides or polypeptides in which the signal peptide domain and/or any pro-regions are removed from the precursor form.

Variant proteins encompassed by the present invention are biologically (e.g., immunologically) active, that is, they continue to possess the desired biological activity of the native protein. Such variants may result from, for example, genetic polymorphism or from human manipulation.

A tick polypeptide may be altered in various ways including amino acid substitutions, deletions, truncations, and insertions. Methods for such manipulations are generally known in the art. For example, amino acid sequence variants of tick polypeptides can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein.

Guidance as to appropriate amino acid substitutions that do not affect biological activity of the protein of interest may be found in the model of Dayhoff et al., (1978) Atlas of Protein Sequence and Structure (*Natl. Biomed. Res. Found.*). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of tick polypeptides. Recursive ensemble mutagenesis (REM), a technique which enhances the frequency of functional mutants in the libraries, can be used in combination with the screening assays to identify tick polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Variant tick polypeptides may contain conservative amino acid substitutions at various locations along their sequence, as compared to a parent (e.g., naturally-occurring or reference) tick amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

Dependent on their structural properties, amino acid residues may fall in two or more classes. For the naturally-occurring protein amino acids, sub-classification according to this scheme is presented in Table 6.

TABLE 6

Amino acid sub-classification

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Nonpolar/neutral | Alanine, Glycine, Isoleucine, Leucine, Methionine, Phenylalanine, Proline, Tryptophan, Valine |
| Polar/neutral | Asparagine, Histidine, Glutamine, Cysteine, Serine, Threonine, Tyrosine |
| Polar/negative | Aspartic acid, Glutamic acid |
| Polar/positive | Lysine, Arginine |
| Polar/large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional tick polypeptide can readily be determined by assaying its activity. Conservative substitutions are shown in Table 7 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 7

Exemplary and Preferred Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., Biochemistry, third edition, William C. Brown Publishers (1993).

Accordingly, the present invention also contemplates as tick polypeptides, variants of the naturally-occurring tick polypeptide sequences or their biologically-active fragments, wherein the variants are distinguished from the naturally-occurring sequence by the addition, deletion, or substitution of one or more amino acid residues. In general, variants will display at least about 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% similarity to a parent or reference tick polypeptide sequence as, for example, set forth in SEQ ID NO: 1, 3, 5, 7, 9, or 11, as determined by sequence alignment programs described elsewhere herein using default parameters. Desirably, variants will have at least 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity to a parent tick polypeptide sequence as, for example, set forth in SEQ ID NO: 1, 3, 5, 7, 9, or 11, as determined by sequence alignment programs described elsewhere herein using default parameters.

Variants of a wild-type tick polypeptide, which fall within the scope of a variant polypeptide, may differ from the wild-type molecule generally by as much as 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, or 11 amino acid residues or suitably by as few as 10, 9, 8, 7, 6, 5, 4, 3, 2, or 1 amino acid residue(s). In some embodiments, a variant polypeptide differs from the corresponding sequences in SEQ ID NO: 1, 3, 5, 7, 9, or 11, by at least 1 but by less than or equal to 25, 24, 23, 22, 21, 20, 19, 18, 17, 16, 15, 14, 13, 12, 11, 10, 9, 8, 7, 6, 5, 4, 3, or 2 amino acid residues. In other embodiments, it differs from the corresponding sequence in any one of SEQ ID NO: 1, 3, 5, 7, 9, or 11, by at least one 1% but less than or equal to 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3% or 2% of the residues. If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution, as discussed in more detail below.

The polypeptide antigens of the present invention also encompass tick polypeptides comprising amino acids with modified side chains, incorporation of unnatural amino acid residues and/or their derivatives during peptide, polypeptide or protein synthesis and the use of cross-linkers and other methods which impose conformational constraints on the peptides, portions and variants of the invention. Examples of side chain modifications include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4, 6-trinitrobenzene sulphonic acid (TNBS).

The carboxyl group may be modified by carbodiimide activation via O-acylisourea formation followed by subsequent derivatization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

The polypeptide antigens of the present invention also include peptides and polypeptides that are encoded by polynucleotides that hybridize under stringency conditions as defined herein, especially medium or high stringency conditions, to tick polypeptide-encoding polynucleotide sequences, or the non-coding strand thereof, as described below. Illustrative tick polynucleotide sequences are set forth in SEQ ID NOs: 104 to 107 or their complements (representing exemplary polynucleotide sequences encoding TC9753, TC12142, TC5995, and TC8992, respectively). It will be well within the purview of the skilled person to design polynucleotide sequences encoding the polypeptides described herein.

The skilled person will be familiar with methods for determining the percentage sequence identity between two amino acid or nucleic acid sequences.

Variants of a native tick polypeptide can be identified by screening combinatorial libraries of mutants, e.g., truncation mutants, of a tick polypeptide. Libraries or fragments e.g., N terminal, C terminal, or internal fragments, of a tick polypeptide coding sequence can be used to generate a variegated population of fragments for screening and subsequent selection of variants of a reference tick polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of tick polypeptides.

The polypeptide antigens of the present invention may be prepared by any suitable procedure known to those of skill in the art. For example, the polypeptide antigens may be produced by any convenient method such as by purifying the peptides or polypeptides from naturally-occurring reservoirs including ticks. Methods of purification include size exclusion, affinity or ion exchange chromatography/separation. The identity and purity of derived polypeptide antigen is determined for example by SDS-polyacrylamide electrophoresis or chromatographically such as by high performance liquid chromatography (HPLC). Alternatively, the polypeptide antigens may be synthesized by chemical synthesis (e.g., using solution synthesis or solid phase synthesis as described, for example, in Chapter 9 of Atherton and Shephard (supra) and in Roberge et al., (1995, *Science,* 269: 202)).

2.2 Immunogens

In some embodiments, the at least one polypeptide antigen of the present invention is conjugated to a carrier protein which suitably comprises at least one T-cell epitope. One such carrier protein is the Keyhole Limpet Hemocyanin (KLH) carrier protein (e.g., UniProtKB accession no. Q531P9; SEQ ID NO: 18), which beneficially contains multiple T-cell epitopes. Alternative carrier proteins that are suitable for use with the present invention include, but are not limited to, Concholepas Concholepas Hemocyanin (CCH) (UniProtKB accession no. P84619 and P84620; SEQ ID NO: 30 and 31, respectively), ovalbumin (e.g., UniProtKB accession no. P01012; SEQ ID NO: 32), bovine serum albumin (e.g., UniProtKB accession no. P02769; SEQ ID NO: 33), and cholera toxin B (e.g., UniProtKB accession no. P01556; SEQ ID NO: 34).

2.3 Promiscuous T-Cell Epitopes

In some embodiments, the immunogenic agents of the invention also comprise a promiscuous T-cell epitope (e.g., a heterologous CD4+ T-cell epitope) in order to prepare a composition of greater immunological efficacy. Promiscuous T-cell epitopes that are suitable for use with the immunogenic polypeptide molecules of the present invention are typically associated with the class II major histocompatibility complex (MHC), and can be derived from naturally occurring immunogens derived from any pathogenic microorganism. Naturally occurring promiscuous T-cell epitopes can also be conservatively modified by single or multiple amino acid additions, deletions, or substitutions (e.g., within classes of charged, hydrophilic/hydrophobic, steric amino acids) to obtain candidate sequences that can be screened for their ability to enhance immunogenicity.

Non-naturally occurring promiscuous T-cell epitopes can be artificially synthesized to obtain sequences that have comparable or greater immunogenicity. Artificial promiscuous T-cell epitopes (e.g., heterologous CD4+ T-cell epitopes) can range in size from about 7 to about 50 amino acid residues in length and can have structural features such as amphipathic helices (alpha-helical structures with hydrophobic amino acid residues dominating one face of the helix and charged or polar residues dominating the surrounding faces). The promiscuous T-cell epitopes may also contain additional primary amino acid patterns, such as a glycine or a charged residue followed by two to three hydrophobic residues, followed in turn by a charged or polar residue (i.e., a Rothbard sequence). In addition, promiscuous T-cell epitopes often conform with the "1, 4, 5, 8 rule", where a positively charged residue is followed by hydrophobic residues at the fourth, fifth, and eighth positions after the charged residue.

These features may be incorporated into the designs of artificial promiscuous T-cell epitopes. Variable positions and preferred amino acids are available for MHC-binding motifs (see, Meister et al., *Vaccine,* 1995, 13:581-591). For example, the degenerate promiscuous T-cell epitope described in the International Patent Publication No. WO95/11998 as SSAL1TH1 has the degenerate sequence (Asp/Glu)-(Leu/Ile/Val/Phe)-Ser-(Asp/Gly)-(Leu/Ile/Val/Phe)-(Lys/Arg)-Gly-(Leu/Ile/Val/Phe)-(Leu/Ile/Val/Phe)-(Leu/Ile/Val/Phe)-His-(Lys/Arg)- Leu/Ile/Val/Phe)-(Asp/Glu)-Gly-(Leu/Ile/Val/Phe).

Given this structural-functional guidance, it should be understood that many candidates for artificial promiscuous T-cell epitopes can be generated by conventional methods and screened for their ability to enhance the immune response of an associated antigen.

By way of an example, particular promiscuous T-cell epitopes useful in the embodiments disclosed herein include measles virus protein F amino acid sequence LSEIKGVIVHRLEGV (SEQ ID NO: 21); and tetanus toxin (UniProtKB accession no. P04958; SEQ ID NO: 22) including for example peptides with any of the amino acid sequences VDDALINSTKIYSYFPSV (SEQ ID NO: 23), QYIKANSKFIGITEL (SEQ ID NO: 24), or FNNFTVSFWLRVPKVSASHLE (SEQ ID NO: 25). Yet other tetanus toxin-derived peptide amino acid sequences that are suitable for use as promiscuous T-cell epitopes may be selected from residues 590-603, 615-629, 639-652, 830-843, and 947-967 of the full-length native tetanus toxin amino acid sequence set forth in SEQ ID NO: 22.

Still other useful promiscuous T-cell epitopes include amino acid residues 378-398 of Malaria *Plasmodium falciparum* CSP protein (i.e., the amino acid sequence DEKKIAKMEKASSVFNVVNS; SEQ ID NO: 27). Useful CMV CTL epitopes include $pp65_{13-24}$; $pp65_{417-426}$; $pp65_{265-275}$; $pp65_{363-373}$; $pp65_{369-379}$; $pp65_{369-379}$: $pp65_{188-195}$; $pp65_{186-196}$; $pp65_{367-379}$; and particularly $pp65_{495-503}$ (i.e., NLVPMVATV; SEQ ID NO: 35).

Yet other promiscuous T-cell epitopes include hepatitis B surface and core antigen helper T-cell epitopes, *Chlamydia trachomatis* major outer membrane protein helper T-cell epitopes, diphtheria toxin helper T-cell epitopes, *Schistosoma mansoni* triose phosphate isomerase helper T-cell epitopes; *E. coli* TraT helper T-cell epitopes; PADRAE (SEQ ID NO: 29); and human immunodeficiency virus-1.

Various other promiscuous T-cell epitopes are described in U.S. Pat. Nos. 5,759,552, 6,107,021, and 6,783,761; and in U.S. Patent Publication No. 2004/0086524, and the references therein.

Non-limiting examples of promiscuous T-cell epitopes that are particularly useful in the embodiments described herein are listed in Table 8.

TABLE 8

| Epitope | Peptide Sequence | SEQ ID NO: |
|---|---|---|
| Measles protein F 289-302 | LSEIKGVIVHRLEGV | 21 |
| Tetanus toxin 583-599 | VDDALINSTKIYSYFPSV | 23 |
| Tetanus toxin 830-844 | QYIKANSKFIGITEL | 24 |
| *Anaplasma marginale* | SSAGGQQQESS | 26 |
| Influenza HA B epitope | SKAFSNCYPYDVPDYASL | 28 |
| PADRE | AKXVAAWTLKAA | 29 |

Another useful epitope is ENDIEKKICKMEKCSSVFNV (Circumsporozoite (CS) protein).

Yet another useful immunogenic protein, although not strictly a promiscuous T-cell epitope, is a cholera toxin B epitope (CTB).

2.4 Linker Sequences

The polypeptide antigen may be separated from another moiety (e.g., an immunogenic carrier protein, or promiscuous T-cell epitope) by any suitable linker known in the art. The linker generally includes any amino acid residue that cannot be unambiguously assigned either component. Linkers are frequently used in the field of protein engineering to interconnect different functional units, e.g., in the creation of single-chain variable fragment (scFv) constructs derived from antibody variable light (VL) and variable heavy (VH) chains. They are generally conformationally flexible in solution, and are suitably and predominantly composed of polar amino acid residue types. Typical (frequently used) amino acids in flexible linkers are serine and glycine. Less preferably, flexible linkers may also include alanine, threonine and proline. Thus, an intervening linker suitable for use in the present invention is preferably flexible in conformation to ensure relaxed (unhindered) association of the tick polypeptide and carrier protein. Suitable linkers for use in the polypeptides envisaged herein will be clear to the skilled person, and may generally be any linker used in the art to link amino acid sequences, as long as the linkers are structurally flexible, in the sense that they do not affect the activity of either component being conjugated.

In some embodiments, the at least one polypeptide antigen is conjugated to the carrier protein (or an intervening linker sequence) by way of a cysteine amino acid residue.

Alternatively, the skilled person will be able to determine the optimal linkers, optionally after performing a limited number of routine experiments. The intervening linker is suitably an amino acid sequence generally consisting of at least 1 amino acid residue and usually consisting of at least 2 amino acid residues, with a non-critical upper limit chosen for reasons of convenience being about 100 amino acid residues. In particular embodiments, the linker consists of about 1 to about 20 amino acid residues, or about 20 to about 40 amino acid residues, usually about 1 to about 10 amino acid residues, typically about 1 to about 15 amino acid residues. In particular, non-limiting embodiments, at least 50% of the amino acid residues of a linker sequence are selected from the group proline, glycine, and serine. In further non-limiting embodiments, at least 60%, such as at least 70%, such as for example 80% and more particularly 90% of the amino acid residues of a linker sequence are selected from the group proline, glycine, and serine. In other particular embodiments, the linker sequences essentially consist of polar amino acid residues; in such particular embodiments, at least 50%, such as at least 60%, such as for example 70% or 80% and more particularly 90% or up to 100% of the amino acid residues of a linker sequence are selected from the group consisting of glycine, serine, threonine, alanine, proline, histidine, asparagine, aspartic acid, glutamine, glutamic acid, lysine and arginine. In specific embodiments, linker sequences may include $[GGSG]_nGG$, $[GGGGS]_n$, $[GGGGG]_n$, $[GGGKGGGG]_n$, $[GGGNGGGG]_n$, $[GGGCGGGG]_n$, wherein n is an integer from 1 to 10, suitably 1 to 5, more suitably 1 to 3.

In addition to spacing the polypeptide antigen from any other component, the linker may comprise one or more ancillary functionalities. For example, the linker may comprise a purification moiety that facilitates purification of the immunostimulatory polypeptide.

Purification moieties typically comprise a stretch of amino acids that enables recovery of the chimeric polypeptide through affinity binding. Numerous purification moieties or 'tags' are known in the art, illustrative examples of which include biotin carboxyl carrier protein-tag (BCCP-tag), Myc-tag (c-myc-tag), Calmodulin-tag, FLAG-tag, HA-tag, His-tag (Hexahistidine-tag, His6, 6H), Maltose binding protein-tag (MBP-tag), Nus-tag, Chitin-binding protein-tag (CBP-tag) Glutathione-S-transferase-tag (GST-tag), Green fluorescent protein-tag (GFP-tag), Polyglutamate-tag, Amyloid beta-tag, Thioredoxin-tag, S-tag, Softag 1, Softag 3, Strep-tag, Streptavidin-binding peptide-tag (SBP-tag), biotin-tag, streptavidin-tag and V5-tag.

2.5 Combination with Other Tick Antigens.

The compositions described above and elsewhere herein may be combined with other tick antigens known the art. For example, the Bm86 and Bm91 antigens described in International Patent Publication Nos. WO1988/003929 (identified as WGL+) and WO1995/004827 (both of which are incorporated herein in their entirety), have been shown to have some protective activity. Therefore, in some embodiments the composition of the present invention further comprises a Bm86 polypeptide antigen, or a fragment thereof. In some embodiments, the Bm86 polypeptide antigen comprises, consists, or consists essentially of the full length native Bm86 polypeptide sequence from *R. microplus*, as follows:

[SEQ ID NO: 99]
MAARSGSSAADRFVAVALLATALYATAAADNFDTYLATLSNVSALIKDEA

MGVAFIEGLNDPYTTINNVDSSSSWDYASNITDYNQNMSNKVSTEVSKME

RQFGITAKRFDWHNFKNDSLKRLFRHVATIGLAALPDDKLENATSLSSKM

AAIYGSTKVTVGKDKDLPLEPDLTRNMKEVGNYDKLLQTWLAWHNAVGPA

IKQYYIPYIKLSNEAASLDGYDNIKSAWLSDYETENMTEIVDKLWEDLSP

LYKKLHAYVRMKLREIYPGRLPEDGTIPAHLLGNMWAQEWGTLYPHLTME

DKPLDISKTMVEQKWDAQKMFHAAEDFFTSLGLDNMTSEFWSKSILTKPE

DREIQCHASAWNMYNGDDFRIKMCTDPSVEELRTVHHEMGHIEYYMQYKH

LHVLLQEGANEGFHEAVGDLIALSVATKTHYGKLSLLKPTDKYNAVDLLL

MSALDKIAFLPFGYLLDKWRWTIFTGETPFDKMNEKFWEYRIKYQGVSPP

VKRNESFFDGGAKYHVALHVPYLRYFVAFILQFQFHEHLCTVAKKVDEHH

PFHECDIYGEKNAGDVLKKGLSLGRSKPWPDVLEIMAGTRQMSASSLKKY

YEPLEKWLDERIKNEVVGWDKANVQDYMGVPSFANKVDFSAAAVLASIGV

ILFCWKNISL.

In some embodiments, an immunogenic fragment of the full length native Bm86 sequence is used. For example, suitable fragments include, but are not limited to WRWTIFTGETPFQK, LREIYPG, NEVVGWDK, LWEDLSPLYK, QYYIPYIK, and YYEPLEK. In some of the same and other embodiments, the Bm86 polypeptide antigen comprises a fusion protein of two, three, or more antigenic peptides derived from the full length Bm86 protein. Each antigenic peptide may be conjugated directly to the previous antigenic peptide, or alternatively linked via an amino acid linked. Suitable Bm86 fusion proteins include those described in U.S. Pat. No. 8,110,202, the entire content of which is incorporated herein by reference. Particularly suitable Bm86 fusion proteins include those designated SBm4912, SBm7462, and SBm19733, with the amino acid sequences listed in Table 9.

TABLE 9

| Bm86 Fusion Protein | Amino acid sequence |
|---|---|
| SBm4912 | CLSKHVLRKLQACEHSSICSDFG NEFCRNACDCGEWGAMNMTTR C (SEQ ID NO: 100) |
| SBm7462 | CLSKHVLRKLQACEHCDCGEWG AMNMTTRSSICSDFGNEFCRNA C (SEQ ID NO: 101) |
| SBm19733 | CLSKHVLRKLQACEHKEKSSICS DFGNEFCRNAKEKCDCGEWGA MNMTTRC (SEQ ID NO: 102) |

3. Nucleic Acid Molecules

In some embodiments, the immunogenic agents of the invention are prepared by recombinant techniques. For example, the agents may be prepared by a procedure including the steps of: (a) preparing a construct comprising a polynucleotide sequence that encodes an immunogenic agent and that is operably linked to a regulatory element; (b) introducing the construct into a host cell; (c) culturing the host cell to express the polynucleotide sequence to thereby produce the encoded immunogenic agent; and (d) isolating the immunogenic agent from the host cell. In illustrative examples, the nucleotide sequence encodes at least a biologically active portion of the sequences set forth in SEQ ID NO: 1, 3, 5, 7, 9, or 11, or a variant thereof. For example, the nucleic acid molecule may encode the polypeptide sequence set forth in any one of SEQ ID NO: 29-43. Recombinant polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

Exemplary nucleotide sequences that encode the polypeptides of the invention encompass full-length tick polypeptide genes, as well as portions of the full-length or substantially full-length nucleotide sequences of the tick polypeptide genes or their transcripts or DNA copies of these transcripts.

The invention also contemplates nucleic acid molecules that correspond to variant nucleic acid sequences encoding the tick polypeptide. Nucleic acid variants can be naturally-occurring, such as allelic variants (same locus), homologues (different locus), and orthologues (different organism) or can be non naturally-occurring. Naturally-occurring nucleic acid variants (also referred to herein as polynucleotide variants) such as these can be identified with the use of well-known molecular biology techniques, as, for example, with polymerase chain reaction (PCR) and hybridization techniques as known in the art. Non-naturally occurring polynucleotide variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of the native tick polypeptide. Variant nucleotide sequences also include synthetically derived nucleotide sequences, such as those generated, for example, by using site-directed mutagenesis but which still encode a tick polypeptide. Generally, variants of a particular tick polypeptide coding sequence will have at least about 40%, 45%, 50%, 51%, 52%, 53%, 54%, 55%, 56%, 57%, 58%, 59% 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular coding sequence as determined by sequence alignment programs described elsewhere herein using default parameters.

Tick polypeptide-encoding nucleotide sequences can be used to isolate corresponding sequences and alleles from other organisms, particularly other tick species. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other tick polypeptide-coding sequences present in a population of cloned genomic DNA fragments or cDNA fragments (i.e., genomic or cDNA libraries) from a chosen organism (e.g., a tick). Accordingly, the present invention also contemplates polynucleotides that hybridize to reference tick polypeptide-encoding nucleotide sequences, or to their complements, (e.g., SEQ ID NO: 104, 104, 106, and 107 or their complements) under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6.

In certain embodiments, a tick polypeptide is encoded by a polynucleotide that hybridizes to a disclosed nucleotide sequence under very high stringency conditions. One embodiment of very high stringency conditions includes hybridizing 0.5 M sodium phosphate, 7% SDS at 65° C., followed by one or more washes at 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

3.1 Expression Vectors

In some embodiments, the polypeptide antigen can be produced inside a cell (for example, an antigen-presenting cell) by introduction of one or more expression constructs that encode the polypeptide antigen. As described, for example, in U.S. Pat. No. 5,976,567 (Inex), the expression of natural or synthetic nucleic acids is typically achieved by operably linking a nucleic acid of interest to a regulatory element (e.g., a promoter, which may be either constitutive or inducible), suitably incorporating the construct into an expression vector, and introducing the vector into a suitable host cell. Typical vectors contain transcription and translation terminators, transcription and translation initiation sequences and promoters useful for regulation of the expression of the particular nucleic acid. The vectors optionally comprise generic expression cassettes containing at least one independent terminator sequence, sequences permitting replication of the cassette in eukaryotes, prokaryotes, or both (e.g., shuttle vectors) and selection markers for both prokaryotic and eukaryotic systems. Vectors may be suitable for replication and integration in prokaryotes, eukaryotes, or both (see, Giliman and Smith (1979), Gene 8: 81-97; Roberts et al. (1987), Nature 328: 731-734; Berger and Kimmel, Guide to Molecular Cloning Techniques, Methods in Enzymology, volume 152, Academic Press, Inc., San Diego, Calif. (Berger); Sambrook et al. (1989), MOLECULAR CLONING—A LABORATORY MANUAL (2nd ed.) Vol. 1-3, Cold Spring Harbor Laboratory, Cold Spring Harbor Press, N.Y., (Sambrook); and F. M. Ausubel et al., CURRENT PROTOCOLS IN MOLECULAR BIOLOGY, eds., Current Protocols, a joint venture between Greene Publishing Associates, Inc. and John Wiley & Sons, Inc., (1994 Supplement) (Ausubel)).

Expression vectors containing regulatory elements from eukaryotic viruses such as retroviruses are typically used for expression of nucleic acid sequences in eukaryotic cells. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

A regulatory polynucleotide suitably comprises transcriptional and/or translational control sequences, which will generally be appropriate for the host cell used for expression of the antigen-encoding polynucleotide. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the host cell to be introduced or may be derived from an alternative source, where the region is functional in the host cell.

The synthetic construct of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by the presence of homology to the canonical form 5' AATAAA-3' although variations are not uncommon. The 3' non-translated regulatory DNA sequence preferably includes from about 50 to 1,000 nucleotide base pairs and may contain transcriptional and translational termination sequences in addition to a polyadenylation signal and any other regulatory signals capable of effecting mRNA processing or gene expression.

In a preferred embodiment, the expression vector further contains a selectable marker gene to allow the selection of transformed host cells. Selection genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide. In order to express said fusion polypeptide, it is necessary to ligate an antigen-encoding polynucleotide according to the invention into the expression vector so that the translational reading frames of the fusion partner and the polynucleotide coincide. Well known examples of fusion partners include, but are not limited to, glutathione-S-transferase (GST), Fc portion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAEXPRESS™ system (Qiagen) useful with (His$_6$) fusion partners and the Pharmacia GST purification system. In a preferred embodiment, the recombinant polynucleotide is expressed in the commercial vector pFLAG as described more fully hereinafter. Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localisation of the fusion polypeptide of the invention, or for isolating cells which express the fusion polypeptide of the invention. Flow cytometric methods such as fluorescence activated cell sorting (FACS) are particularly useful in this latter application. Preferably, the fusion partners also have protease cleavage sites, such as for factor X$_a$ or thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation. Fusion partners according to the invention also include within their scope "epitope tags", which are usually short peptide sequences for which a specific antibody is available. Well known examples of epitope tags for which specific monoclonal antibodies are readily available include c-Myc, influenza virus haemagglutinin and FLAG tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding a polypeptide, biologically active fragment, variant or derivative according to the invention. The conditions appropriate for protein expression will vary with the choice of expression vector and the host cell. This is easily ascertained by one skilled in the art through routine experimentation. Suitable host cells for expression may be prokaryotic or eukaryotic. Preferred host cells for expression of a polypeptide according to the invention include bacteria and yeast. The bacterium used may be *Escherichia coli*. The yeast may be *Pichia pastoris*. Alternatively, the host cell may be an insect cell such as, for example, Sf9 cells that may be utilised with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6.

Alternatively, the modified antigen may be synthesised using solution synthesis or solid phase synthesis as described, for example, in Chapter 9 of Atherton and Shephard (supra) and in Roberge et al. (1995, *Science* 269: 202).

While a variety of vectors may be used, it should be noted that viral expression vectors are useful for modifying eukaryotic cells because of the high efficiency with which the viral vectors transfect target cells and integrate into the target cell genome. Illustrative expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2), 205-208), Vigna and Naldini (2000, *J. Gene Med.* 2(5), 308-316), Kay et al. (2001, *Nat. Med.* 7(1), 33-40), Athanasopoulos, et al. (2000, *Int. J. Mol. Med.* 6(4): 363-375) and Walther and Stein (2000, *Drugs* 60(2): 249-271).

The polypeptide-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the polypeptide antigen in a mammalian (e.g., cattle) host using methods that take advantage of codon usage bias, or codon translational efficiency in specific mammalian (e.g., cattle) cell or tissue types as set forth, for example, in International Patent Publication Nos. WO99/02694 and WO00/42215. Briefly, these latter methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5%, 10%, 15%, 20%, 25%, 30%, more preferably 35%, 40%, 50%, 60%, 70% (and every percentage integer in between) or more of the existing codons of a parent polynucleotide.

The expression vector is compatible with the antigen-presenting cell in which it is introduced such that the antigen-encoding polynucleotide is expressible by the cell. The expression vector is introduced into the antigen-presenting cell by any suitable means which will be dependent on the particular choice of expression vector and antigen-presenting cell employed. Such means of introduction are well-known to those skilled in the art. For example, introduction can be effected by use of contacting (e.g., in the case of viral vectors), electroporation, transformation, transduction, conjugation or triparental mating, transfection, infection membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art. Alternatively, the vectors are introduced by means of cationic lipids, e.g., liposomes. Such liposomes are commercially available (e.g., LIPOFECTIN®, LIPOFECTAMINE™, and the like, supplied by Life Technologies, Gibco BRL, Gaithersburg, Md.).

4. Construct Systems

The present invention may utilise any construct system for eliciting simultaneously a host-protective antibody response and a cell-mediated immune response against a tick polypeptide to therapeutically and/or prophylactically treat a tick infestation. The strategy involves administering to an individual a first antigen corresponding to the tick polypeptide, and being suitably intracellularly resistant to proteolysis. In addition, a second antigen, corresponding to a modified form of the tick polypeptide, is administered to the individual, wherein the rate of intracellular proteolytic degradation of the second antigen is increased, enhanced or otherwise elevated relative to the first antigen. The first and second antigens may be administered in directly (i.e., in the form of polypeptides), or "indirectly" (for example in the form of a nucleic acid encoding said polypeptides), or a combination thereof. The antigenic determinant(s) or epitope(s) of the first antigen and the second antigen may be the same or different.

Accordingly, the epitope-containing sequence of the first antigen and the second antigen may be the same or different. Preferably, the first antigen and the second antigen comprise the same epitope(s). Suitably, when corresponding epitopes are different between the first antigen and the second antigen, such epitopes are preferably capable of eliciting the production of elements that bind to a corresponding epitope of the tick polypeptide.

4.1 Production of Modified Antigen

The second or modified antigen according to the present invention may be prepared using any suitable technique that renders it less resistant to proteolysis intracellularly relative to a first antigen corresponding to the tick polypeptide of interest. However, it should be noted that the present invention is not dependent on, and not directed to, any one particular technique by which the second or modified antigen is produced. The intracellular half life of a first or tick polypeptide is suitably greater than about 3 minutes, preferably greater than about 5 minutes, more preferably greater than about 10 minutes, even more preferably greater than about 15 minutes, even more preferably greater than about 30 minutes, even more preferably greater than about 1 hour, even more preferably greater than about 10 hours, even more preferably greater than about 24 hours, and still even more preferably greater than about 50 hours. Suitably, a proteolytically resistant antigen is one that retains greater than about 10% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. Preferably, a proteolytically resistant antigen is one that retains greater than about 20% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. More preferably, a proteolytically resistant antigen is one that retains greater than about 50% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 24 hours, and still even more preferably after about 50 hours at intracellular or intracellular-like conditions. The intracellular or intracellular-like conditions are preferably physiological for the cell type. The cell type is preferably an antigen presenting cell, more preferably a professional antigen presenting cell including, but not restricted to, a dendritic cell, a macrophage and a B cell. The temperature of the intracellular or intracellular-like conditions is preferably physiological for the cell type. Exemplary temperatures for mammalian cells range suitably from about 30° C. to about 42° C., and preferably from about 35° C. to about 37° C. The intracellular half life of the second antigen is suitably less than about 50 hours, preferably less than about 10 hours, more preferably less than about 1 hour, even more preferably less than about 30 minutes, even more preferably less than about 15 minutes, even more preferably less than about 10 minutes and still even more preferably less than about 3 minutes. At a minimum, enhanced proteolytic degradation of the second antigen refers to a level of proteolytic degradation that is at least about 5%, preferably at least about 10%, more preferably at least about 20%, even more preferably at least about 40%, even more preferably at least about 50%, even more preferably at least about 60%, even more preferably at least about 70%, even more preferably at least about 80%, even more preferably at least about 90%, still even more preferably at least about 95%, greater than that of the target or first antigen. Assays for measuring degradation of proteins are known to persons of skill in the art. For example, proteolytic degradation may be measured using a mammalian cell lysate assay including, but not restricted to, the reticulocyte lysate assay of Bachmair et al. in U.S. Pat. No. 5,646,017.

The second antigen may be derived from or correspond to the tick polypeptide. Preferably, the second antigen is modified to include an intracellular degradation signal or degron. The degron is suitably an ubiquitin-mediated degradation signal selected from an ubiquitin acceptor, an ubiquitin or combination thereof.

In another embodiment, the second antigen is modified to include, or is otherwise associated with, an ubiquitin acceptor which is a molecule that preferably contains at least one residue appropriately positioned from the N-terminal of the antigen as to be able to be bound by ubiquitin polypeptides. Such residues preferentially have an epsilon amino group such as lysine. Physical analysis demonstrates that multiple lysine residues function as ubiquitin acceptor sites (see, King et al., 1996, *Mol. Biol. Cell* 7: 1343-1357; and King et al., 1996, *Science* 274: 1652-1659). Examples of other ubiquitin acceptors include lacI or Sindis virus RNA polymerase.

In yet another embodiment, the second antigen is conjugated to a ubiquitin polypeptide to produce a second or modified antigen whose rate of intracellular proteolytic degradation is increased, enhanced or otherwise elevated relative to the parent antigen. Ubiquitination at the N-terminal of the protein specifically targets the protein for degradation via the ubiquitin-proteosome pathway. In a preferred embodiment of this type, the ubiquitin polypeptide is fused, or otherwise conjugated, to the second antigen. Suitably, the ubiquitin polypeptide is of mammalian origin, more preferably of bovine or other ungulate origin. In an exemplary embodiment of this type, the ubiquitin polypeptide comprises the amino acid sequence set forth in SEQ ID NO: 19 (ubiquitin from *Bos taurus*; UniProtKB accession no. P63048). In a more specific embodiment of this type, the ubiquitin polypeptide comprises, consists, or consists essentially of the amino acid sequence set forth in amino acid residues 1-76 of the sequence set forth in SEQ ID NO: 19. In some other embodiments, the ubiquitin polypeptide comprises two or more copies of the sequence set forth in SEQ ID NO: 19 or of residues 1-76 of SEQ ID NO: 19.

In some embodiments, the ubiquitin-antigen fusion protein is suitably produced by covalently attaching an antigen corresponding to the tick polypeptide to a ubiquitin or a biologically active fragment thereof. Covalent attachment may be effected by any suitable means known to persons of skill in the art. For example, protein conjugates may be prepared by linking proteins together using bifunctional reagents. The bifunctional reagents can be homobifunctional or heterobifunctional.

Other protein processing signals that destabilise an antigen of interest and allow for enhanced intracellular degradation are contemplated in the present invention. These other methods may not necessarily be mediated by the ubiquitin pathway, but may otherwise permit degradation of proteins in the cytoplasm via proteosomes. For example, the present invention contemplates the use of other intracellular processing signals which govern the rate(s) of intracellular protein degradation including, but not limited to, those described by Bohley et al. (1996, *Biol. Chem. Hoppe. Seyler* 377: 425-435). Such processing signals include those that allow for phosphorylation of the target protein (Yaglom et al., 1996, *Mol. Cell Biol.* 16: 3679-3684; Yaglom et al., 1995, *Mol. Cell Biol.* 15: 731-741). Also contemplated by the present invention are modification of an parent antigen that allow for post-translational arginylation (Ferber et al. 1987, *Nature* 326: 808-811; Bohley et al., 1991, *Biomed. Biochim. Acta* 50: 343-346) of the protein which can enhance its rate(s) of intracellular degradation. The present invention also contemplates the use of certain structural features of proteins that can influence higher rates of intracellular protein turn-over, including protein surface hydrophobicity, clusters of hydrophobic residues within the protein (Sadis et al., 1995, *Mol. Cell Biol.* 15: 4086-4094), certain hydrophobic pentapeptide motifs at the protein's carboxy-terminus (C-terminus) (e.g., ARINV, as found on the C-terminus of ornithine decarboxylase (Ghoda et al., 1992, *Mol. Cell Biol.* 12: 2178-2185; Li, et al., 1994, *Mol. Cell Biol.* 14: 87-92), or AANDENYALAA (as found in C-terminal tags of aberrant polypeptides (Keiler et al., 1996, *Science* 271: 990-993) or PEST regions (regions rich in proline (P), glutamic acid (E), serine (S), and threonine (T), which are optionally flanked by amino acids comprising electropositive side chains (Rogers et al. 1986, *Science* 234 (4774): 364-368; 1988, *J. Biol. Chem.* 263: 19833-19842). Moreover, certain motifs have been identified in proteins that appear necessary and possibly sufficient for achieving rapid intracellular degradation. Such motifs include RXALGXIXN region (where X=any amino acid) in cyclins (Glotzer et al., 1991, *Nature* 349: 132-138) and the KTKRNYSARD motif in isocitrate lyase (Ordiz et al., 1996, *FEBS Lett.* 385: 43-46).

In an alternate embodiment, a ubiquitin-antigen fusion protein is suitably expressed by a synthetic chimeric polynucleotide comprising a first nucleic acid sequence, which encodes a polypeptide antigen that comprises an amino acid sequence that corresponds to the tick polypeptide, and which is linked downstream of, and in reading frame with, a second nucleic acid sequence encoding a ubiquitin or biologically active fragment thereof. In a preferred embodiment of this type, the second polynucleotide comprises a first nucleic acid sequence, which encodes a polypeptide antigen comprising an amino acid sequence corresponding to the tick polypeptide, and which is linked immediately adjacent to, downstream of, and in reading frame with, a second nucleic acid sequence encoding a ubiquitin or biologically active fragment thereof. In another embodiment, the second polynucleotide comprises a first nucleic acid sequence, which encodes an antigen corresponding to the tick polypeptide, and which is linked upstream of, and in reading frame with, a second nucleic acid sequence encoding a ubiquitin or biologically active fragment thereof. In yet another embodiment of this type, the second polynucleotide comprises a first nucleic acid sequence, which encodes an antigen corresponding to the tick polypeptide, and which is linked immediately adjacent to, upstream of, and in reading frame with, a second nucleic acid sequence encoding a ubiquitin or biologically active fragment thereof. For example, when the subject being administered with the vaccine is bovine, the ubiquitin-encoding nucleic acid sequence comprises the following nucleic acid sequence:

```
                                           (SEQ ID NO: 45)
ATGCAGATCTTTGTGAAGACCCTGACGGGCAAGACCATCACCCTTGAGGT

CGAGCCCAGTGACACCATTGAGAATGTCAAAGCCAAAATCCAAGACAAGG

AGGGCATCCCACCTGACCAGCAGCGGCTGATCTTCGCTGGCAAACAGCTG

GAGGATGGCCGCACTCTGTCAGATTATAATATCCAGAAAGAGTCCACCCT

GCACTTGGTGCTTCGTCTGCGAGGCGGC.
```

5. Pharmaceutical Compositions

The polypeptide antigens of the present invention can be used as active ingredients for the therapeutic treatment and/or prophylaxis of tick infestation. These therapeutic treatment and/or prophylactic agents can be administered to a subject (e.g., cattle) either in isolation or as compositions where they are mixed with pharmaceutically acceptable carriers, diluents, and/or adjuvants.

Depending on the specific conditions being treated, composition s for therapy and/or prophylaxis may be formulated and administered systemically or locally. Techniques for formulation and administration may be found in "Remington's Pharmaceutical Sciences," Mack Publishing Co., Easton, Pa., latest edition. Suitable routes may, for example, include intradermal injection. For injection, the therapeutic agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. Intramuscular and subcutaneous injection is appropriate, for example, for administration of immunogenic compositions, vaccines and DNA vaccines. In some specific embodiments, the pharmaceutical compositions are formulated for intradermal administration.

The pharmaceutical compositions of the invention can be formulated readily using pharmaceutically acceptable carriers well known in the art into dosages suitable for administration. Such carriers enable the compounds of the invention to be formulated in dosage forms such as tablets, pills, capsules, liquids, gels, syrups, slurries, suspensions and the like, for administration to the subject (e.g., cattle) to be treated. For example, a pharmaceutical composition formulated for oral ingestion will contain a suitable carrier, for example, selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical compositions suitable for use in the present invention include compositions wherein the active ingredients are contained in an effective amount to achieve its intended purpose. The dose of agent administered to a patient should be sufficient to elicit a beneficial response in the patient over time, such as a reduction in the symptoms associated with the condition. The quantity of the therapeutic/prophylactic agent(s) to be administered may depend on the subject to be treated inclusive of the age, sex, weight and general health condition thereof. In this regard, precise amounts of the therapeutic/prophylactic agent(s) for administration will depend on the judgement of the practitioner. In determining the effective amount of the agent to be administered in the treatment or prophylaxis of the condition, the physician may evaluate tissue levels of a polypeptide antigen, and progression of the disease or condition. In any event, those of skill in the art may readily determine suitable dosages of the therapeutic and/or prophylactic agents of the invention.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilisers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilising processes.

Dosage forms of the therapeutic agents of the invention may also include injecting or implanting controlled releasing devices designed specifically for this purpose or other forms of implants modified to act additionally in this fashion. Controlled release of an agent of the invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

Therapeutic agents of the invention may be provided as salts with pharmaceutically compatible counterions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

For any compound used in the method of the invention, the effective dose can be estimated initially from cell culture assays. For example, a dose can be formulated in animal models to achieve a circulating concentration range that includes the IC50 as determined in cell culture (e.g., the concentration of a test agent, which achieves a half-maximal reduction in target antigen). Such information can be used to more accurately determine useful doses in a mammal (e.g., cattle).

Dosage amount and interval may be adjusted individually to provide plasma levels of the active compound(s) which are sufficient to maintain target antigen-reducing effects or effects that ameliorate the disease or condition. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Alternately, one may administer the agent in a local rather than systemic manner, for example, via injection of the compound directly into a tissue, often in a depot or sustained release formulation. Furthermore, one may administer the agent in a targeted drug delivery system, for example, in a liposome coated with tissue-specific antibody. The liposomes will be targeted to and taken up selectively by the tissue.

From the foregoing, it will be appreciated that the agents of the invention may be used as therapeutic or prophylactic immunostimulating compositions or vaccines. Accordingly, the invention extends to the production of immunostimulating compositions containing as active compounds one or more of the therapeutic/prophylactic agents of the invention. Any suitable procedure is contemplated for producing such vaccines. Exemplary procedures include, for example, those described in NEW GENERATION VACCINES (1997, Levine et al., Marcel Dekker, Inc. New York, Basel Hong Kong).

Immunostimulating compositions according to the present invention can contain a physiologically acceptable diluent or excipient such as water, phosphate buffered saline and saline. They may also include an adjuvant as is well known in the art. Suitable adjuvants include, but are not limited to: surface active substances such as hexadecylamine, octadecylamine, octadecyl amino acid esters, lysolecithin, dimethyldioctadecylammonium bromide, N, N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS).

Suitably, antigen-presenting cells contacted ex vivo with the polypeptide antigens of the invention, as well as antigen-specific T lymphocytes generated with these antigen-presenting cells can be used as active compounds in immunostimulating compositions for prophylactic or therapeutic applications. The primed cells, which are preferably mature dendritic cells, can be injected with the tick polypeptide by any method that elicits an immune response into a syngeneic animal (i.e., a cow). Preferably, antigen-presenting cells are injected back into the same animal from whom the source tissue/cells was obtained. The injection site may be subcutaneous, intraperitoneal, intramuscular, intradermal, or intravenous. The number of antigen-primed antigen-presenting cells reinjected back into the animal in need of treatment may vary depending on inter alia, the antigen and size of the individual. This number may range for example between about $10^4$ and $10^8$, and more preferably between about $10^6$ and $10^7$ antigen-primed antigen-presenting cells (e.g., dendritic cells). The antigen-presenting cells should be administered in a pharmaceutically acceptable carrier, which is non-toxic to the cells and the individual. Such carrier may be the growth medium in which the antigen-presenting cells were grown, or any suitable buffering medium such as phosphate buffered saline.

In one embodiment, the antigen-primed antigen-presenting cells of the invention could also be used for generating large numbers of CD8+ or CD4+ CTL, for adoptive transfer to immunosuppressed individuals who are unable to mount normal immune responses. For example, antigen-specific CD8+ CTL can be adoptively transferred for therapeutic purposes in subjects afflicted with a tick infestation.

The effectiveness of the immunization may be assessed using any suitable technique. For example, CTL lysis assays may be employed using stimulated splenocytes or peripheral blood mononuclear cells (PBMC) on peptide coated or recombinant virus infected cells using $^{51}Cr$ labeled target cells. Such assays can be performed using for example any mammalian cells (Allen et al., 2000, J. Immunol. 164(9): 4968-4978; also Woodberry et al., infra). Alternatively, the efficacy of the immunization may be monitored using one or more techniques including, but not limited to, HLA class I tetramer staining—of both fresh and stimulated PBMCs (see for example Allen et al., supra), proliferation assays (Allen et al., supra), Elispot assays and intracellular cytokine staining (Allen et al., supra), Elisa assays for detecting linear B cell responses; and Western blots of cell sample expressing the synthetic polynucleotides. Particularly relevant will be the cytokine profile of T-cells activated by antigen, and more particularly the production and secretion of IFN-γ, IL-2, IL-4, IL-5, IL-10, TGF-β and TNF-α.

6. Antigen-Binding Molecules

The present invention also contemplates antigen-binding molecules that specifically bind to tick polypeptides of the present invention. Exemplary antigen-binding molecules for use in the practice of the present invention include monoclonal antibodies, Fv, Fab, Fab', and F(ab')$_2$ immunoglobulin fragments, as well as synthetic antibodies such as, but not limited to, single domain antibodies (DABs), synthetic stabilised Fv fragments (e.g., single chain Fv fragments (scFv), disulphide stabilized Fv fragments (dsFv), single variable region domains (dAbs), minibodies, combibodies, and multivalent antibodies such as diabodies and multi-scFv, or engineered equivalents. Techniques for preparing and using various antibody-based constructs and fragments are well known in the art. Means for preparing and characterising antibodies are also well known in the art. In illustrative examples, antibodies can be made by conventional immunization (e.g., polyclonal sera and hybridomas) with isolated, purified, or recombinant peptides or proteins corresponding to a tick polypeptide, or as recombinant fragments corresponding to a tick polypeptide, usually expressed in *Escherichia coli*, after selection from phage display or ribosome display libraries. Knowledge of the antigen-binding regions (e.g., complementarity-determining regions) of such antibodies can be used to prepare synthetic antibodies as described, for example, above.

Suitable monoclonal antibodies may be prepared by standard hybridoma methods, using differential binding assays to ensure that the antibodies are specific for a tick polypeptide, and do not show cross-reactivity. Alternatively, suitable monoclonal antibodies may be prepared using antibody engineering methods such as phage display. Methods for obtaining highly specific antibodies from antibody phage display libraries are known in the art, and several phage antibody libraries are commercially available from, for example MorphoSys (Martinsried, Germany), Cambridge Antibody Technology (Cambridge, UK), and Dyax (Cambridge, Mass.). Suitable phage display methods are described, for example, in U.S. Pat. Nos. 6,300,064 and 5,969,108, which are hereby incorporated by reference in their entirety. See also, for example, "*Antibody Engineering*," McCafferty et al.) Eds.)(IRL Press, 1996) and references therein. Phage display antibody methods can use libraries of antibodies in the Fab or scFv format. Once the antibody heavy and light chain genes are recovered from the phage antibodies, antibodies in any suitable format may be prepared (e.g., whole antibodies, Fab, scFv, etc.).

6.1 Single Chain Variable Region Molecules

Exemplary fragments of this type include single chain Fv fragments (sFv, frequently termed scFv) in which a peptide linker is used to bridge the N terminus or C terminus of a $V_H$ domain with the C terminus or N terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No. 4,946,778. However, in some cases a linker is absent. ScFvs may be prepared, for example, in accordance with methods outlined in Kreber et al. (1997, J. Immunol. Methods; 201(1): 35-55). Alternatively, they may be prepared by methods described in U.S. Pat. No. 5,091,513, European Patent No. 239,400, or the articles by Winter and Milstein (1991, Nature, 349: 293) and Plückthun et al. (1996, Antibody engineering: A practical approach. 203-252).

In another embodiment, the synthetic stabilized Fv fragment comprises a disulfide stabilized Fv (dsFv) in which cysteine residues are introduced into the $V_H$ and $V_L$ domains such that in the fully folded Fv molecule the two residues will form a disulfide bond therebetween. Suitable methods of producing dsFv are described for example in (Glockscuther et al. Biochem. 29: 1363-1367; Reiter et al. 1994, J. Biol. Chem. 269: 18327-18331; Reiter et al. 1994, Biochem. 33: 5451-5459; Reiter et al. 1994. Cancer Res. 54: 2714-2718; Webber et al. 1995, Mol. Immunol. 32: 249-258).

Also contemplated as antigen-binding molecules are single variable region domains (termed dAbs) as for example disclosed in Ward et al. (1989, Nature 341: 544-546); Hamers-Casterman et al. (1993, Nature. 363: 446-448); Davies & Riechmann, (1994, FEBS Lett. 339: 285-

290). Alternatively, the antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No. 5,837,821.

In an alternate embodiment, the antigen binding molecule may comprise non-immunoglobulin derived, protein frameworks. For example, reference may be made to Ku & Schultz, (1995, *Proc. Natl. Acad. Sci. USA*, 92: 652-6556) which discloses a four-helix bundle protein cytochrome b562 having two loops randomized to create complementarity determining regions (CDRs), which have been selected for antigen binding.

The antigen-binding molecule may be multivalent (i.e., having more than one antigen binding site). Such multivalent molecules may be specific for one or more antigens. Multivalent molecules of this type may be prepared by dimerisation of two antibody fragments through a cysteinyl-containing peptide as, for example disclosed by Adams et al., (1993, *Cancer Res.* 53: 4026-4034) and Cumber et al. (1992, *J. Immunol.* 149: 120-126). Alternatively, dimerisation may be facilitated by fusion of the antibody fragments to amphiphilic helices that naturally dimerise (Pack P. Plunckthun, 1992, *Biochem.* 31: 1579-1584), or by use of domains (such as the leucine zippers jun and fos) that preferentially heterodimerise (Kostelny et al., 1992, *J. Immunol.* 148: 1547-1553). In an alternate embodiment, the multivalent molecule may comprise a multivalent single chain antibody (multi-scFv) comprising at least two scFvs linked together by a peptide linker. In this regard, non-covalently or covalently linked scFv dimers termed "diabodies" may be used. Multi-scFvs may be bispecific or greater depending on the number of scFvs employed having different antigen binding specificities. Multi-scFvs may be prepared for example by methods disclosed in U.S. Pat. No. 5,892,020.

Phage display and combinatorial methods for generating natriuretic peptide antigen-binding molecules are known in the art (as described in, e.g., Ladner et al. U.S. Pat. No. 5,223,409; Kang et al. International Publication No. WO92/18619; Dower et al. International Publication No. WO91/17271; Winter et al. International Publication WO92/20791; Markland et al. International Publication No. WO 92/15679; Breitling et al.; International Publication WO 93/01288; McCafferty et al. International Publication No. WO92/01047; Garrard et al. International Publication No. WO 92/09690; Ladner et al. International Publication No. WO90/02809; Fuchs et al. (1991) *Biotechnology* 9: 1370-1372; Hay et al., 1992, *Hum Antibod Hybridomas* 3: 81-85; Huse et al., 1989, *Science* 246:1275-1281; Griffths et al., 1993, *EMBO J* 12: 725-734; Hawkins et al., 1992, *J Mol Biol* 226: 889-896; Clackson et al., 1991, *Nature* 352: 624-628; Gram et al., 1992, *Proc. Natl. Acad. Sci USA* 89: 3576-3580; Garrad et al., 1991, *Bio/Technology* 9: 1373-1377; Hoogenboom et al., 1991, *Nucleic Acid Res* 19: 4133-4137; and Barbas et al., 1991, *Proc. Natl. Acad. Sci USA* 88: 7978-7982).

The antigen-binding molecule can be coupled to a compound, e.g., a label such as a radioactive nucleus, or imaging agent, e.g., a radioactive, enzymatic, or other, e.g., imaging agent, e.g., a NMR contrast agent. Labels which produce detectable radioactive emissions or fluorescence are preferred.

7. Methods for Assessing Immunostimulation

An animal's capacity to respond to a tick infestation (i.e., tick polypeptides) may be assessed by evaluating whether immune cells primed to attack such antigens are increased in number, activity, and ability to detect and destroy those antigens. Strength of immune response is measured by standard tests including: direct measurement of peripheral blood lymphocytes (including B lymphocytes) by means known to the art; natural killer cell cytotoxicity assays (see, e.g., Provinciali M. et al. (1992, *J. Immunol. Meth.* 155: 19-24), cell proliferation assays (see, e.g., Vollenweider, I. and Groseurth, P. J. (1992, *J. Immunol. Meth.* 149: 133-135), immunoassays of immune cells and subsets (see, e.g., Loeffler, D. A., et al. (1992, *Cytom.* 13: 169-174); Rivoltini, L., et al. (1992, *Cancer Immunol. Immunother.* 34: 241-251); or skin tests for cell-mediated immunity (see, e.g., Chang, A. E. et al (1993, *Cancer Res.* 53: 1043-1050).

It will be appreciated that successful immunostimulation using a tick vaccine as described herein, can be assessed by counting the number of ticks present on an animal following vaccination. Ticks may be collected, and incubated to determine their egg-laying capacity and the viability of the eggs to emerge into larvae. (Exemplary methods for performing these sorts of assessment are outlined in more detail in the Examples, for example, by determining the effects of the vaccines on the total number of ticks (NET), weight of eggs (EW), and larval emergence (EC) etc, as described). In other words, the skilled person will appreciate that following the provision of an immune-stimulating composition as described herein, the success of the vaccination/immunostimulation is to be assessed by determining a) the formation of an immune response, such as antibody formation in the host, and b) the subsequent repulsion of ticks from feeding (i.e., reduced attachment, and development of ticks).

8. Pharmaceutical formulations

The compositions of the present invention are suitably pharmaceutical compositions. The pharmaceutical compositions often comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, etc. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

The pharmaceutical compositions may include various salts, excipients, delivery vehicles and/or auxiliary agents as are disclosed, e.g., in U.S. patent application Publication No. 2002/0019358, published Feb. 14, 2002.

Certain compositions of the present invention can further include one or more adjuvants before, after, or concurrently with the polynucleotide. The term "adjuvant" refers to any material having the ability to (1) alter or increase the immune response to a particular antigen or (2) increase or aid an effect of a pharmacological agent. It should be noted, with respect to polynucleotide vaccines, that an "adjuvant,"

can be a transfection facilitating material. Similarly, certain "transfection facilitating materials" described supra, may also be an "adjuvant." An adjuvant maybe used with a composition comprising a polynucleotide of the present invention. In a prime-boost regimen, as described herein, an adjuvant may be used with either the priming immunization, the booster immunization, or both. Suitable adjuvants include, but are not limited to, cytokines and growth factors; bacterial components (e.g., endotoxins, in particular superantigens, exotoxins and cell wall components); aluminium-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which may increase the expression, antigenicity or immunogenicity of the polypeptide is a potential adjuvant. The present invention provides an assay to screen for improved immune responses to potential adjuvants. Potential adjuvants which may be screened for their ability to enhance the immune response according to the present invention include, but are not limited to: Montanide, inert carriers, such as alum, bentonite, latex, and acrylic particles; PLURONIC block polymers, such as TITERMAX (block copolymer CRL-8941, squalene (a metabolizable oil) and a microparticulate silica stabilizer); depot formers, such as Freunds adjuvant, surface active materials, such as saponin, lysolecithin, retinal, Quil A, liposomes, and PLURONIC polymer formulations; macrophage stimulators, such as bacterial lipopolysaccharide; alternate pathway complement activators, such as insulin, zymosan, endotoxin, and levamisole; and non-ionic surfactants, such as poloxamers, poly (oxyethylene)-poly(oxypropylene) tri-block copolymers. Also included as adjuvants are transfection-facilitating materials, such as those described above.

The Montanide adjuvants are based on purified squalene and squalene, emulsified with highly purified mannide mono-oleate. There are several types of Montanide, including ISA 50V, 51, 206, and 720. ISA 50V, 51 and 720 are water-in-oil (W/O) emulsions, which ISA 206 is a W/O-in-water emulsion. ISA 206 and 50V have are used solely in veterinary vaccine formulations. Emulsions of Montanide ISA51 and 720 are composed of metabolizable squalene-based oil with a mannide mono-oleate emulsifier.

Poloxamers which may be screened for their ability to enhance the immune response according to the present invention include, but are not limited to, commercially available poloxamers such as PLURONIC surfactants, which are block copolymers of propylene oxide and ethylene oxide in which the propylene oxide block is sandwiched between two ethylene oxide blocks. Examples of PLURONIC surfactants include PLURONIC L121 poloxamer (ave. MW: 4400; approx. MW of hydrophobe, 3600; approx. wt % of hydrophile, 10%), PLURONIC L101 poloxamer (ave. MW: 3800; approx. MW of hydrophobe, 3000; approx. wt. % of hydrophile, 10%), PLURONIC L81 poloxamer (ave. MW: 2750; approx. MW of hydrophobe, 2400; approx. wt. % of hydrophile, 10%), PLURONIC L61 poloxamer (ave. MW: 2000; approx. MW of hydrophobe, 1800; approx. wt. % of hydrophile, 10%), PLURONIC L31 poloxamer (ave. MW: 1100; approx. MW of hydrophobe, 900; approx. wt. % of hydrophile, 10%), PLURONIC L122 poloxamer (ave. MW: 5000; approx. MW of hydrophobe, 3600; approx. wt. % of hydrophile, 20%), PLURONIC L92 poloxamer (ave. MW: 3650; approx. MW of hydrophobe, 2700; approx. wt. % of hydrophile, 20%), PLURONIC L72 poloxamer (ave. MW: 2750; approx. MW of hydrophobe, 2100; approx. wt. % of hydrophile, 20%), PLURONIC L62 poloxamer (ave. MW: 2500; approx. MW of hydrophobe, 1800; approx. wt. % of hydrophile, 20%), PLURONIC L42 poloxamer (ave. MW: 1630; approx. MW of hydrophobe, 1200; approx. wt. % of hydrophile, 20%), PLURONIC L63 poloxamer (ave. MW: 2650; approx. MW of hydrophobe, 1800; approx. wt. % of hydrophile, 30%), PLURONIC L43 poloxamer (ave. MW: 1850; approx. MW of hydrophobe, 1200; approx. wt. % of hydrophile, 30%), PLURONIC L64 poloxamer (ave. MW: 2900; approx. MW of hydrophobe, 1800; approx. wt. % of hydrophile, 40%), PLURONIC L44 poloxamer (ave. MW: 2200; approx. MW of hydrophobe, 1200; approx. wt. % of hydrophile, 40%), PLURONIC L35 poloxamer (ave. MW: 1900; approx. MW of hydrophobe, 900; approx. wt. % of hydrophile, 50%), PLURONIC P123 poloxamer (ave. MW: 5750; approx. MW of hydrophobe, 3600; approx. wt. % of hydrophile, 30%), PLURONIC P103 poloxamer (ave. MW: 4950; approx. MW of hydrophobe, 3000; approx. wt. % of hydrophile, 30%), PLURONIC P104 poloxamer (ave. MW: 5900; approx. MW of hydrophobe, 3000; approx. wt. % of hydrophile, 40%), PLURONIC P84 poloxamer (ave. MW: 4200; approx. MW of hydrophobe, 2400; approx. wt. % of hydrophile, 40%), PLURONIC P105 poloxamer (ave. MW: 6500; approx. MW of hydrophobe, 3000; approx. wt. % of hydrophile, 50%), PLURONIC P85 poloxamer (ave. MW: 4600; approx. MW of hydrophobe, 2400; approx. wt. % of hydrophile, 50%), PLURONIC P75 poloxamer (ave. MW: 4150; approx. MW of hydrophobe, 2100; approx. wt. % of hydrophile, 50%), PLURONIC P65 poloxamer (ave. MW: 3400; approx. MW of hydrophobe, 1800; approx. wt. % of hydrophile, 50%), PLURONIC F127 poloxamer (ave. MW: 12600; approx. MW of hydrophobe, 3600; approx. wt. % of hydrophile, 70%), PLURONIC F98 poloxamer (ave. MW: 13000; approx. MW of hydrophobe, 2700; approx. wt. % of hydrophile, 80%), PLURONIC F87 poloxamer (ave. MW: 7700; approx. MW of hydrophobe, 2400; approx. wt. % of hydrophile, 70%), PLURONIC F77 poloxamer (ave. MW: 6600; approx. MW of hydrophobe, 2100; approx. wt. % of hydrophile, 70%), PLURONIC F108 poloxamer (ave. MW: 14600; approx. MW of hydrophobe, 3000; approx. wt. % of hydrophile, 80%), PLURONIC F98 poloxamer (ave. MW: 13000; approx. MW of hydrophobe, 2700; approx. wt. % of hydrophile, 80%), PLURONIC F88 poloxamer (ave. MW: 11400; approx. MW of hydrophobe, 2400; approx. wt. % of hydrophile, 80%), PLURONIC F68 poloxamer (ave. MW: 8400; approx. MW of hydrophobe, 1800; approx. wt. % of hydrophile, 80%), PLURONIC F38 poloxamer (ave. MW: 4700; approx. MW of hydrophobe, 900; approx. wt. % of hydrophile, 80%).

Reverse poloxamers which may be screened for their ability to enhance the immune response according to the present invention include, but are not limited to PLURONIC R 31R1 reverse poloxamer (ave. MW: 3250; approx. MW of hydrophobe, 3100; approx. wt. % of hydrophile, 10%), PLURONIC R25R1 reverse poloxamer (ave. MW: 2700; approx. MW of hydrophobe, 2500; approx. wt. % of hydrophile, 10%), PLURONIC R 17R1 reverse poloxamer (ave. MW: 1900; approx. MW of hydrophobe, 1700; approx. wt. % of hydrophile, 10%), PLURONIC R 31R2 reverse poloxamer (ave. MW: 3300; approx. MW of hydrophobe, 3100; approx. wt. % of hydrophile, 20%), PLURONIC R 25R2 reverse poloxamer (ave. MW: 3100; approx. MW of hydrophobe, 2500; approx. wt. % of hydrophile, 20%), PLURONIC R 17R2 reverse poloxamer (ave. MW: 2150; approx. MW of hydrophobe, 1700; approx. wt. % of hydrophile, 20%), PLURONIC R 12R3 reverse poloxamer (ave.

MW: 1800; approx. MW of hydrophobe, 1200; approx. wt. % of hydrophile, 30%), PLURONIC R 31R4 reverse poloxamer (ave. MW: 4150; approx. MW of hydrophobe, 3100; approx. wt. % of hydrophile, 40%), PLURONIC R 25R4 reverse poloxamer (ave. MW: 3600; approx. MW of hydrophobe, 2500; approx. wt. % of hydrophile, 40%), PLURONIC R 22R4 reverse poloxamer (ave. MW: 3350; approx. MW of hydrophobe, 2200; approx. wt. % of hydrophile, 40%), PLURONIC R17R4 reverse poloxamer (ave. MW: 3650; approx. MW of hydrophobe, 1700; approx. wt. % of hydrophile, 40%), PLURONIC R 25R5 reverse poloxamer (ave. MW: 4320; approx. MW of hydrophobe, 2500; approx. wt. % of hydrophile, 50%), PLURONIC R10R5 reverse poloxamer (ave. MW: 1950; approx. MW of hydrophobe, 1000; approx. wt. % of hydrophile, 50%), PLURONIC R 25R8 reverse poloxamer (ave. MW: 8550; approx. MW of hydrophobe, 2500; approx. wt. % of hydrophile, 80%), PLURONIC R 17R8 reverse poloxamer (ave. MW: 7000; approx. MW of hydrophobe, 1700; approx. wt. % of hydrophile, 80%), and PLURONIC R 10R8 reverse poloxamer (ave. MW: 4550; approx. MW of hydrophobe, 1000; approx. wt. % of hydrophile, 80%).

Other commercially available poloxamers which may be screened for their ability to enhance the immune response according to the present invention include compounds that are block copolymer of polyethylene and polypropylene glycol such as SYNPERONIC L121 (ave. MW: 4400), SYNPERONIC L122 (ave. MW: 5000), SYNPERONIC P104 (ave. MW: 5850), SYNPERONIC P105 (ave. MW: 6500), SYNPERONIC P123 (ave. MW: 5750), SYNPERONIC P85 (ave. MW: 4600) and SYNPERONIC P94 (ave. MW: 4600), in which L indicates that the surfactants are liquids, P that they are pastes, the first digit is a measure of the molecular weight of the polypropylene portion of the surfactant and the last digit of the number, multiplied by 10, gives the percent ethylene oxide content of the surfactant; and compounds that are nonylphenyl polyethylene glycol such as SYNPERONIC NP10 (nonylphenol ethoxylated surfactant-10% solution), SYNPERONIC NP30 (condensate of 1 mole of nonylphenol with 30 moles of ethylene oxide) and SYNPERONIC NP5 (condensate of 1 mole of nonylphenol with 5.5 moles of naphthalene oxide).

Other poloxamers which may be screened for their ability to enhance the immune response according to the present invention include: (a) a polyether block copolymer comprising an A-type segment and a B-type segment, wherein the A-type segment comprises a linear polymeric segment of relatively hydrophilic character, the repeating units of which contribute an average Hansch-Leo fragmental constant of about −0.4 or less and have molecular weight contributions between about 30 and about 500, wherein the B-type segment comprises a linear polymeric segment of relatively hydrophobic character, the repeating units of which contribute an average Hansch-Leo fragmental constant of about −0.4 or more and have molecular weight contributions between about 30 and about 500, wherein at least about 80% of the linkages joining the repeating units for each of the polymeric segments comprise an ether linkage; (b) a block copolymer having a polyether segment and a polycation segment, wherein the polyether segment comprises at least an A-type block, and the polycation segment comprises a plurality of cationic repeating units; and (c) a polyether-polycation copolymer comprising a polymer, a polyether segment and a polycationic segment comprising a plurality of cationic repeating units of formula —NH—R0, wherein R0 is a straight chain aliphatic group of 2 to 6 carbon atoms, which may be substituted, wherein said polyether segments comprise at least one of an A-type of B-type segment. See U.S. Pat. No. 5,656,611. Other poloxamers of interest include CRL1005 (12 kDa, 5% POE), CRL8300 (11 kDa, 5% POE), CRL2690 (12 kDa, 10% POE), CRL4505 (15 kDa, 5% POE) and CRL1415 (9 kDa, 10% POE).

Other auxiliary agents which may be screened for their ability to enhance the immune response according to the present invention include, but are not limited to, Acacia (gum arabic); the poloxyethylene ether R—O—(C2H4O)x-H (BRIJ), e.g., polyethylene glycol dodecyl ether (BRIJ 35, x=23), polyethylene glycol dodecyl ether (BRIJ 30, x=4), polyethylene glycol hexadecyl ether (BRIJ 52 x=2), polyethylene glycol hexadecyl ether (BRIJ 56, x=10), polyethylene glycol hexadecyl ether (BRIJ 58P, x=20), polyethylene glycol octadecyl ether (BRIJ 72, x=2), polyethylene glycol octadecyl ether (BRIJ 76, x=10), polyethylene glycol octadecyl ether (BRIJ® 78P, x=20), polyethylene glycol oleyl ether (BRIJ 92V, x=2), and polyoxyl 10 oleyl ether (BRIJ 97, x=10); poly-D-glucosamine (chitosan); chlorbutanol; cholesterol; diethanolamine; digitonin; dimethylsulfoxide (DMSO), ethylenediamine tetraacetic acid (EDTA); glyceryl monosterate; lanolin alcohols; mono- and di-glycerides; monoethanolamine; nonylphenol polyoxyethylene ether (NP-40); octylphenoxypolyethoxyethanol (NONIDET NP-40 from Amresco); ethyl phenol poly (ethylene glycol ether)n, n=11 (NONIDET P40 from Roche); octyl phenol ethylene oxide condensate with about 9 ethylene oxide units (NONIDET P40); IGEPAL CA 630 ((octyl phenoxy) polyethoxyethanol; structurally same as NONIDET NP-40); oleic acid; oleyl alcohol; polyethylene glycol 8000; polyoxyl 20 cetostearyl ether; polyoxyl 35 castor oil; polyoxyl 40 hydrogenated castor oil; polyoxyl 40 stearate; polyoxyethylene sorbitan monolaurate (polysorbate 20, or TWEEN-20; polyoxyethylene sorbitan monooleate (polysorbate 80, or TWEEN-80); propylene glycol diacetate; propylene glycol monstearate; protamine sulfate; proteolytic enzymes; sodium dodecyl sulfate (SDS); sodium monolaurate; sodium stearate; sorbitan derivatives (SPAN), e.g., sorbitan monopalmitate (SPAN 40), sorbitan monostearate (SPAN 60), sorbitan tristearate (SPAN 65), sorbitan monooleate (SPAN 80), and sorbitan trioleate (SPAN 85); 2,6,10,15,19,23-hexamethyl-2,6,10,14,18,22-tetracosahexaene (squalene); stachyose; stearic acid; sucrose; surfactin (lipopeptide antibiotic from *Bacillus subtilis*); dodecylpoly(ethyleneglycolether)9 (THESIT) MW 582.9; octyl phenol ethylene oxide condensate with about 9-10 ethylene oxide units (TRITON X-100); octyl phenol ethylene oxide condensate with about 7-8 ethylene oxide units (TRITON X-114); tris(2-hydroxyethyl)amine (trolamine); and emulsifying wax.

In certain adjuvant compositions, the adjuvant is a cytokine. A composition of the present invention can comprise one or more cytokines, chemokines, or compounds that induce the production of cytokines and chemokines, or a polynucleotide encoding one or more cytokines, chemokines, or compounds that induce the production of cytokines and chemokines. Examples include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNΩ), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and M3P-1 beta), Leishmania elongation initiating factor (LEIF), and Flt-3 ligand.

In certain compositions of the present invention, the polynucleotide construct may be complexed with an adjuvant composition comprising (±)—N-(3-aminopropyl)-N,N-dimethyl-2,3-bis(syn-9-tetradeceneyloxy)-1-propan-aminium bromide (GAP-DMORIE). The composition may also comprise one or more co-lipids, e.g., 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). An adjuvant composition comprising GAP-DMORIE and DPyPE at a 1:1 molar ratio is referred to herein as VAXFECTIN adjuvant. See, e.g., PCT Publication No. WO 00/57917.

In other embodiments, the polynucleotide itself may function as an adjuvant as is the case when the polynucleotides of the invention are derived, in whole or in part, from bacterial DNA. Bacterial DNA containing motifs of unmethylated CpG-dinucleotides (CpG-DNA) triggers innate immune cells in vertebrates through a pattern recognition receptor (including toll receptors such as TLR 9) and thus possesses potent immunostimulatory effects on macrophages, dendritic cells and B-lymphocytes. See, e.g., Wagner, H., Curr. Opin. Microbiol. 5:62-69 (2002); Jung, J. et al., J. Immunol. 169: 2368-73 (2002); see also Klinman, D. M. et al., Proc. Natl Acad. Sci. U.S.A. 93:2879-83 (1996). Methods of using unmethylated CpG-dinucleotides as adjuvants are described in, for example, U.S. Pat. Nos. 6,207,646, 6,406,705 and 6,429,199.

The ability of an adjuvant to increase the immune response to an antigen is typically manifested by a significant increase in immune-mediated protection. For example, an increase in humoral immunity is typically manifested by a significant increase in the titre of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Nucleic acid molecules and/or polynucleotides of the present invention, e.g., plasmid DNA, mRNA, linear DNA or oligonucleotides, may be solubilized in any of various buffers. Suitable buffers include, for example, phosphate buffered saline (PBS), normal saline, Tris buffer, and sodium phosphate (e.g., 150 mM sodium phosphate). Insoluble polynucleotides may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art. For aqueous compositions used in vivo, sterile pyrogen-free water can be used. Such formulations will contain an effective amount of a polynucleotide together with a suitable amount of an aqueous solution in order to prepare pharmaceutically acceptable compositions suitable for administration to a mammal (e.g., cattle).

Compositions of the present invention can be formulated according to known methods. Suitable preparation methods are described, for example, in Remington's Pharmaceutical Sciences, 16th Edition, A. Osol, ed., Mack Publishing Co., Easton, Pa. (1980), and Remington's Pharmaceutical Sciences, 19th Edition, A. R. Gennaro, ed., Mack Publishing Co., Easton, Pa. (1995). Although the composition may be administered as an aqueous solution, it can also be formulated as an emulsion, gel, solution, suspension, lyophilized form, or any other form known in the art. In addition, the composition may contain pharmaceutically acceptable additives including, for example, diluents, binders, stabilizers, and preservatives.

The following examples are included for purposes of illustration only and are not intended to limit the scope of the present invention, which is defined by the appended claims.

8.1 Dosage

The present invention is generally concerned with therapeutic and prophylactic compositions. The compositions will comprise an "effective amount" of the compositions defined herein, such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, an "effective amount" will fall in a relatively broad range that can be determined through routine trials.

Dosage treatment may be a single dose schedule or a multiple dose schedule. In some embodiments, a dose of between around 50 μg to around 5 mg or above is sufficient to induce an immune response to the composition. More specifically, a dose of between around 100 μg to around 1 mg may be used in the methods of the invention. Thus, the methods of the present invention include dosages of the compositions defined herein of around 50 μg, 100 μg, 150 μg, 200 μg, 250 μg, 300 μg, 350 μg, 400 μg, 450 μg, 500 μg, 600 μg, 650 μg, 700 μg, 750 μg, 800 μg, 850 μg, 900 μg, 950 μg, 1 mg, or more, in order to treat a tick infestation.

The compositions of the present invention can be suitably formulated for injection. The composition may be prepared in unit dosage form in ampules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tissues or lungs.

In preferred protocols, a formulation comprising the naked polynucleotide in an aqueous carrier is injected into tissue in amounts of from 10 µl per site to about 1 ml per site. The concentration of polynucleotide in the formulation is from about 0.1 µg/ml to about 20 mg/ml.

Once formulated, the compositions of the invention can be administered directly to the subject (e.g., as described above), for example, intradermally, intravenously, subcutaneously, orally, or other conventional methods for providing immune-stimulating compositions to an individual in need.

The compositions of the invention may be used for stimulating an immune response to a tick polypeptide in a subject that is immunologically naïve to the tick polypeptide or that has previously raised an immune response to that tick polypeptide. Thus, the present invention extends to methods for enhancing an immune response in a subject by administering to the subject the compositions or vaccines of the invention. Desirably, the immune response is both a cell-mediated immune response (e.g., a B-cell mediated response, which desirably includes $CD4^+$ T helper cells) and a humoral immune response (e.g., an antibody response).

Also encapsulated by the present invention is a method for treatment and/or prophylaxis of a tick infestation, comprising administering to a patient in need of such treatment an effective amount of a at least one polypeptide antigen that corresponds to a tick polypeptide, or a polynucleotide from which the polypeptide antigen is expressible, wherein the at least one tick polypeptide is selected from TC12130, MPAAN50tr, MPAA730tr, TC12142, TC10097, TC9753, TC13011, TC8992, and TC5995.

In yet another aspect, the invention provides a method for reducing the risk of transmission of a tick in a subject comprising administering to the subject an effective amount of a at least one polypeptide antigen that corresponds to a tick polypeptide, or a polynucleotide from which the polypeptide antigen is expressible, wherein the at least one tick polypeptide is selected from TC12130, MPAAN50tr, MPAA730tr, TC12142, TC10097, TC9753, TC13011, TC8992, and TC5995, as described above and elsewhere herein.

Ticks are vectors of a number of diseases and disorders, some of which can be debilitating or life-threatening. Exemplary pathogens transmitted by ticks include, but are not limited to, *Anaplasma* spp. (e.g., *Anaplasma marginale*), *Babesia* spp. (e.g., *B. bovis* and *B. bigemina*), *Borrelia* spp., *Theileria* spp. (e.g., *T. parva*) and viruses within the tick-borne encephalitis complex. Accordingly, the pathogen can cause a disease or disorder in the subject including, but not limited to cattle tick fever, East Coast Fever, babesiosis, tick-borne Encephalitis, anaplasmosis, or Lyme Disease. Thus, the invention also provides a method for the prevention of cattle tick fever, East Coast Fever, babesiosis, tick-borne Encephalitis, anaplasmosis, or Lyme Disease in a subject, the method comprising administering to the subject an effective amount of a at least one polypeptide antigen that corresponds to a tick polypeptide, or a polynucleotide from which the polypeptide antigen is expressible, wherein the at least one tick polypeptide is selected from TC12130, MPAAN50tr, MPAA730tr, TC12142, TC10097, TC9753, TC13011, TC8992, and TC5995, as described above and elsewhere herein, and thereby preventing cattle tick fever, East Coast Fever, babesiosis, tick-borne Encephalitis, anaplasmosis, or Lyme Disease in the subject.

After a subject is determined to be at risk of cattle tick fever, East Coast Fever, babesiosis, tick-borne Encephalitis, anaplasmosis, or Lyme Disease, it may be desirable to treat the subject with a therapeutic or prophylactic agent for the treatment of these diseases. Doxycycline, Amoxicillin, or Atovaquone plus Azithromycin are some examples of suitable treatments.

In some embodiments, the immunostimulatory composition is administered to a subject on a monthly basis. Alternatively, the immunostimulatory composition is administered 1, 2, 3, 4, 5, 6, 7, 8, 9, 10, 11 or more times a year.

In some embodiments, the composition comprises a nucleic acid construct from which a polypeptide antigen as described above is expressible. Administration of such nucleic acid constructs to a mammal (for example, cattle), may include delivery via direct oral intake, systemic injection, or delivery to selected tissue(s) or cells. Delivery of the nucleic acid constructs to cells or tissues of the mammal may be facilitated by microprojectile bombardment, liposome mediated transfection (e.g., Lipofectin or Lipofectamine), electroporation, calcium phosphate or DEAE-dextran-mediated transfection, for example. A detailed discussion of suitable delivery methods may be found in Chapter 9 of Ausubel et al., (1994-1998, supra). For example, in some embodiments the nucleic acid constructs are administered through intradermal injection.

The step of introducing the expression vector into the selected target cell or tissue will differ depending on the intended use and species, and can involve one or more of non-viral and viral vectors, cationic liposomes, retroviruses, and adenoviruses such as, for example, described in Mulligan, R. C., (1993). Such methods are well known to the skilled person.

Prime-Boost Regimens

The methods of the invention may comprise (i) administering a priming composition of at least one polypeptide antigen or a polynucleotide sequence from which a nucleotide sequence encoding at least one polypeptide antigen is expressible, wherein the polypeptide antigens are those described above and elsewhere herein, and (ii) subsequently administering a later booster composition of at least one polypeptide antigen or a polynucleotide sequence from which a nucleotide sequence encoding a at least one polypeptide antigen is expressible.

For example, the booster composition may be administered at least 7, 14, 21 or 28 days, at least 1, 2, 3, 4, 5, or 6 months, or at least 1, 2, 3, 4, or 5 years after the priming composition. The priming and booster compositions may be administered by the same route or they may be administered via different routes. For example, the priming and booster doses may both be administered intradermally. One advantage of intradermal administration for DNA vaccines is that this route has a higher frequency of dendritic cells and other antigen presenting cells than some other routes (e.g., the intramuscular route). As the efficacy of administration is at least partially dependent on uptake, processing and presentation of the immunogen by dendritic cells, which may be enhanced by administering through this route.

The booster composition may be administered one or several times at the same or different dosages. It is within the ability of one of ordinary skill in the art to optimize prime-boost combinations, including optimization of the timing and dose of administration.

9. Methods of Treatment

Also encapsulated by the present invention is a method for treatment and/or prophylaxis of a tick infestation, comprising administering to a mammal (e.g., cattle) in need of such treatment an effective amount of a composition as broadly described above and elsewhere herein.

In one embodiment, the cell or composition of the invention can also be used for generating large numbers of $CD4^+$ CTL. For example, antigen-specific $CD4^+$ CTL can be adoptively transferred for therapeutic purposes in mammals (e.g., cattle) afflicted with a tick infestation.

In accordance with the present invention, it is proposed that cells and compositions that include one or more polypeptide antigens that correspond to at least a portion of a tick polypeptide find utility in the treatment or prophylaxis of a tick infestation. The compositions of the present invention may be used therapeutically after a tick infestation is diagnosed, or may be used prophylactically before the mammal carries a tick.

When the compositions described above and elsewhere herein are used in prophylactic methods against tick infestations, such methods are suitably prime-boost vaccinations against a tick polypeptide that induce long-lasting humoral, cell-mediated and mucosal immune responses against the tick polypeptide.

In some embodiments the cells and compositions of the present invention are administered in multiple doses in a prime-boost regimen, with the goal of inducing long-lived potent immunity against a tick polypeptide. Such strategies use a second dose of the composition to bolster immunity elicited by the priming dose.

Some embodiments of the present invention are based on the realisation that an optimal strategy for eliciting therapeutic and protective immunity against a tick polypeptide involves the generation of both a cellular and a humoral immune response to the tick polypeptide. The invention thus provides a multi-component administration strategy in which a first dose of the composition of the present invention primes the immune system by eliciting or inducing a first immune response, and a second dose of the composition of the present invention is used to boost or elicit a second immune response, wherein the composition administered in the first dose is the same as that administered second dose. In illustrative examples of this type, the first dose is administered to induce largely a cellular immune response to the target antigen, whereas the second dose is administered largely to elicit a humoral immune response to the target antigen. Upon completion of the administration steps of the strategy, both cellular and humoral immune responses develop to the target antigen. The two responses together thus provide effective or enhanced protection against a tick infestation or disease and/or condition that is transmitted by or otherwise associated with a tick.

In order to maximize the direct stimulation and activation of those $CD4^+$ CTLs that target the relevant tick polypeptide(s), the compositions used for the prime administration and the boost administration are, preferentially, the same.

10. Kits

The present invention also provides kits comprising an immunostimulatory composition as broadly described above and elsewhere herein. Such kits may additionally comprise alternative immunogenic agents for concurrent use with the immunostimulatory compositions of the invention.

In some embodiments, in addition to the immunostimulatory compositions of the present invention the kits may include suitable components for performing the prime-boost regimens described above. For example, the kit may include separately housed priming and boosting doses of the at least one polypeptide antigens.

The kits may comprise additional components to assist in performing the methods of the present invention such as, for example, administration device(s), buffer(s), and/or diluent(s). The kits may also include containers for housing the various components and instructions for using the kit components in the methods of the present invention.

In order that the invention may be readily understood and put into practical effect, particular preferred embodiments will now be described by way of the following non-limiting examples.

EXAMPLES

Example 1: Antigen Discovery

In an effort to discover immunogenic polypeptide sequences that dictate the immune response of a tick-resistant animal (and therefore be used as a therapeutic and prophylactic treatment against tick infestation), a "reverse vaccinology" strategy was undertaken (as outlined in FIG. 1). In brief, this approach utilizes computer software to screen tick sequences to identify vaccine candidates which are then systematically evaluated in laboratory models. And positively identified sequences are then entered into 'proof of concept' trials in cattle.

Materials and Methods

The BmiG2 database comprising 13,643 ESTs was searched for sequences that aligned with the Pfam terms (using the methods taught in Bateman et al., 2002 *Nucleic Acids Res.* 30: 276-280) "extracellular", "membrane", "secreted" and "antigen". A separate microarray experiment using a custom made array based on the BmiG2 EST database was used to select genes expressed by ticks (frustrated larvae in a mesh bag and adult feeding females) on tick resistant cattle, as described in Rodriguez-Valle et al. 2010. The selected sequences were further analysed to annotate the putative candidates using signal peptides, transmembrane domains, metabolic pathways/KEGG, and Gene Ontology ("GO") terms. The final group was subsequently categorized into groups corresponding to sequence similarity levels. The candidates were further analysed for high bovine homology. Subsequently, the final list was further categorized by Blastx sequence analyses against the following datasets: NCBI, COG (Tatusov et al., 2003 *BMC Bioinformatics* 4:41), String (von Mering et al., 2006 *Nucleic Acids Res* 35:D358-362), The Kyoto Encyclopedia of Genes and Genomes (KEGG) (Okuda et al., 2008 *Nucleic Acids Res* 36: W423-6), *R. microplus* Gene Index (Guerrero et al. 2005 *Insect Biochem Mol Biol.* 35:585-95; Wang et al. 2007 *BMC Genomics* 8: 368-382), NCBI conserved domain database (CDD) (Marchler-Bauer et al., 2009 *Nucleic Acids Res* 37:D205-10), and non-redundant protein database (nr) using Murdoch University's Centre for Comparative Genomics (CCG) HPC resource. Trans-membrane domain searches were conducted using S-TMHMM (Krogh et al., 2001 *J. Mol. Biol.* 305:567-80) and protein localization using SignalP (Bendtsen et al., 2004 *J Mol Biol.* 340: 783-95) to reconfirm earlier analyses. All analysis results were extracted and merged using Bioperl (Stajich et al., 2002 *Genome Res* 12:1611-1618) and Emboss tools (Rice et al., 2000 Trends Genet 16: 267-277).

Results

TABLE 10

| Pham Bioinformatics analysis of sequences from USDA database | No. of proteins | Sign. bovine protein similarity | Potential candidates |
| --- | --- | --- | --- |
| High probability e-100 | 19 | 5 | 14 |
| Med-high probability e-50 | 46 | 18 | 28 |
| Low probability e-10 | 25 | 0 | 25 |
| No known protein similarity | 47 | 0 | 47 |
| TOTAL | 137 | 30 | 107 |

A final list of 107 candidates was confirmed and a further 195 candidates were manually selected from a tick microarray gene expression study (Rodriguez Valle et al 2010) from ticks which were sensing or feeding on Brahman (tick resistant breed of cattle), increasing the final candidate list to 302 ESTs. See FIG. 1 (gene discovery phase of the reverse vaccinology pipeline).

Example 2 qRT-PCR Localization Analysis, Domain Clustering, B Cell & T Cell Predictions and Screening Methods & Materials
qRT-PCR Analysis
The (281 of 302) vaccine candidates were analysed by qRT-PCR to "localise" ESTs. Methods for qRT-PCR were as described previously (see, Lew-Tabor et al, *Vet Parasitol*, 2010).

B Cell Epitope Predictions and ELISA Screening
In an effort to identify B-cell epitopes, peptides with minimum length of 10 amino acids were selected using Bepipred (Larsen et al., 2006 *Immunome Res* 2:2) at a threshold greater than 0.35. This resulted in the production 716 synthetic biotinylated peptides (Mimotopes Pty Ltd) targeting 198 proteins (of the 209 total) which were screened in an ELISA format.

Peptides were dissolved in 1 mL of 40% Acetonitrile/Water solution, or if acetonitrile is unavailable, using pure water and 10 µl of dissolved peptide was mixed with 990 µL of PBS/TWEEN-20. The biotinylated peptide solutions are then used without further dilution for capture onto the coated streptavidin or avidin plates. After peptide capture, the general assay procedure recommended by Mimotope was followed, sera collected from susceptible and resistant cattle (source of cattle, see Piper et al. 2017) were pooled and diluted 1/10 to be added into each well. Negative control was pooled sera from tick naïve cattle. Rabbit IgG Anti Cow conjugate was diluted 1/4000 Negative and positive peptides were provided by Mimotope as internal controls of the assay. A peptide was considered positive with an average of 1.5 D.O 450 nm higher than the negative control.

T Helper Epitope Predictions and Peptide Screening (Lymphocyte Proliferation Assays)
In an effort to identify T helper cell epitopes (HLA), sequences with a strong ligation strength to a defined HLA type for a sequence of amino acids MHCII (High binding affinity) HLA-DRB1-010, HLA_DRB1-0301 were identified (Sturniolo et al., 1999 *Nat. Biotechnol.* 17: 555-61). IC50 values<50 nM are considered to have a high affinity. 202 peptides for 128 proteins (of the 248) were subsequently designed and synthesized (Mimotopes Pty Ltd) for lymphocyte proliferation studies.

Blood was collected from three Holstein-Friesian cattle that were grazing at Pinjarra Hills farm, University of Queensland. Cattle were exposed to natural tick infestation for a long period. PBMC were isolated from bovine blood using a Ficoll-Histopaque gradient (Amersham, Piscataway, N.J., USA). PBMC were counted and plated into 96-well plates at $5\times10^5$ cells/well in RPMI-1640 plus 10% foetal calf serum. Cells are cultured in the presence of the each T cell epitope at 37° C., 5% $CO_2$ per 5 days. BrdU labelling solution is added to each well (final concentration: 10 mM BrdU) and cells are re-incubated for an additional 18 h at 37° C. The cell proliferation ELISA, BrdU (colorimetric) kit (ROCHE) was used to complete this assay as per manufacturer's instructions.

Results
qRT-PCR Analysis
Twenty-one of the candidates could not be amplified, and therefore no further analysis was continued with these ESTs. Vaccine candidates were selected for further analysis based on the localisation (qRT-PCR results), and subsequent ESTs selected were those localising to ticks on resistant cattle and those localising to multiple tick organs and or stages. Those ESTs with no ORF, limited localisation and bioinformatically predicted as non-secretory/inner membrane candidates—were deleted. This was a manual edit following collation of qRT-PCR data with SignalP and membrane predictions (see the base of FIG. 1), and when the size of the EST was <100 bp in length. A list of 209 ESTs resulted from the above analyses and manual deletions.

B-Cell Epitope Screening
A total of 55 EST proteins were recognised by sera from susceptible cattle while a further 69 ESTs were recognised by resistant sera or susceptible and resistant sera. Only those peptides recognised by resistant cattle were selected for subsequent analyses as it was hypothesized that peptides recognised by sera collected from resistant cattle only could be "protective". The remaining ESTs either without B cell epitope predictions or with no recognition by sera or recognition by susceptible cattle sera only were deleted. A total seventy-six peptides (with the strongest ELISA results, 7 ESTs with 2 peptides were tested separately) were selected for antibody production for in vitro feeding experiments.

Figure 2:
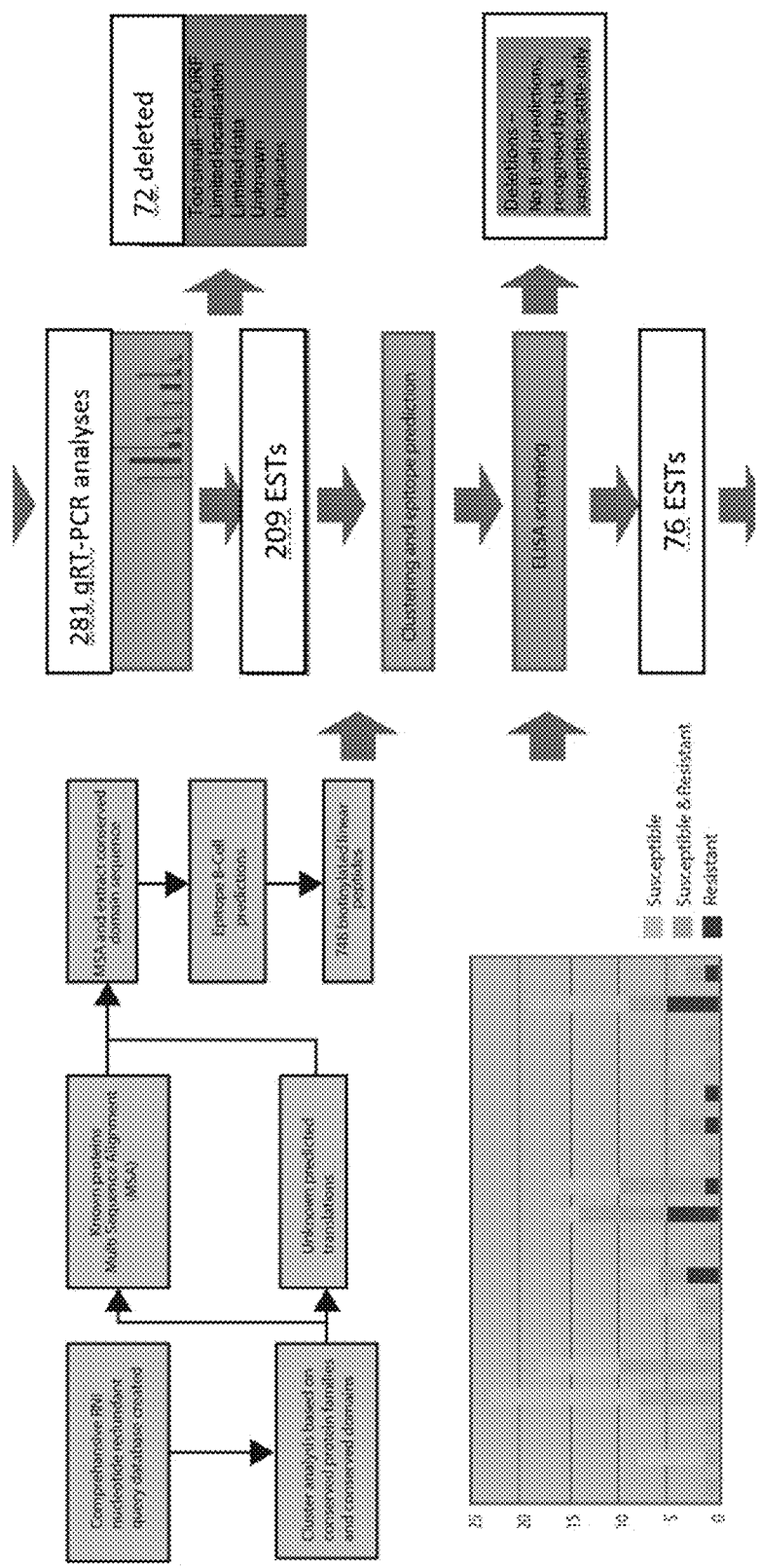

FIG. 2 summarises the B cell epitope EST clustering and predictions and a summary of the ELISA results resulting in the selection of final the final 76 peptides.

T-Cell Helper Epitope Identification
Twenty-four out of the 202 peptides demonstrated consistent lymphocyte stimulation from all three cattle samples. Three with very strong lymphocyte proliferation results for use in recombinant constructs include: chitin binding domain proteins: TC13324 and TC5967; and an Immunoglobulin G binding protein A: TC12173. TC13011 was also selected as it had a strong B cell epitope in addition to an active T helper epitope.

Example 3: Tick Feeding Experiments

Methods and Materials

Antibodies to ~76 peptides were produced using sheep inoculated with conjugated peptides through Mimotopes Pty Ltd and the serum supplied was used for the subsequent tick feeding experiments.

The capillary feeding method was adapted from standard methods described previously (see, Lew-Tabor et al, 2014). Tube feeding was set up immediately following tick collection (tick colony at QASP) using ~19/20 day old semi-engorged females. Ten ticks per treatment including serum control (no anti-tick antibodies) with approximately 6-7 treatments were set up per tick feeding experiment (including controls). Ticks were each microscopically examined for 'intact' mouthparts, pre-weighed prior to artificial feeding, followed by positioning of tubes and overnight feeding. Following successful feeding, ticks were weighed and placed in individual tubes to monitor egg output (3 weeks). Final egg weight was determined per treatment and eggs were left to hatch to determine % larval emergence (2-3 weeks). Serum from a TickGARD vaccinated animal (Bm86) was used as a control positive treatment for antibody feeding in sheep serum and dsRNA from TC6372 was used as the control for gene knockdown feeding experiments in bovine serum.

Efficacy (%) of a particular antibody treatment was calculated as a simple ratio of the average measurement between treated (t) and control (c) ticks:

$$\text{Efficacy (\%)} = 100 \times \left[ 1 - \left( \frac{acet}{acec} \right) \left( \frac{apeht}{apehc} \right) \right]$$

'ace' is the average of the cumulative egg output per tick and 'apeh' is the average of the percentage of eggs hatching into larvae (Lew-Tabor et al 2014).

Effectivity of a particular antibody treatment was calculated relative to the control treatments as described in the equation above. Although mouth parts were microscopically examined, there were a small percentage of ticks which still did not feed in all treatments and controls. In control treatments, 2-3 ticks (out of 10) would sometimes not feed and in some instances with some treatments very few ticks feed. To determine if the latter was an effect of the actual treatment these were repeated (at least twice) to increase the validity of the observation and to determine if the failure to feed was indeed due to the antibody treatment. Effectivity is a measure of average weight, egg output and larval emergence relative to the control fed ticks.

Results

A summary of antibody treatment effectivities is presented in Table 11.

TABLE 11

| Effectivity range of treatment | Number of tick antigen peptide antisera (n = 76) | Peptide source sequence ID (some targets with more than one antibody) |
|---|---|---|
| 90-100% | 8 | MPAAN50TR, TC10097, TC12130, TC12142, TC13011, TC14222, TC9093, TC7158-1. |
| ~70-90% | 14 | MPAA730tr, MPOAC55tr-2, TC18188, TC12173, TC12478, TC12710, TC12725, TC5995-1, TC5995-2, TC6125, TC7158-2, TC7399, TC8992, TC8946-1 |
| 50-~70% | 17 | *Bm86 (TickGARD), CK174565, CK174651, TC12089, TC12256, TC12264, TC12460, TC12661, TC12682, TC13140, TC14453, TC14491, TC6577-1, TC6945, TC8850, TC9596, TC9563 |
| 30-50% | 16 | CK177328, CK180459, MPAA644tr, MPAAF66tr, MPOAD40tr, TC11485, TC12010, TC12106, TC13841-1, TC5943, TC6926, TC8213, TC8946-2, TC9416, MPOAC55tr-1, TC5802-1 |
| 0-30% | 21 | CK173007, CK177859, CK182641/TC18188, CV442500, CV448736, TC10057, TC12175, TC12425, TC14653, TC5802-2, TC6832, TC8000, TC5962, TC9454, TC9528, TC9597, TC13841-2, TC6577-2, TC9278, TC9363, TC9407 |

*whole anti-protein serum, all other treatments are anti-peptide;
@ a peptide sequence which targeted conserved regions of R. appendiculatus and R. microplus histamine binding protein-2 was included in this study;
candidates which are underlined indicate a statistically significant result.

The effectivity values in Table 12 are approximate ranges based on the observation that treatments with a high rate of effect (90-100%) typically result in nil to minimal egg laying. The 70-90% range usually indicates that egg laying and larval emergence was greatly reduced. Strikingly, the range for the Bm86 serum was lower at the 30-59% effectivity and we have identified treatments which were similar in effectivity. These have reduced egg laying and % larval hatch rates. The stronger treatments (~70-100%) were repeated to confirm results in this high range (20-40 ticks per treatment). Statistical analyses validated the observations particularly at >70% effectivity levels. It is important to note that the antibodies were produced against antigen peptides only and not to whole corresponding proteins. The Bm86 treatment represents antibodies from animals vaccinated with TICKGARD (Bm86 "whole" recombinant protein) and this treatment ranged in several experiments between 45-71% effectivity (i.e., 25-40% reduction in egg laying compared to control sera fed ticks). Antibodies with effectivity values ranging from 0-50% were variable and demonstrated nil to low impact on egg output and larval emergence due to treatment.

Table 12 provides a summary of the efficacy of antibodies raised to specific peptides, along with observations of the tick status in response to such antibody treatments.

TABLE 12

| Peptide | Antibody adult tick-feeding effectivity | Tick effects |
|---|---|---|
| TC12130 | 96% | 50-67% effect on feeding and egg development |
| MPAAN50tr | 90-92% | 55-78% effect on feeding and egg development |
| TC12142 | 93% | 13-100% effect on feeding and egg development |
| TC10097 | 87-91% | 40-60% effect on feeding and egg development |
| TC9753 | 22-63% | 29-44% effect on feeding and egg development |
| TC13011 | 48-92% | 44-67% effect on feeding and egg development |
| TC8992 | 64-85% | 33-50% effect on feeding and egg development |
| TC5995 | 83-92% | 40-60% effect on feeding and egg development |

Example 4: Preliminary Cattle Trials

Two trials were undertaken using mixtures of peptides:
1. Trial 1: A mixture of 6 peptides from the top 90-100% from in vitro feeding were testing in trial undertaken in EMBRAPA Brazil, achieving 73% efficacy which included: TC14222, TC12130, TC7158 and MPAAN50tr.
2. Trial 2: A mixture of 32 peptides were produced in a single construct and expressed in *Pichia pastoris*, these included all hypothetical proteins which had been recognised by resistant sera in ELISAs above, including: TC14222, TC7158, CK174651, TC10097, TC9597, TC9753, TC12175, and TC13841. An efficacy of 41% was obtained in a challenge trial in Australia.
3. Trial 2 also included TC13011 which was tested as yeast recombinant achieving 34% efficacy as a single protein in a challenge trial in Australia.

Figure 3:
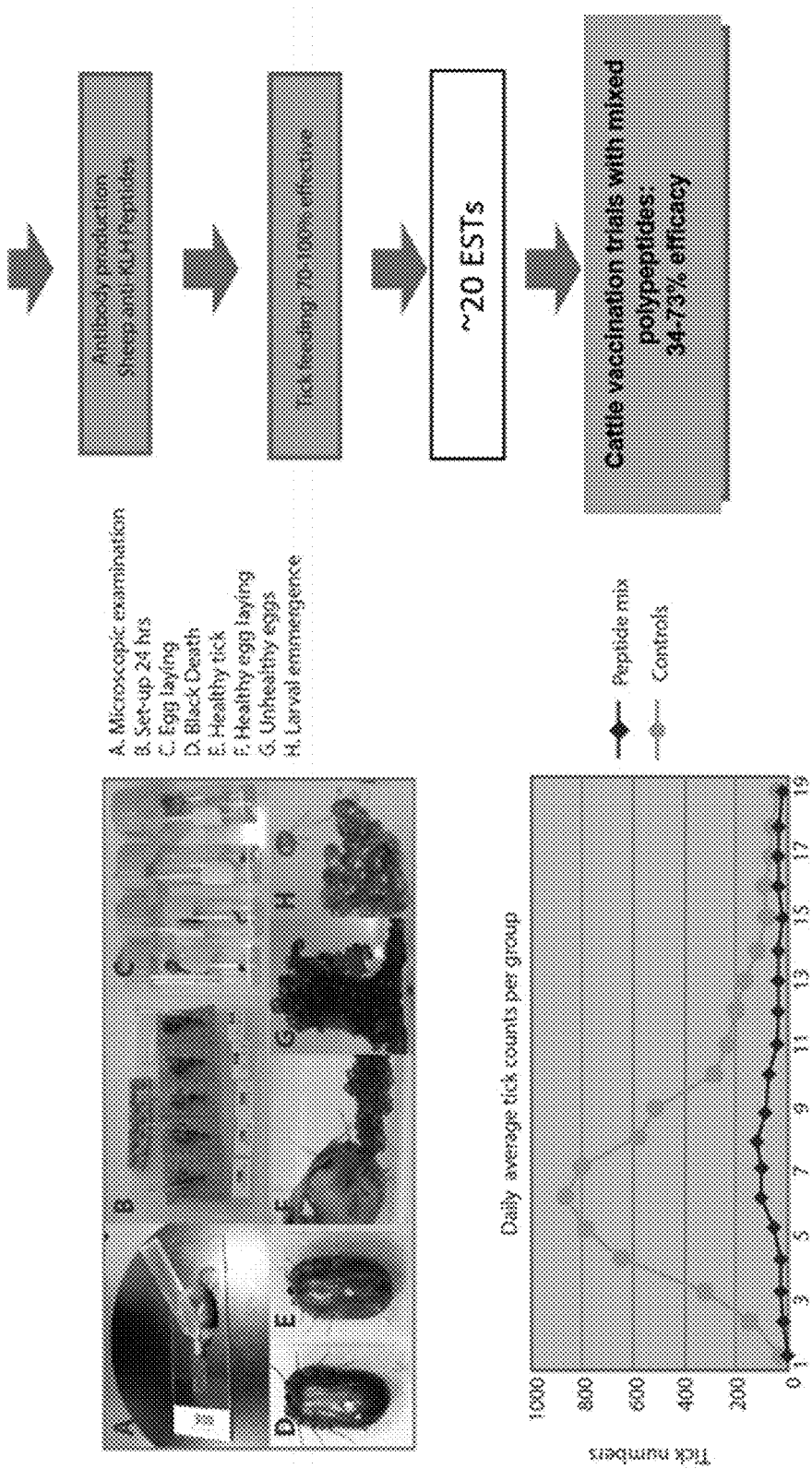

FIG. 3 shows the final stage of reverse vaccinology diagram discovery. All trial efficacies are summarised in Table 13 in Example 5.

Example 5: Preliminary Candidate Peptide Immunogenicity Against Ticks In Vivo Following the preliminary 2 trials, further trials using individual peptides were undertaken to select the protective component of the tested mixtures.

Materials and Methods

Peptides

Peptides and/or recombinant proteins produced in *Pichia pastoris* (Invitrogen as per manufacturer's instructions) were prepared and tested. The peptides were synthesised by Mimotopes (Melbourne, Australia) and conjugated to Keyhole Limpet Hemocyanin (KLH) carrier protein via a standard linker to the peptide incorporating an N-terminal cysteine amino acid residue. The KLH conjugate was used for the experiments herein as the carrier protein for the peptides is known to recruit T helper cells (see, Yang et al., 2001 Chapter 12 In: Ellis, R. W. (Ed.), New Vaccine Technologies. Medical Intelligence Unit, Eurekah.com/Landes Bioscience, Georgetown, Tex., USA, pp 214-26). The logic for targeting B-cell epitopes is based on the damage that host antibodies can elicit on feeding ticks.

Vaccination and Antibody Screening

Each trial included an un-vaccinated group injected with adjuvant mixed with PBS (randomly allocated as vaccination group numbers). Mimotope KLH conjugated peptides were provided as lyophilised powders (1 mg/tube) and re-suspension in PBS required 3×30 s rounds of sonication. The adjuvants and peptides (PBS only for controls) were mixed using a homogeniser for 1 min (LabGen 700, Cole Palmer) to ensure suspension of the vaccine mixtures. Cattle were vaccinated on Day 0 with 200 µg per peptide/recombinant protein using Freund's Complete adjuvant (1:1) in a total volume of 1 ml. On Days 28 and 49, cattle were re-vaccinated using Freund's Incomplete adjuvant (1:1) in a total volume of 2 ml. Blood samples were collected from each steer prior to each vaccination, and the sera obtained were labelled V0 (Day 0), V1 (Day 28), and V2 (Day 48). Blood was also collected prior to larval infestation and was labelled V3 (Day 63). After completion of the tick infestation, within the week a final serum sample was collected (V4) to see if antibody levels changed following tick challenge. Cattle were monitored after each vaccination for reactions to the adjuvants used. When elevated temperatures were observed, the cattle were treated with Ketoprofen as appropriate (non-steroidal pain relief).

Animals from each experimental group were screened by ELISA for the production of peptide specific IgG antibodies. The serum samples used were those prepared from blood collected prior to vaccination (naïve, V0) compared to those collected after each vaccination as well as following tick infestation (V1, V2, V3 and V4). The ELISA was conducted using 96 well flat bottomed polystyrene plates (cat #M2963-100, Sigma Aldrich) which were coated with 100 ng of un-conjugated peptides per well dissolved in a 1 ng/µl solution of 0.1 M carbonate buffer (pH 9.6) and incubated overnight at 4° C. Plates were washed twice with 200 µl wash solution per well (WS: 1×PBS+0.1% Tween 20) and blocked with 200 µl of Blocking Solution (BS:1×PBS+1% BSA+1% skim milk powder). Plates were incubated at room temperature (RT) for 1 hr, shaking gently and washed 3 times with WS. Serial two-fold dilutions of sera were prepared in duplicate from 1/100 to endpoint using PBS. Plates were incubated with 100 µl of diluted sera for 1 hr with gentle shaking at RT followed by 3 washes with WS. Rabbit anti-Bovine IgG conjugated with Horse Radish Peroxidase (Sigma Catalogue #A5295) was diluted 1:1000 in WS and used as the secondary antibody. A total of 100 µl per well was added to each plate and incubated at RT for 1 hr with shaking. Plates were washed 3 times with WS and developed using the TMB Liquid Substrate System (cat #T0440-100, Sigma Aldrich) as described by the manufacturer. Briefly, 100 µl of the TMB substrate was added to each well and incubated for 10 mins in the dark. The reaction was stopped by adding 100 µl/well of 1M phosphoric acid. The absorbance was read at 450 nm using an EPOCH Microplate reader (Biotek Instruments, Millenium Science). Animals from each group were screened against respective peptide(s) used during the immunisation of the group. The average titre was normalised to pooled pre-vaccinated sera titres.

Infestation, Tick Collections, Assessment of Efficacy of Vaccinations and Statistics After the third vaccination, cattle were separated into tick moat individual pens to acclimatise prior to tick infestations. These pens (PC1 facility, QASP UQ Gatton campus) are located in a temperature controlled building, 10 m² raised mesh floors, sealed walls, feed bins and automatic waterers. At Pinjarra Hills farm (Trial 4 infestation), the tick infestation unit is outdoors, raised mesh floors, sealed walls between pens, feed bins and manual watering. Two weeks later (day 63), cattle were infested with 2,500 larvae twice 2 days apart (total 5,000 larvae). Nineteen days after tick infestation, ticks were collected daily to collect data for total tick numbers (per animal per day) and total tick weights prior to the incubation of a subset of 50 ticks for egg production assessments. Ticks were incubated at the Qld Bioscience Precinct DAF/QAAFI laboratory (UQ St. Lucia campus) in a humidified incubator (Thermoline) at 27° C. and 85% relative humidity. After eggs were weighed, subsets of 0.25 g of eggs were incubated to determine the percent larval emergence (egg viability/fertility). Larvae were examined to determine percentage larval emergence by freezing the samples to enable the counting of the number of larvae emerged and eggs which did not hatch.

The most recent review of tick trial efficacy analysis (Cunha et al., 2013) follows on from the methods previously described by Fragoso et al. (1998) and de la Fuente et al. (1999). Cunha et al. (2013) define efficacy as:

Efficacy (%)=100×[1−(NET×$EW$×$EC$)], where were tested using the protected LSD test. The partial percentage efficacies for NET, EW and EC were calculated as:

Efficacy %=100(1−10**(Vaccine mean−Control mean))

These mean differences (for each measure, on the log 10-scale) were then summed to give the overall efficacy for each vaccine, giving the same values as the ratio-based formula of Cunha et al. (2013) above. The standard error for the overall efficacy was calculated from the standard errors of each partial efficacy, using the standard statistical formulae (Goodman, 1960). This calculation then allows a direct t-test of the overall efficacy against zero, for each vaccine.

Results

Summary of Vaccination Efficacies:

TABLE 13

Summary of efficacies for all trials using updated trial analysis methods

| Trial no. | Vaccination | Efficacy | Comments |
|---|---|---|---|
| A | TC12130, MPAAN50TR, TC14222, TC7158 | 73% | Saponin adjuvant, 15,000 larval challenge; |
| B* | Polypeptide yeast recombinant: CK174651, TC9753, TC10097, TC9597, TC7158, TC14222, TC13841, TC12175 | 41% | Incomplete Freund's, 45,000 larval challenge; |
| C | rTC13011 yeast recombinant | 34% | As above for the yeast polypeptide trial. |
| 1 | TC12130-1; TC12130-2 MPAAN50TR | 5% 16% | |
|   | TC12130, MPAAN50TR, TC14222, TC7158 | 30% | (47% if calculated using tick wts instead of egg wt/tick) - not at 73% as in Brazil trial |
| 2 | TC13011-1; TC13011-2 TC10097-1; TC10097-2 | 12% 18% | |
| 3 | TC12142-1; TC12142-2 TC9753 | 66% 63% | |
| 4 | TC8992 TC13140 rTC13011 (recombinant bacteria) MPAA730TR TC5995-1 (unconjugated) TC5995-2 | | Ticks from the control group were not viable in this trial. Efficacies could not be determined. Decreased tick numbers noted for MPAA730TR and TC5995. |
| 5 | TC12142-1; TC12142-2 TC8992 TC5995-2 | *64% 38% 65% | |

*For TC12142 using a pooled efficacy of 65% (trials 3 and 5) with a 95% confidence interval of 18.6% to 84.9% - this vaccination is formally significant (effect > zero) at P = 0.017.

NET=the ratio of the average total tick numbers (vaccinated group/control group), EW=the ratio of the average weight of eggs (g) per number of ticks incubated (vaccinated group/control group), and EC=the ratio of the percent larval emergence (vaccinated group/control group).

In these trials, all ticks collected were not incubated to determine fertility. Hence EW and EC were estimated on a subset of 250 ticks incubated per animal.

The effects of the vaccines on the total number of ticks (NET), weight of eggs (EW), and larval emergence (EC) were tested for statistical significance by ANOVA, with each variable being log 10-transformed before analysis to stabilise variance. Pair-wise differences between vaccine means ELISA Results Total IgG was determined against each peptide from each trial. End-point titres for each time point from each trial is summarised in Table 12. The time points were:

1. Pre-vaccination, naïve, Day 0
2. Post vaccination 1, at 4 weeks
3. Post vaccination 2 (boosted at 4 weeks), at 7 weeks
4. Post vaccination 3 (boosted at 7 weeks), at 9 weeks
5. Post infestation, at ~13 weeks ~30 days after larval infestation (~week after completed tick life cycle)

All vaccinations in Trial 3 had notable vaccine efficacies ranging from 63-66%. In addition, all titres were boosted following tick infestation.

Tick collections from Trial 4 were not optimal thus efficacies were not calculated. TC8992 and TC5995 had increased titres post tick challenge.

Trial 5 again re-tested TC12142 peptides, with TC12142-2 (SEQ ID NO: 51) producing higher titres again. However, overall the titres were much lower for both peptides in Trial 5 compared to Trial 3 which may correlate to lower tick numbers for this vaccination group in Trial 3 not noted in Trial 5. The efficacies were otherwise comparable between trials 3 and 5 for TC12142 (64-66%). Titres for TC5995 were not boosted by tick challenge falling to zero, however this vaccination had a high efficacy of 65%. TC8992 had an efficacy of 38% and the titre decreased following tick challenge compared to Trial 4 results but notably the standard deviations are quite high.

BIBLIOGRAPHY deCastro, J. J., Sustainable tick and tickborne disease control in livestock improvement in developing countries, Vet. Parasitol., 1997 71: 71-97.

Lew-Tabor A. E., Moolhuijzen, P. M., Vance, M. E., Kurscheid, S., Rodriguez Valle M., Jarrett S., Minchin C. M., Jackson, L. A., Jonsson, N. N., Bellgard M. I., and Guerrero F. D. (2010b) Suppressive subtractive hybridization analysis of Rhipicephalus (Boophilus) microplus transcript expression during feeding and attachment. Veterinary Parasitology 167 (2-4): 304-320.

Lew-Tabor, A. E., Bruyeres, A. G., Zhang, B., Rodriguez Valle, M. (2014) Rhipicephalus (Boophilus) microplus tick in vitro feeding methods for functional (dsRNA) and vaccine candidate (antibody) screening. Ticks and Tick Borne Diseases, 5:500-510.

Lew-Tabor, A. E. and Rodriguez Valle, M. (2016) A review of reverse vaccinology approaches for the development of vaccines against ticks and tick borne diseases. Ticks & Tick Borne Diseases 7:573-585

Playford M, Rabiee A R, Lean I J, Ritchie M: Review of research needs for cattle tick control, Phases I and II. In.: Meat & Livestock Australia Ltd., Locked Bag 991, North Sydney NSW 2059; 2005: ISBN 1 74036 74685 74039.

Rand et al., Cloning and expression of a protective antigen from the cattle tick Boophilus microplus, Proc. Natl. Acad. Sci. USA, 1989, 86: 9657-9661.

Garcia-Garcia et al., Sequence variations in the Boophilus microplus Bm86 locus and implications for immunoprotection in cattle vaccinated with this antigen, Exp. App. Acar. 1999, 23: 883-895.

Cunha, et al., Calculation of the efficacy of vaccines against tick infestations on cattle, Rev. Bras. Parasitol. Vet., 2013, 22 (4) 571-578.

de la Fuente, et al., Vaccination against ticks (Boophilus spp.): the experience with the Bm86-based vaccine Gavac, Genet. Anal., 1999, 15: 143-148.

Piper, E., Jonsson, N., Gondro, C., Vance, M., Lew-Tabor, A., Jackson, L. (2017) Peripheral cellular and humoral responses to infestation with Rhipicephalus microplus in Santa-Gertrudis cattle. Parasite Immunology 39: e12402.

Rodriguez Valle, M., Lew-Tabor, A. E., Gondro, C., Moolhuijzen, P., Vance, M., Guerrero, F. D., Bellgard, M. I., Jorgensen, W. (2010) Comparative microarray analysis of Rhipicephalus (Boophilus) microplus expression profiles of larvae pre-attachment and feeding adult female stages on Bos indicus and Bos taurus cattle. BMC Genomics 11:437.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A composition comprising:
 a recombinant or synthetic polypeptide comprising or consisting of the amino acid sequence set forth in residues 140-154 of SEQ ID NO: 7 (SEQ ID NO: 52) and/or residues 159-179 of SEQ ID NO: 7 (SEQ ID NO: 51);
 an adjuvant for potentiating an immune response to the polypeptide.

2. The composition according to claim 1, wherein the composition further comprises a polypeptide that comprises or consists of the amino acid sequence set forth in:
 residues 20-37 of SEQ ID NO: 10 (SEQ ID NO: 58);
 residues 96-106 of SEQ ID NO: 10 (SEQ ID NO: 59);
 residues 164-173 of SEQ ID NO: 10 (SEQ ID NO: 60); and
 residues 185-200 of SEQ ID NO: 10 (SEQ ID NO: 61).

3. The composition according to claim 1, wherein the composition further comprises a polypeptide comprising or consisting of the amino acid sequence residues 198-209 of SEQ ID NO: 14, (SEQ ID NO: 70).

4. The composition according to claim 1, wherein the composition further comprises a polypeptide that comprises or consists of the amino acid sequence set forth in:
- residues 91-132 of SEQ ID NO: 16 (SEQ ID NO: 72);
- residues 104-204 of SEQ ID NO: 16 (SEQ ID NO: 73); and
- residues 117-132 of SEQ ID NO: 16 (SEQ ID NO: 74).

5. The composition according to claim 1, wherein the composition further comprises:
- a carrier protein, conjugated to the recombinant or synthetic polypeptide; and/or
- a pharmaceutically acceptable carrier, excipient, or diluent.

6. The composition according to claim 1, wherein the recombinant or synthetic polypeptide comprises or consists of the amino acid sequence set forth in SEQ ID NO: 7.

7. The composition according to claim 1, wherein the composition further comprises a polypeptide that comprises or consists of the amino acid sequence set forth in SEQ ID NO: 10.

8. The composition according to claim 1, wherein the recombinant or synthetic polypeptide comprises or consists of the amino acid sequence set forth in SEQ ID NO: 7 and wherein the composition further comprises a polypeptide that comprises or consists of the amino acid sequence set forth in SEQ ID NO: 10.

9. The composition according to claim 1, wherein the composition further comprises a polypeptide that comprises or consists of the amino acid sequence set forth in SEQ ID NO: 14.

10. The composition according to claim 1, wherein the recombinant or synthetic polypeptide comprises or consists of the amino acid sequence set forth in SEQ ID NO: 7 and wherein the composition further comprises a polypeptide that comprises or consists of the amino acid sequence set forth in SEQ ID NO: 14.

11. The composition according to claim 1, wherein the composition further comprises a polypeptide that comprises or consists of the amino acid sequence set forth in SEQ ID NO: 16.

12. The composition according to claim 1, wherein the recombinant or synthetic polypeptide comprises or consists of the amino acid sequence set forth in SEQ ID NO: 7 and wherein the composition further comprises a polypeptide that comprises or consists of the amino acid sequence set forth in SEQ ID NO: 16.

13. The composition according to claim 1, wherein the recombinant or synthetic polypeptide comprises or consists of the amino acid sequence set forth in SEQ ID NO: 7 and wherein composition further comprises a carrier protein, conjugated to the recombinant or synthetic polypeptide; and/or a pharmaceutically acceptable carrier, excipient, or diluent.

* * * * *